United States Patent
Schaus et al.

(10) Patent No.: US 9,567,331 B2
(45) Date of Patent: Feb. 14, 2017

(54) PYRIDOPYRIMIDINONE INHIBITORS OF VIRUSES

(71) Applicant: Trustees of Boston University, Boston, MA (US)

(72) Inventors: Scott E. Schaus, Boston, MA (US); Lauren Brown, Brighton, MA (US); John Connor, Newton, MA (US); Ken William Dower, Medford, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 14/357,920

(22) PCT Filed: Nov. 15, 2012

(86) PCT No.: PCT/US2012/065245
§ 371 (c)(1),
(2) Date: May 13, 2014

(87) PCT Pub. No.: WO2013/115884
PCT Pub. Date: Aug. 8, 2013

(65) Prior Publication Data
US 2014/0288095 A1    Sep. 25, 2014

Related U.S. Application Data

(60) Provisional application No. 61/560,031, filed on Nov. 15, 2011.

(51) Int. Cl.
*A61K 31/519*    (2006.01)
*C07D 471/04*    (2006.01)
(Continued)

(52) U.S. Cl.
CPC ........... *C07D 471/04* (2013.01); *A61K 31/519* (2013.01); *A61K 45/06* (2013.01); *C12Q 1/70* (2013.01)

(58) Field of Classification Search
CPC .................................................... A61K 31/519
(Continued)

(56) References Cited

U.S. PATENT DOCUMENTS 4,361,700 A    11/1982    Purcell et al.
5,556,854 A    9/1996    Furrer et al.
(Continued)

FOREIGN PATENT DOCUMENTS

EP    1567653    6/2007
EP    2366776    9/2011

OTHER PUBLICATIONS

Pabel et al. "Asymmetric synthesis of Pyrido[1,2-c]pyrimidinones," Journal of Chemical Sciences, 2009, vol. 64, No. 6, pp. 653-661.*
(Continued)

*Primary Examiner* — Shengjun Wang
(74) *Attorney, Agent, or Firm* — Nixon Peabody LLP

(57) ABSTRACT

Provided herein are novel small molecule pyridomyrimidone viral inhibitor agents of Formula (I), such as 4-acetyl-2,3,7,8-tetrahydro-3-phenylpyrido[1,2-f]pyrimidin-1-one, and methods of using pharmaceutical or therapeutic compositions comprising such viral inhibitor agents of Formula (I) in inhibiting and treating viral infections including orthopox and retroviral infections. Methods of synthesizing such agents are also provided herein.

(Continued)

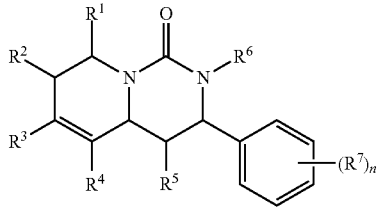

(I)

15 Claims, 16 Drawing Sheets

(51) Int. Cl.
   *A61K 45/06* (2006.01)
   *C12Q 1/70* (2006.01)
(58) Field of Classification Search
   USPC .................................................... 514/259.4
   See application file for complete search history.

(56) References Cited

U.S. PATENT DOCUMENTS

| 5,591,742 | A  | 1/1997  | Bell et al.    |
|-----------|----|---------|----------------|
| 8,044,062 | B2 | 10/2011 | Baik et al.    |
| 2006/0110407 | A1 | 5/2006  | Stopera et al. |
| 2008/0188498 | A1 | 8/2008  | Zhu            |
| 2008/0194616 | A1 | 8/2008  | Liu et al.     |

2011/0023760 A1 2/2011 Maghdissian et al.

OTHER PUBLICATIONS

Brown et al., "Gold Catalyzed Cyclization of Alkyne-Tethered Dihydropyrimidones", Organic Letters, 13(16): 4228-4231 (2011).
Broyles et al., "Vaccinia virus transcription", J Gen Virol, 84: 2293-2303 (2003).
Drazen et al., "Smallpox and Bioterrorism", N. Engl J Med, 346(17): 1262-1263 (2002).
Fenner, "A Succesful Eradication Campaign", Rev Infect Dis, 4:916-930 (1982).
McFadden, G., "Poxvirus Tropism", Nat Rev Microbiol, 3(3):201-213 (2005).
Moss, B., "Poxviridae: The Viruses and Their Replication", 5th ed, vol. 2 (2007).
Parker et al., "Human monkeypox: an emerging zoonotic disease", Future Microbiol, 2(1): 17-34 (2007).
Reed et al., "The Detection of Monkeypox in Humans in the Western Hemisphere", N. Engl J Med, 3504(4): 342-350 (2004).
Rimion et al., "Major increase in human monkeypox incidence 30 years after smallpox vaccination campaigns cease in the Democratic Republic of Congo", PNAS, 107(37): 16262-16267 (2010).
Roberts et al., "Vaccinia virus morphogenesis and dissemination", Trends Microbiol, 16: 472-479 (2008).
Rubins et al., "The temporal program of peripheral blood gene expression in the response of nonhuman primates to Ebola hemorrhagic fever", Genome Biol, 8: R174 (2007).
Seet et al., "Poxviruses and Immune Evasion", Ann Rev Immunol, 21: 377-423 (2003).
Wolf et al., "Host Restriction Factors Blocking Retroviral Replication", Annu Rev Genet, 42: 143-163 (2008).

\* cited by examiner

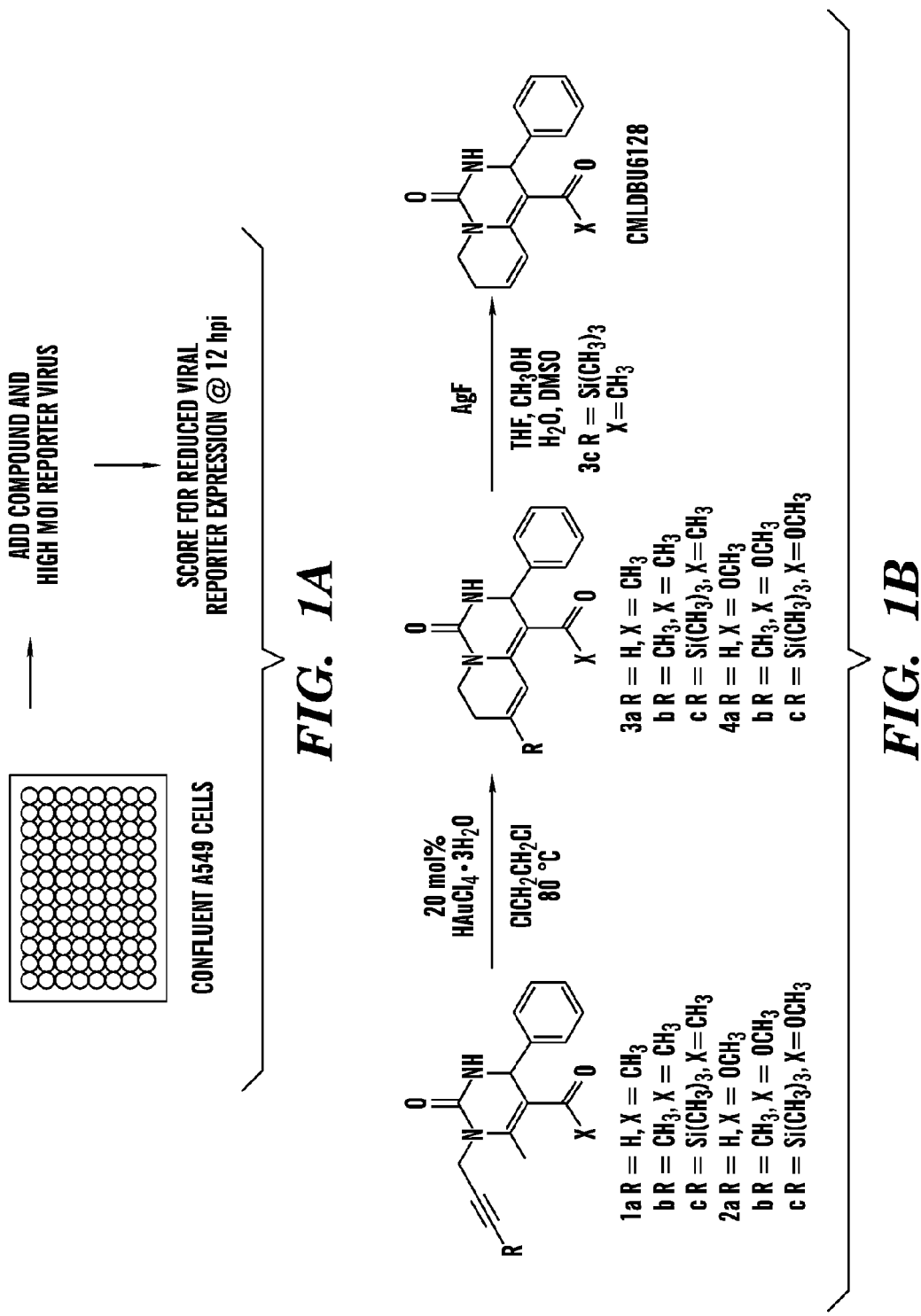

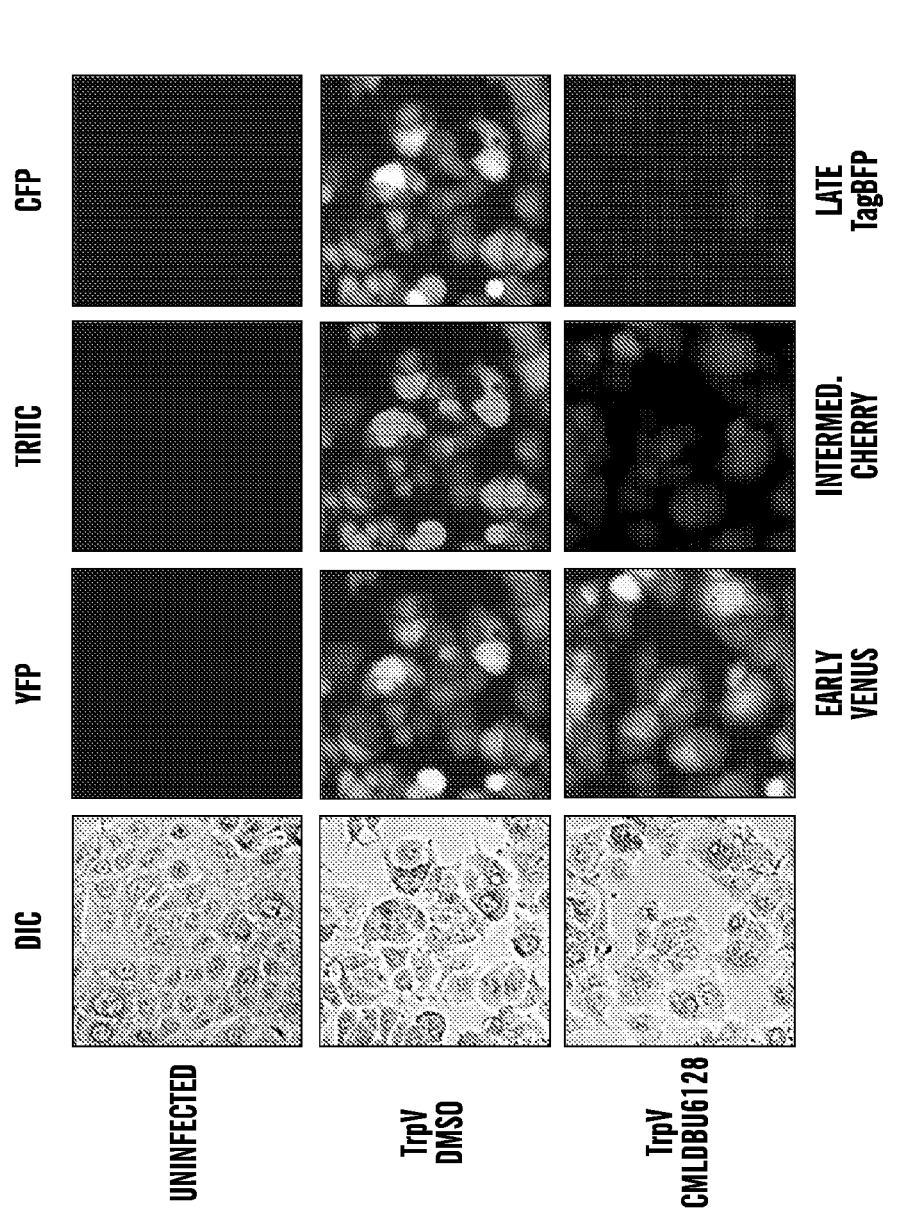

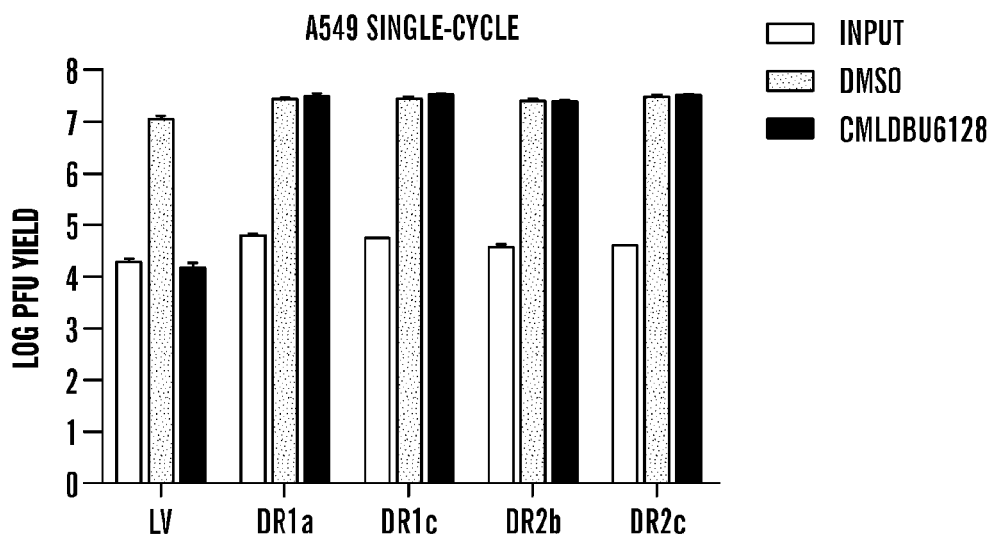
FIG. 6B
CODING CHANGES FROM PARENTAL LV:
| CLONE | nt | CDS |
|---|---|---|
| DR1a | T8584G | VACWR098; J6R V576G |
| DR1c | T8584G | VACWR098; J6R V576G |
| DR2b | C86976T | VACWR098; J6R A954V |
| DR2c | C86976T | VACWR098; J6R A954V |
FIG. 6C
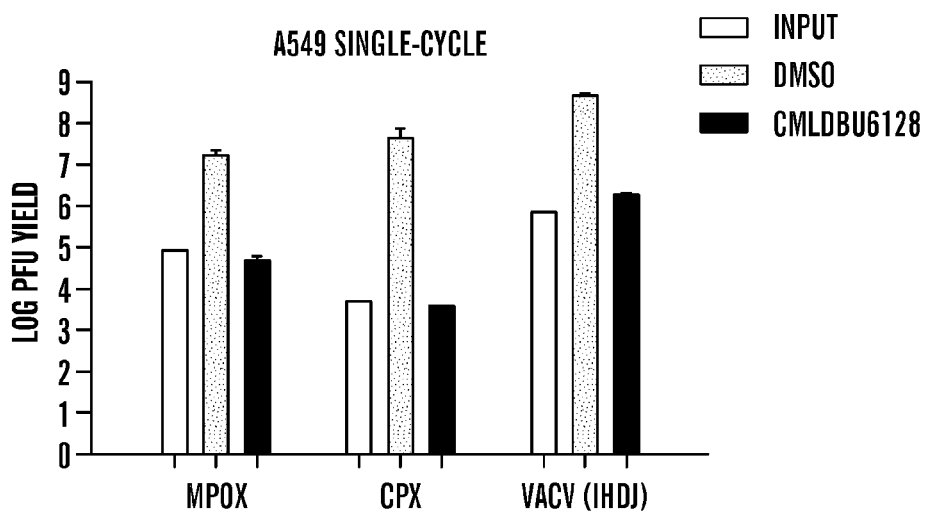
FIG. 6D

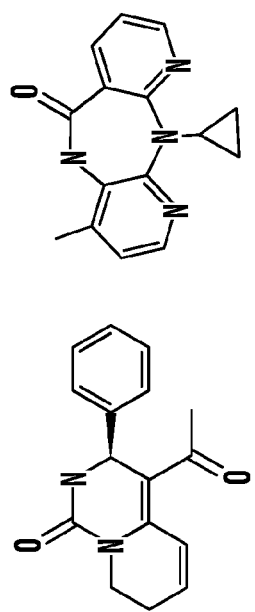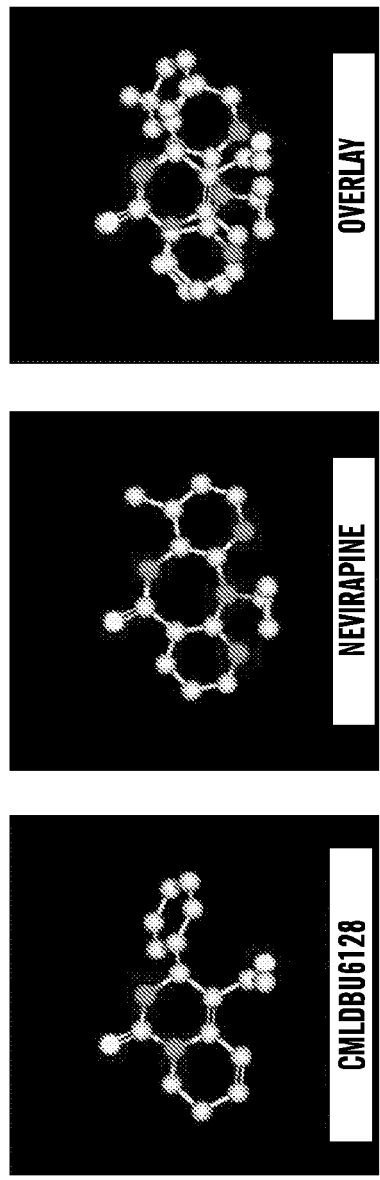
FIG. 7A
FIG. 7B

PYRIDOPYRIMIDINONE INHIBITORS OF VIRUSES

CROSS REFERENCE TO RELATED APPLICATIONS

This application is a 35 U.S.C. §371 National Phase Entry Application of International Application No. PCT/US12/65245 filed Nov. 15, 2012, which designates the U.S., and which claims benefit under 35 U.S.C. §119 of U.S. Provisional No. 61/560,031 filed on Nov. 15, 2011, the contents of each of which are herein incorporated by reference in their entireties.

GOVERNMENT SUPPORT

This invention was made with Government Support under Contract No. W81XWH-10-2-0008 awarded by the Department of the Army and Contract No. GM086180 awarded by the National Institutes of Health. The Government has certain rights in the invention.

FIELD OF THE INVENTION

This invention relates to pyridopyrimidinone compositions as viral inhibitors and therapeutic uses thereof, and assays for identifying viral inhibitors.

BACKGROUND

The Poxyiridae family of DNA viruses includes the orthopoxviruses Variola (smallpox) and the emerging pathogen monkeypox. Naturally occurring smallpox was eradicated through concerted vaccination with the prototypical orthopoxvirus, vaccinia, and routine vaccination has since been discontinued[1]. The potential use of smallpox as a bioweapon, however, has heightened interest in developing countermeasures[2]. In addition, recent reports show an increase in human monkeypox cases in Africa over the last 30 years[3], and the first report of human monkeypox in the Western Hemisphere occurred in 2003[4].

Orthopoxviruses replicate in the cytoplasm and encode macromolecular machinery for transcription, post-transcriptional mRNA processing, and DNA genome replication[6]. Gene expression proceeds in a classical cascade mechanism that is broadly categorized into early, intermediate, and late phases[7]. Viral replication occurs in perinuclear viral factories and a major mode of transmission of these predominantly intracellular viruses is to adjacent cells via trafficking to the cell membrane or upon infected cell rupture[8]. While these core viral functions are conserved across orthopoxviruses, host-range and virulence factors are divergent[9][10]. Variola is an obligate human pathogen with a mortality rate of 30-50% which caused an estimated 300-500 million deaths in the 20$^{th}$ century[11]. Monkeypox has a mortality rate of 1-10% and can transmit to humans zoonotically from animal reservoirs[12].

Retroviruses are extremely successful pathogens affecting virtually all branches of life. These viruses are champions of persistence, and are maintained as proviral DNAs integrated into the genome of somatic cells and can even enter into the germ line. Infection can result in cell death, or in oncogenic transformation by insertional mutagenesis. Thus, there is tremendous evolutionary selective pressure to block or prevent retrovirus replication (D. Wolf and S. P. Goff, 2008, Ann. Rev. Gen., 42: 143-163).

SUMMARY OF THE INVENTION

Described herein are novel small molecule pyridomyrimidone viral inhibitor agents of Formula (I), such as 4-acetyl-2,3,7,8-tetrahydro-3-phenylpyrido[1,2-f]pyrimidin-1-one, also termed herein as "CMLDBU6128," and methods of using compositions comprising such viral inhibitor agents of Formula (I) in inhibiting and treating viral infections, such as orthopox and retroviral infections. As demonstrated herein, small molecule pyridomyrimidone inhibitor agents of Formula (I), such as 4-acetyl-2,3,7,8-tetrahydro-3-phenylpyrido[1,2-f]pyrimidin-1-one or "CMLDBU6128," are surprisingly effective inhibitors of replication of a variety of viruses, including different species of orthopox viruses, as well as HIV, a member of the lentivirus family of retroviruses. Methods of synthesizing such agents are also provided herein.

Accordingly, provided herein are therapeutic compositions comprising the small molecule pyridomyrimidone viral inhibitor agents of Formula (I), such as 4-acetyl-2,3,7,8-tetrahydro-3-phenylpyrido[1,2-f]pyrimidin-1-one. These therapeutic compositions are useful in the treatment and prevention of viral infections, such as orthopoxvirus infections and retroviral infections, and reducing or inhibiting transmission of orthopoxvirus and/or retroviral diseases.

Also provided herein are assays and methodologies for identifying compounds that inhibit members of the orthopoxvirus genus. These assays comprise, in part, generating and/or using targeted insertions of various reporter genes into viral genetic material. The reporter genes allow monitoring and tracking of the growth and replication of the viruses, thus providing a high-throughput, comprehensive and real-time analysis of viral replication at each life cycle stage of virus gene expression.

Accordingly, provided herein in some aspects are pharmaceutical or therapeutic compositions comprising a pyridopyrimidinone viral inhibitor of Formula (I):

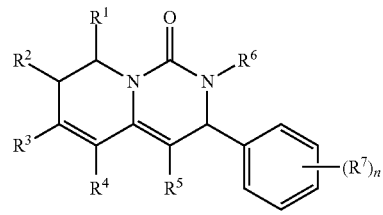

FORMULA (I)

wherein:

$R^1$, $R^2$ and $R^4$ are independently, H, alkyl, alkenyl, alkynyl, aryl, heteroaryl, cyclyl, heterocyclyl, acyl, amino, hydroxyl, alkoxy, $C(O)OR^8$, or $C(O)N(R^8)_2$, each of which can be optionally substituted;

$R^3$ is H, alkyl, alkenyl, alkynyl, aryl, heteroaryl, cyclyl, heterocyclyl, acyl, amino, or alkyl silane (e.g., trialkylsilane), each of which can be optionally substituted;

$R^5$ is H, alkyl, alkenyl, alkynyl, aryl, heteroaryl, cyclyl, heterocyclyl, acyl, amino, hydroxyl, alkoxy, mercapato, thioalkoxy, sulfinyl, sulfonyl, $C(O)OR^8$, or $C(O)N(R^8)_2$, each of which can be optionally substituted;

$R^6$ is H, alkyl, alkenyl, alkynyl, aryl, heteroaryl, cyclyl, heterocyclyl, or acyl, each of which can be optionally substituted;

R[7] is independently for each occurrence H, halo, cyano, amino, nitro, hydroxyl, mercapto, thioalkoxy, sulfinyl, sulfonyl, alkyl, alkenyl, alkynyl, alkoxy, acyl, aryl, heteroaryl, cyclyl, heterocyclyl, C(O)OR[8], or C(O)N(R[8])$_2$, each of which can be optionally substituted;

R[8] is H, alkyl, alkenyl, alkynyl, aryl, heteroaryl, cyclyl, or heterocyclyl, each of which can be optionally substituted;

n is 0, 1, 2, 3, 4, or 5; and pharmaceutically acceptable salts thereof.

In some embodiments of these aspects and all such aspects described herein, the pyridopyrimidinone viral inhibitor of Formula (I) is 4-acetyl-2,3,7,8-tetrahydro-3-phenylpyrido[1,2-f]pyrimidin-1-one (CMLDBU6128), having a chemical structure:

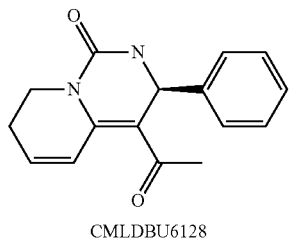 [SMILES: CC(=O)C1=C2C=CCCN2C(=O)N[C@H]1c1ccccc1]

CMLDBU6128

In some aspects, provided herein are methods of inhibiting viral replication, such methods comprising contacting a cell infected with a virus an effective amount of a pharmaceutical compositions comprising a pyridopyrimidinone viral inhibitor of Formula (I). In some embodiments of these aspects and all such aspects described herein, the pyridopyrimidinone viral inhibitor of Formula (I) is 4-acetyl-2,3,7,8-tetrahydro-3-phenylpyrido[1,2-f]pyrimidin-1-one (CMLDBU6128).

In some embodiments of these methods and all such methods described herein, the contacting is in vitro or ex vivo. In other embodiments of these methods, the contacting is in vivo.

In some embodiments of these methods and all such methods described herein, the virus is an orthopoxvirus.

In some embodiments of these methods and all such methods described herein, the virus is a retrovirus. In some such embodiments, the retrovirus is a lentivirus. In some such embodiments, the lentivirus is HIV.

In some aspects, provided herein are methods of inhibiting or preventing orthopoxvirus replication and/or infection in a subject in need thereof. Such methods comprise administering to a subject having, or at risk for, an orthopoxvirus infection, a therapeutically effective amount of a pharmaceutical composition comprising a pyridopyrimidinone viral inhibitor of Formula (I). In some embodiments of these aspects and all such aspects described herein, the pyridopyrimidinone viral inhibitor of Formula (I) is 4-acetyl-2,3,7,8-tetrahydro-3-phenylpyrido[1,2-f]pyrimidin-1-one (CMLDBU6128).

In some aspects, provided herein are methods of treating an orthopoxvirus infection in a subject in need thereof. Such methods comprise administering to a subject having an orthopoxvirus infection a therapeutically effective amount of a pharmaceutical composition comprising a pyridopyrimidinone viral inhibitor of Formula (I). In some embodiments of these aspects and all such aspects described herein, the pyridopyrimidinone viral inhibitor of Formula (I) is 4-acetyl-2,3,7,8-tetrahydro-3-phenylpyrido[1,2-f]pyrimidin-1-one (CMLDBU6128).

In some embodiments of these methods and all such methods described herein, the method further comprises the step of selecting, diagnosing, or identifying a subject having an orthopoxvirus infection or who is at increased risk for an orthopoxvirus infection, prior to administering to the subject the compositions described herein.

In some embodiments of these methods and all such methods described herein, the orthopoxvirus is a Vaccinia virus or a Variola virus.

In some embodiments of these methods and all such methods described herein, the method further comprises administration of one or more additional orthopoxvirus therapeutic agents, such as additional viral inhibitors.

Also provided herein, in other aspects, are methods of inhibiting or preventing retrovirus replication and/or infection in a subject in need thereof. Such methods comprise administering to a subject having, or at risk for, a retrovirus infection a therapeutically effective amount of a pharmaceutical composition comprising a pyridopyrimidinone viral inhibitor of Formula (I). In some embodiments of these aspects and all such aspects described herein, the pyridopyrimidinone viral inhibitor of Formula (I) is 4-acetyl-2,3,7, 8-tetrahydro-3-phenylpyrido[1,2-f]pyrimidin-1-one (CMLDBU6128).

In some aspects, provided herein are methods of treating a retrovirus infection in a subject in need thereof. Such methods comprise administering to a subject having a retrovirus infection a therapeutically effective amount of a pharmaceutical composition comprising a pyridopyrimidinone viral inhibitor of Formula (I). In some embodiments of these aspects and all such aspects described herein, the pyridopyrimidinone viral inhibitor of Formula (I) is 4-acetyl-2,3,7,8-tetrahydro-3-phenylpyrido[1,2-f]pyrimidin-1-one (CMLDBU6128).

In some embodiments of these methods and all such methods described herein, the method further comprises the step of selecting, diagnosing, or identifying a subject having a retrovirus infection or who is at increased risk for a retrovirus infection, prior to administering to the subject the compositions described herein.

In some embodiments of these methods and all such methods described herein, the retrovirus is a lentivirus. In some such embodiments, the lentivirus is HIV.

In some embodiments of these methods and all such methods described herein, the method further comprises administration of one or more additional retroviral therapeutic agents. In some such embodiments, the retroviral therapeutic agent is an anti-HIV agent.

In some aspects, provided herein are pyridopyrimidinone viral inhibitors of Formula (I) for use in treating an orthopoxvirus infection.

In some embodiments of these uses and all such uses described herein, the pyridopyrimidinone viral inhibitor of Formula (I) is 4-acetyl-2,3,7,8-tetrahydro-3-phenylpyrido[1,2-f]pyrimidin-1-one (CMLDBU6128).

In some embodiments of these uses and all such uses described herein, the orthopoxvirus is a Vaccinia virus or a Variola virus.

Also provided herein, in some aspects are pyridopyrimidinone viral inhibitors of Formula (I) for use in treating a retrovirus infection.

In some embodiments of these uses and all such uses described herein, the pyridopyrimidinone viral inhibitor of Formula (I) is 4-acetyl-2,3,7,8-tetrahydro-3-phenylpyrido[1, 2-f]pyrimidin-1-one (CMLDBU6128).

In some embodiments of these uses and all such uses described herein, the retrovirus is a lentivirus. In some such embodiments, the lentivirus is HIV.

Also provided herein, in some aspects, are screening assays for identifying an orthopoxvirus inhibitor. Such assays comprise: (a) contacting a population of cells infected with a reporter orthopoxvirus with a test compound, where the reporter orthopoxvirus comprises one or more reporter molecules each operably linked to a different viral gene promoter, and where expression of the one or more reporter molecules is indicative of a particular stage of the orthopoxvirus life cycle; (b) contacting the population of cells of step (a) with a test compound; and (c) measuring and/or analyzing the expression of the one or more reporter molecules expressed by the reporter orthopoxvirus following the contacting with the test compound, such that a decrease in expression or lack of expression of the one or more reporter molecules relative to a control population of cells infected with the reporter orthopoxvirus that was not contacted with the test compound is indicative of the test compound being an orthopoxvirus inhibitor.

In some embodiments of these screening assays, the one or more reporter molecules is a fluorescent molecule, a luciferase molecule, or an enzyme. In some embodiments of these screening assays, the viral gene promoter is an intermediate viral promoter or a late viral promoter.

DEFINITIONS

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein, the terms "viral inhibitor" or "inhibitor of viruses," refer to an agent, such as a small molecule of Formula (I), that inhibits or causes or facilitates a qualitative or quantitative inhibition, decrease, or reduction in one or more processes, mechanisms, effects, responses, functions, activities or pathways mediated by a virus. Such changes mediated by a viral inhibitor of Formula (I) can refer to a decrease in the expression, activity, or function of the viral genes expressed by a virus, such as a decrease in, inhibition of, or diversion of, virus activity, infectivity, or replication. Thus, the term viral inhibitor refers to an agent that inhibits or blocks expression of one or more viral genes, such as intermediate or late viral genes, tat, pol, or gag genes, or an agent that partially or totally blocks or arrests viral protein synthesis, viral assembly, viral infectivity, viral DNA replication, viral genome integration into a host genome, viral polymerase activity or function, viral integrase activity or function, viral reverse transcriptase activity or function, or any combination thereof. As used herein, the term "expression," refers to the processes involved in producing RNA and proteins and as appropriate, secreting proteins, including where applicable, but not limited to, for example, transcription, translation, folding, modification and processing. "Expression products" include RNA or DNA transcribed from a viral gene and polypeptides obtained by translation of mRNA transcribed from a viral gene.

The terms "inhibit," "decrease," and "reduce," are all used herein generally to mean a decrease by a statistically significant amount. Accordingly, viral inhibition is achieved when the expression of one or more viral genes, such as intermediate or late viral genes, tat, pol, or gag viral genes, viral protein synthesis, viral assembly, viral infectivity, viral DNA replication, viral genome integration into a host genome, viral polymerase activity or function, viral integrase activity or function, viral reverse transcriptase activity or function, or any combination thereof, is about at least 10% less, at least 20% less, at least 30% less, at least 40% less, at least 50% less, at least 60% less, at least 70% less, at least 80% less, at least 90% less, at least 95% less, at least 98% less, at least 99% less, up to including 100% or less, i.e., absent, or undetectable, in the presence of the viral inhibitor of Formula (I) relative to a reference level or sample or control level or sample in the absence of the viral inhibitor.

The term "agent" as used herein in reference to a viral inhibitor means any compound or substance such as, but not limited to, a small molecule, nucleic acid, polypeptide, peptide, drug, ion, etc. An "agent" can be any chemical, entity, or moiety, including, without limitation, synthetic and naturally-occurring proteinaceous and non-proteinaceous entities. In some embodiments, an agent is a nucleic acid, a nucleic acid analogue, a protein, an antibody, a peptide, an aptamer, an oligomer of nucleic acids, an amino acid, or a carbohydrate, and includes, without limitation, proteins, oligonucleotides, ribozymes, DNAzymes, glycoproteins, siRNAs, lipoproteins, aptamers, and modifications and combinations thereof etc. In certain embodiments, as described herein, agents are small molecules having a chemical moiety.

The terms "subject" and "individual" are used interchangeably herein, and refer to an animal, for example a human, that an orthopoxvirus is capable of infecting, and/or a recipient of the viral inhibitors of Formula (I) described herein. For treatment of those viral infections that are specific for a specific animal, such as a human subject, the term "subject" refers to that specific animal. The terms 'non-human animals' include, for example, mammals such as rats, mice, rabbits, sheep, cats, dogs, cows, pigs, and non-human primates, and birds, such as chickens, ducks, waterfowl, etc.

As used herein, the term "orthopoxvirus infection" describes a disease state, in which an orthopoxvirus invades a healthy cell, uses the cell's reproductive machinery to multiply or replicate and ultimately lyse the cell resulting in cell death, release of viral particles and the infection of other cells by the newly produced progeny viruses. Latent infection by orthopoxviruses is also a possible result of viral infection.

Examples of orthopoxvirus infections that can be inhibited or treated using the compositions and methods described herein include, but are not limited to, aractuba virus, BeAn 58058 virus, buffalopox virus, camelpox virus (such as, for example, Camelpox virus 903, Camelpox virus CMG, Camelpox virus CMS, Camelpox virus CP1, Camelpox virus CP5, and Camelpox virus M-96), cantagalo orthopoxvirus, cowpox virus (such as, for example, Cowpox virus strain Hamburg-1985 and Cowpox virus strain Turkmenia-1974), Ectromelia virus (such as, for example, Belo Horizonte virus), elephantpox virus, horsepox virus, monkeypox virus (such as Monkeypox virus strain Sierra Leone 70-0266 and Monkeypox virus strain Zaire 77-0666), myxomaxvirus, rabbitpox virus (such as Rabbitpox strain Utrecht), raccoonpox virus, skunkpox virus, tanapoxvirus, taterapox virus, vaccinia virus (including, but not limited to, the following strains: strain Ankara, strain Copenhagen, strain Dairen I, strain IHD-J, strain L-IPV, strain LC 16M8, strain LC 16M0, strain Lister, strain LIVP, strain Tian Tan, strain WR 65-16, strain WR, and strain Wyeth), Variola virus (such as variola major virus and variola minor virus), and volepox virus.

As used herein, the phrase "treating or preventing orthopoxvirus infection" means to inhibit the replication of the particular orthopoxvirus, to inhibit orthopoxvirus transmission, or to prevent the orthopox from establishing itself in its host, to ameliorate or alleviate the symptoms of the disease caused by the orthopoxvirus infection, or any combination thereof. The treatment is considered therapeutic, for example, if there is a reduction in viral load, viral replication, viral counts, decrease in mortality, and/or morbidity, or any combination thereof. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least a slowing of progress or worsening of symptoms that would be expected in absence of treatment.

As used herein, "alleviating a symptom of an orthopoxvirus infection" is ameliorating or reducing any condition or symptom associated with the infection. As compared with an equivalent untreated control or reference subject, such reduction or degree of prevention is at least 5%, at least 10%, at least 20%, at least 30%, at least 40%, at least 50%, at least 60%, at least 70%, at least 80%, at least 90%, at least 95%, at least 98%, at least 99%, or more, as measured by any standard technique. Ideally, the infection is completely cleared, or undetectable, as measured by any standard method known in the art.

The term "orthopoxvirus therapy" or "orthopoxvirus therapeutic agent" refers to a therapy useful in treating an orthopoxvirus infection. Examples of orthopoxvirus therapeutic agents include, but are not limited to, e.g., Vaccinia virus immunoglobulin (VIG), CIDOFOVIR ([(S)-1-(3-hydroxy-2-phosphonylmethoxypropyl)cytosine] [HPMPC]), methisazone, inhibitors of S-adenosylhomocysteine hydrolase (SAH), analogs of the nucleoside adenosine, such as NEPLANACIN A and 3-DEAZANEPLANACIN A, interferons, cytokines, antagonists (e.g., neutralizing antibodies) that bind to one or more of the orthopoxvirus family members, and other bioactive and organic chemical agents, etc.

As used herein, the term "retrovirus infection" describes a disease state, in which a retrovirus invades a healthy host cell, uses the cell's reproductive machinery to multiply or replicate, integrates its viral genome into the host cell genome, and ultimately lyses the cell, resulting in cell death, release of viral particles and the infection of other cells by the newly produced progeny viruses. Latent infection by retroviruses is also a possible result of viral infection.

Examples of retrovirus infections that can be inhibited or treated using the compositions and methods described herein include, but are not limited to, bovine lentiviruses (e.g., bovine immunodeficiency virus, Jembrana disease virus), equine lentiviruses (e.g., equine infectious anemia virus), feline lentiviruses (e.g., feline immunodeficiency virus), ovine/caprine lentivirus (e.g., caprine arthritis-encephalitis virus, ovine lentivirus, visna virus) and primate lentiviruses, such as, human immunodeficiency virus (HIV), including human immunodeficiency virus type 1 (HIV-1), human immunodeficiency virus type 2 (HIV-2), human immunodeficiency virus type 3 (HIV-3), simian AIDS retrovirus SRV-1, including human T-cell lymphotropic virus type 4 (HIV-4) and simian immunodeficiency virus (SIV), Rous sarcoma virus, avian leukosis virus, and avian myeloblastosis virus, Avian carcinoma Mill Hill virus 2, Avian myelocytomatosis virus 29, Avian sarcoma virus CT10, Fujinami sarcoma virus, UR2 sarcoma virus, Y73 sarcoma virus, Jaagsiekte sheep retrovirus, Langur virus, Mason-Pfizer monkey virus, Squirrel monkey retrovirus, mouse mammary tumour virus, murine leukemia virus, feline leukemia virus, feline sarcoma virus, Gibbon ape leukemia virus, Guinea pig type-C oncovirus, Porcine type-C oncovirus, Finkel-Biskis-Jinkins murine sarcoma virus, Gardner-Arnstein feline sarcoma virus, Hardy-Zuckerman feline sarcoma virus, Harvey murine sarcoma virus, Kirsten murine sarcoma virus, Moloney murine sarcoma virus, Snyder-Theilen feline sarcoma virus, Woolly monkey sarcoma virus, avian reticuloendotheliosis viruses, including, but not limited to, Chick syncytial virus, Reticuloendotheliosis virus, and Trager duck spleen necrosis virus, bovine leukemia virus and Human T-lymphotropic virus.

As used herein, the phrase "treating or inhibiting a retrovirus infection" means to inhibit the replication of the particular retrovirus, and/or to inhibit retrovirus transmission, and/or to prevent the retrovirus from establishing itself in its host and/or to prevent the retroviral genome from integrating into the host cell genome, and/or to ameliorate or alleviate the symptoms of the disease caused by the retrovirus infection, or any combination thereof. The treatment is considered therapeutic if there is a reduction in viral load, viral replication, viral genomic integration, viral counts, decrease in mortality, and/or morbidity.

As used herein, "alleviating a symptom of a retrovirus infection" is ameliorating or reducing any condition or symptom associated with the infection. As compared with an equivalent untreated control, such reduction or degree of prevention is at least 5%, at least 10%, at least 20%, at least 30%, at least 40%, at least 50%, at least 60%, at least 70%, at least 80%, at least 90%, at least 95%, at least 98%, at least 99%, or more, as measured by any standard technique. Ideally, the infection is completely cleared, or undetectable, as measured by any standard method known in the art.

As used herein, the term "therapeutically effective amount" of a small molecule pyridomyrimidone viral inhibitor of Formula (I) described herein, refers to the minimum amount necessary to, for example, increase the time of survival, to inhibit or prevent viral gene expression, viral replication, viral genomic integration, viral transmission, to treat or prevent the occurrence or recurrence of a viral infection, ameliorate the symptoms of theviral infection, slow the course of disease progression resulting from the viral infection, slow or inhibit a symptom of the viral infection, slow or inhibit the establishment of secondary symptoms of the viral infection, and/or inhibit the development of a secondary symptom of a viral infection.

An effective amount, as used herein, also includes an amount sufficient to delay the development of a symptom of the viral infection, alter the course of the viral infection, for example, but not limited to, slow the progression of a symptom of the viral infection, or reverse a symptom of the viral infection. Thus, it is not possible to specify the exact "effective amount." However, for any given case, an appropriate "effective amount" can be determined by one of ordinary skill in the art using only routine experimentation.

As used herein, the term "retroviral therapy" or "retroviral therapeutic agent" refers to a therapy known to be useful in treating a retroviral infection, such as an anti-HIV agent or anti-HIV therapeutic agent.

As used herein, an "anti-HIV agent" is any agent which is directly or indirectly effective in the inhibition of HIV integrase or another enzyme required for HIV replication or infection, the treatment or prophylaxis of HIV infection, and/or the treatment, prophylaxis or delay in the onset of AIDS. Suitable HIV antivirals for use in combination with the compounds described herein for antiretroviral therapy can include, but are not limited to, HAART, protease inhibitors, fusion inhibitors, integrase inhibitors, co-receptor specific agents, 3TC, AZT, nevirapine, non-nucleoside analogue reverse transcriptase inhibitors and nucleoside analogue reverse transcriptase inhibitors. HAART can be three or more antiretroviral drugs in combination, including as examples regimens that have at least one protease inhibitor, or at least a reverse transcriptase inhibitor and a protease inhibitor; or at least two reverse transcriptase inhibitors with at least one protease inhibitor.

The term "screening assays" as used herein refer to the use of assays comprising test agents, cells, reporter viruses, and tissues in the laboratory to identify agents with a specific function, e.g., an inhibitor of orthopoxviruses.

As used herein, the terms "test compound" or "test agent" refer to compounds or agents and/or compositions of the same that are to be screened for their ability to modulate (e.g., inhibit or increase) virus activity, including, but not limited to, viral gene expression, viral replication, viral infectivity, etc.

As used herein, "reporter viruses" refer to replication-competent, engineered viruses that express reporter molecules operably linked to or under control of viral temporally regulated promoter elements. By expressing one or more reporter molecules under the control of early viral promoters, intermediate viral promoters, or late viral promoters, the stage of viral life cycle can be determined based on the reporter molecule being expressed.

As used herein, a "reporter molecule" refer to a protein or molecule that can be used to produce a measurable signal such as fluorescence, color, or luminescence. Reporter protein coding sequences encode proteins whose presence in a cell or organism is readily observed. For example, fluorescent proteins cause a cell to fluoresce when excited with light of a particular wavelength, luciferases cause a cell to catalyze a reaction that produces light, and enzymes such as β-galactosidase convert a substrate to a colored product.

The term "screening" as used herein refers to the use of agents, cells, and tissues in the laboratory, and assays and methods thereof, to identify agents with a specific function, e.g., an inhibitor of poxviruses. In some embodiments, described herein are screening assays and methods to identify agents (e.g., small molecule compounds or drugs) that inhibit or otherwise modulate poxvirus activity, infectivity, or replication.

As used herein, the terms "early viral genes," "intermediate viral genes," and "late viral genes," refer to the specific windows of temporal expression in which viral genes are expressed during the life cycle of some viruses, such as orthopoxviruses. Early viral genes, intermediate viral genes, and late viral genes, are operably linked to, regulated by, or under control of "early viral promoters," "intermediate viral promoters," or "late viral promoters," respectively.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." The term "about" when used in connection with percentages can mean±1%.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006. Definitions of common terms in molecular biology are found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.) and Current Protocols in Immunology (CPI) (John E. Coligan, et. al., ed. John Wiley and Sons, Inc.), which are all incorporated by reference herein in their entireties.

It is understood that the following detailed description and following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

BRIEF DESCRIPTION OF THE DRAWINGS

FIG. 1A shows a summary of an exemplary screening protocol. Confluent A549 cells were infected with a high MOI of fluorescence reporter vaccinia virus. A diversity-oriented synthesis library was screened for compounds that reduced reporter expression at 12 h postinfection. FIG. 1B demonstrates structure and synthesis of CMLDBU6 128, identified from this screen.

FIG. 3E shows microscopy of A549 cells after high MOI infection with TrpV reporter virus, which contains early Venus, intermediate Chemy, and late TagBFP in a single virus Uninfected and 12 h postinfection DMSO- or CMLDBU6 128-treated infections are shown.

FIG. 6B shows single-cycle growth curves on A549 cells of four plaque-purified viruses, two from pool DR1 (DR1a and DR1b) and two from pool DR2 (DR2b and DR2c). FIG. 6C demonstrates coding changes identified by whole genome sequencing. DR1a and DR1b had an identical V576G mutation, and DR2b and DR2c had an identical J6R A954V mutation. FIG. 6D shows single-cycle growth curves in A549 cells using monkeypox Zaire 1979 (MPDX), cowpox wildtype (CPX), and vaccinia IHDJ (VV).

FIG. 7A depicts a chemical structure of the (R)-enantiomer (R)-CMLDBU6 128 (left) and Nevirapine (right). FIG. 7B is a computationally generated overlay of (R)-CMLDBU6128 and nevirapine. Overlay was generated using the OPENEYE SCIENTIFIC SOFTWARE shape similarity comparison program ROCS.

DETAILED DESCRIPTION

Figure 1C:
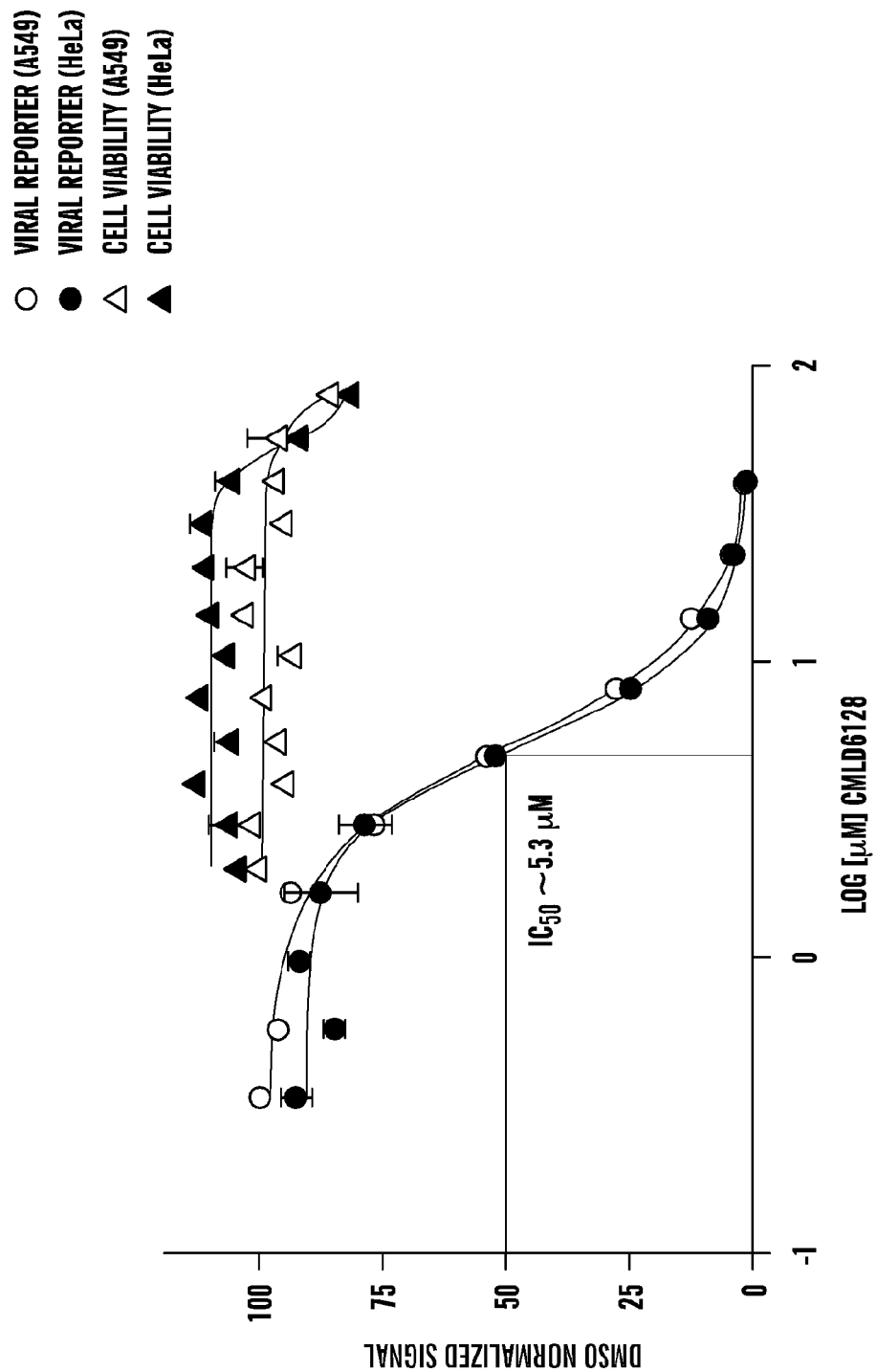
FIG. 1C shows late viral reporter expression from high MOI infections of A549 and HeLa cells (12 h postinfection), and cell cytotoxicity determination (24 h) over a dose range of CMLDBU6128.

Provided herein are novel pharmaceutical compositions and methods thereof comprising agents that act as viral inhibitors, and assays and methods for screening of the same. The inventors have discovered novel small molecule pyridomyrimidone viral inhibitor agents of Formula (I), as described herein, such as 4-acetyl-2,3,7,8-tetrahydro-3-phenylpyrido[1,2-f]pyrimidin-1-one, termed herein as "CMLDBU6128," and methods comprising such inhibitor agents of Formula (I) for use in inhibiting viral replication, such as HIV, and treating viral infections, such as orthopox virus infections and retroviral infections. Methods of synthesizing such agents are also provided herein. As shown herein, these pyridomyrimidone inhibitor agents have broad spectrum activity against the orthopoxvirus genus, and represent the first non-nucleoside analog small molecule orthopoxvirus inhibitors. Also, as demonstrated herein, these pyridomyrimidone inhibitor agents surprisingly have inhibitor activity against HIV replication. Thus, the inventors have shown that the compounds described herein are effective inhibitors of both orthopoxviruses and retroviruses, such as lentiviruses, including HIV. The pyridomyrimidone inhibitors of Formula I, such as CMLDBU6128, persistently inhibit viral replication following peak drug exposure/dosage, and continue to mediate effects to some degree even after discontinuation of administration of the inhibitors. Accordingly, the therapeutic compositions comprising the molecule pyridomyrimidone inhibitor agents of Formula (I), such as 4-acetyl-2,3,7,8-tetrahydro-3-phenylpyrido[1,2-f] pyrimidin-1-one, are useful in inhibiting viral replication, and/or the treatment and prevention of viral infections, such as orthopoxvirus infections and retroviral infections, and reducing or inhibiting transmission of orthopoxvirus and/or retroviral diseases.

Also provided herein are novel screening assays and methods for the identification and characterization of viral inhibitor agents. These assays and methods are based, in part, on the use of "reporter viruses," which comprise genetic elements that have been engineered to express reporter molecules, such that the viruses express the reporter molecules at specific stages of the viral replication cycle, thus allowing real-time monitoring of anti-viral activity. By using these reporter viruses in high-throughput screening assays, as described herein, novel viral inhibitor agents can be identified and characterized.

Viruses & Viral Inhibitors

Described herein are novel therapeutic compositions comprising small molecule pyridomyrimidone inhibitor agents of Formula (I) and methods thereof for inhibiting and treating viral replication and/or viral infection using the therapeutic compositions described herein. Some non-limiting examples of infectious viruses include: Poxyiridae (variola viruses, vaccinia viruses, pox viruses); Retroviridae; Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), herpes viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses). The compositions and methods described herein are contemplated for use in treating infections with these viral agents.

Orthopoxviruses

In some aspects, the virus being targeted or inhibited by the therapeutic compositions and/or methods described herein is an orthopox virus. The Orthopox genus (Orthopoxyiridae) is a member of the Poxyiridae family of viruses which includes the Choropoxivirinae subfamily and the Entomopoxyiridae subfamily. The Chordopoxyiridae subfamily includes Orthopox genus, Parapox genus; Aviropox genus; Capripoxvirus genus; Leporipoxvirus genus; Suipoxvirus genus; Molluscipoxvirus genus and Yatapox genus. The Entomopoxyiridae subfamily includes Entomopoxviruses A, B and C. The orthopoxvirus genus comprises numerous viruses that cause significant disease in both human and animal populations.

Viruses belonging to the Orthopoxvirus genus of the Poxyiridae family, i.e., "orthopoxviruses," include, but are not limited to, Buffalopox virus; Camelpox virus; Cowpox virus; Ectromelia virus; Monkeypox virus; Rabbitpox virus; Raccoonpox virus; virus; Skunkpox virus; Taterapox virus; Uasin Gishu disease virus; Vaccinia virus; Variola virus; and Volepox virus. Diseases caused by or associated with orthopoxviruses include Buffalopox; Camelpox; Cowpox; Mousepox (caused by Ectromelia virus); Monkeypox; Rabbitpox, also known as Green Rabbit Syndrome; Raccoonpox; Sealpox; Skunkpox; Taterapox; Uasin Gishu disease; Smallpox; and Volepox.

Orthopoxviruses replicate in the cytoplasm and encode macromolecular machinery for transcription, post-transcriptional mRNA processing, and DNA genome replication[6]. Gene expression proceeds in a classical cascade mechanism that is broadly categorized into early, intermediate, and late phases[7]. Viral replication occurs in perinuclear viral factories and a major mode of transmission of these predominantly intracellular viruses is to adjacent cells via trafficking to the cell membrane or upon infected cell rupture[8]. While these core viral functions are conserved across orthopoxviruses, host-range and virulence factors are divergent[9][10] The lifecycle of poxviruses is complicated by having multiple infectious forms, with differing mechanisms of cell entry. Poxviruses are unique among DNA viruses in that they replicate in the cytoplasm of the cell rather than in the nucleus. In order to replicate, poxviruses produce a variety of specialized proteins not produced by other DNA viruses, the most important of which is a viral-associated DNA-dependent RNA polymerase. Both enveloped and unenveloped virions are infectious. The viral envelope is made of modified Golgi membranes containing viral-specific polypeptides, including hemagglutinin.

Variola virus, the causative agent of smallpox, is highly transmissible and causes severe disease in humans resulting in high mortality rates (Henderson et al. (1999) JAMA. 281:2127-2137). Due to global eradication of smallpox by vaccination, the smallpox vaccine program was terminated in 1972; thus, many individuals are no longer immune to smallpox infection. Even vaccinated individuals may no longer be fully protected, especially against highly virulent or recombinant strains of virus (Downie and McCarthy. (1958) J. Hyg. 56:479-487; Jackson, supra). Therefore, if variola virus were reintroduced into the human population either deliberately or accidentally, mortality and morbidity would be severe.

Recent concerns over the use of smallpox virus as a biological weapon has underscored the necessity of developing small molecule therapeutics, as described herein, that target orthopoxviruses. Moreover, there is precedent for use of variola virus as a biological weapon. During the French and Indian wars (1754-1765), British soldiers distributed blankets used by smallpox patients to American Indians in order to establish epidemics (Stern, E. W. and Stern A. E. 1945. The effect of smallpox on the destiny of the Amerindian. Boston). The resulting outbreaks caused 50% mortality in some Indian tribes (Stern, E. W. and Stern A. E.). More recently, the soviet government launched a program to produce highly virulent weaponized forms of variola in aerosolized suspensions (Henderson, supra). Of further concern is the observation that recombinant forms of poxvirus have been developed that have the potential of causing disease in vaccinated animals (Jackson et al. (2001) J. Virol., 75:1205-1210).

Variola virus is naturally transmitted via aerosolized droplets to the respiratory mucosa where replication in lymph tissue produces asymptomatic infection that lasts 1-3 days. Virus is disseminated through the lymph to the skin where replication in the small dermal blood vessels and subsequent infection and lysis of adjacent epidermal cells produces skin lesions (Moss, B. (1990) Poxyiridae and Their Replication, 2079-2111. In B. N. Fields and D. M. Knipe (eds.), Fields Virology. Raven Press, Ltd., New York). Two forms of disease are associated with variola virus infection; variola major, the most common form of disease, which produces a 30% mortality rate and variola minor, which is less prevalent and rarely leads to death (<1%). Mortality is the result of disseminated intravascular coagulation, hypotension, and cardiovascular collapse, that can be exacerbated by clotting defects in the rare hemorrhagic type of smallpox (Moss, supra).

A recent outbreak of monkeypox virus further underscores the need for developing small molecule therapeutics that target viruses in the orthopox genus. Appearance of monkeypox in the US represents an emerging infection. Monkeypox and smallpox cause similar diseases in humans, however mortality for monkeypox is lower (1%).

Vaccination is the current means for preventing orthopoxvirus diseases, particularly smallpox disease. The smallpox vaccine was developed using attenuated strains of vaccinia virus that replicate locally and provide protective immunity against variola virus in greater than 95% of vaccinated individuals (Modlin (2001) MMWR (Morb Mort Wkly Rep) 50:1-25). Adverse advents associated with vaccination occur frequently (1:5000) and include generalized vaccinia and inadvertent transfer of vaccinia from the vaccination site. More serious complications such as encephalitis occur at a rate of 1:300,000, which is often fatal (Modlin, supra). The risk of adverse events is even more pronounced in immunocompromised individuals (Engler et al. (2002) J Allergy Clin Immunol. 110:357-365). Thus, vaccination is contraindicated for people with AIDS or allergic skin diseases (Engler et al.). While protective immunity lasts for many years, the antibody response to smallpox vaccination is significantly reduced 10 to 15 years post inoculation (Downie, supra). In addition, vaccination may not be protective against recombinant forms of orthopoxvirus. A recent study showed that recombinant forms of mousepox virus that express IL-4 cause death in vaccinated mice (Jackson, supra). Given the side effects associated with vaccination, contraindication of immunocompromised individuals, and inability to protect against recombinant strains of virus, better preventatives and/or new therapeutics for treatment of orthopoxvirus infection, such as smallpox virus infection, are needed.

Vaccinia virus immunoglobulin (VIG) has been used for the treatment of post-vaccination complications. VIG is an isotonic sterile solution of immunoglobulin fraction of plasma derived from individuals who received the vaccinia virus vaccine. It is used to treat eczema vaccinatum and some forms of progressive vaccinia. Since this product is available in limited quantities and difficult to obtain, it has not been indicated for use in the event of a generalized smallpox outbreak (Modlin, supra).

Cidofovir ([(S)-1-(3-hydroxy-2-phosphonylmethoxypropyl)cytosine, or VISTIDE] [HPMPC]) is a nucleoside analog approved for treatment of CMV retinitis in AIDS patients. Cidofovir has been shown to have activity in vitro against a number of DNA containing viruses including adenovirus, herpesviruses, hepadnaviruses, polyomaviruses, papillomaviruses, and orthopoxviruses (Bronson et al. (1990) Adv. Exp. Med. Biol. 278:277-83; De Clercq et al. (1987) Antiviral Res. 8:261-272; de Oliveira et al. (1996) Antiviral Res. 31:165-172; Snoeck et al. (2001) Clin Infect. Dis. 33:597-602). Cidofovir has also been found to inhibit authentic variola virus replication (Smee et al. (2002) Antimicrob. Agents Chemother. 46:1329-1335).

However, cidofovir administration is associated with a number of issues. Cidofovir is poorly bioavailable and must be administered intravenously (Lalezari et al. (1997) Ann. Intern. Med. 126:257-263). Moreover, cidofovir produces dose-limiting nephrotoxicity upon intravenous administration (Lalezari et al.). In addition, cidofovir-resistance has been noted for multiple viruses. Cidofovir-resistant cowpox, monkeypox, vaccinia, and camelpox virus variants have been isolated in the laboratory by repeated passage in the presence of drug (Smee, supra). Cidofovir-resistance represents a significant limitation for use of this compound to treat orthopoxvirus replication. Thus, the poor bioavailability, need for intravenous administration, and prevalence of resistant virus is an issue with existing therapies to treat orthopoxvirus infection.

In addition to viral polymerase inhibitors such as cidofovir, a number of other compounds have been reported to inhibit orthopoxvirus replication (De Clercq. (2001) Clin Microbiol. Rev. 14:382-397). Historically, methisazone, the prototypical thiosemicarbazone, has been used in the prophylactic treatment of smallpox infections (Bauer et al. (1969) Am. J. Epidemiol. 90:130-145). However, this compound class has not garnered much attention since the eradication of smallpox, due to generally unacceptable side effects such as severe nausea and vomiting. Mechanism of action studies suggest that methisazone interferes with translation of L genes (De Clercq (2001), supra). Like cidofovir, methisazone is a relatively non-specific antiviral compound and can inhibit a number of other viruses including adenoviruses, picornaviruses, reoviruses, arboviruses, and myxoviruses (Id.).

Another class of compounds that has been described as useful for the treatment of poxviruses is represented by inhibitors of S-adenosylhomocysteine hydrolase (SAH). This enzyme is responsible for the conversion of S-adenosylhomocysteine to adenosine and homocysteine, a necessary step in the methylation and maturation of viral mRNA.

Inhibitors of this enzyme have shown efficacy at inhibiting vaccinia virus in vitro and in vivo (De Clercq et al. (1998) Nucleosides Nucleotides. 17:625-634.).

Structurally, all active small molecule inhibitors reported to date are analogs of the nucleoside adenosine. Many are carbocyclic derivatives, exemplified by Neplanacin A and 3-Deazaneplanacin A. While these compounds have shown some efficacy in animal models, like many nucleoside analogues, they suffer from general toxicity and/or poor pharmacokinetic properties (Coulombe et al. (1995) Eur. J. Drug Metab Pharmacokinet 20:197-202; Obara et al. (1996) J. Med. Chem. 39:3847-3852). It is unlikely that these compounds can be administered orally, and it is currently unclear whether they can act prophylactically against smallpox infections.

Retroviruses

In some aspects, the virus being targeted or inhibited by the therapeutic compositions and/or methods described herein is a retrovirus. Retroviruses are maintained as proviral DNAs that are integrated into the genome of somatic cells. Mammalian cells have evolved mechanisms to limit or restrict retroviral replication, and retroviruses, in turn, have evolved mechanisms to inactivate or overcome such blocks to infection (D. Wolf and S. P. Goff, 2008, Ann. Rev. Gen., 42: 143-163).

Integration into the genome of the host cell is a defining feature of retroviral replication. Once integrated, the retroviral DNA is replicated along with cellular DNA during each cycle of cell division. The retroviral DNA is synthesized by reverse transcription of the retroviral RNA genome that enters the host cell upon infection. Reverse transcription takes place in the reverse transcription complex (RTC), a nucleoprotein complex that is derived from the core of the infecting virion. The synthesis of full-length retroviral DNA in the RTC produces a large nucleoprotein complex termed the pre-integration complex (PIC). The newly synthesized retroviral DNA remains associated with viral and cellular proteins the (PIC). The viral integrase protein that integrates retroviral DNA into the host genome is one of the key components of the PIC. As reverse transcription occurs in the cytoplasm, the PIC must be transported to the nuclear periphery and cross the nuclear envelope before integration of the viral DNA into the host chromosome. (Y. Suzuki and R. Craigie, 2007, Nat Rev Microbiol, 5:187-196). Once the retroviral nucleoprotein complex reaches the nucleus it must cross the nuclear envelope to integrate into the chromosomal DNA.

Any retrovirus can be a target of the methods and therapeutic compositions described herein. Thus, a "retrovirus," as used herein, refers to any enveloped RNA virus, belonging to the viral family Retroviridae, that replicates in a host cell via the enzyme reverse transcriptase to produce DNA from its RNA genome. The retroviral DNA is then incorporated into the host's genome by an integrase enzyme. The retrovirus thereafter replicates as part of the host cell's DNA. The retrovirus itself stores its nucleic acid, in the form of a +mRNA (including the 5' cap and 3'PolyA inside the virion) genome and serves as a means of delivery of that genome into cells it targets as an obligate parasite, and constitutes the infection. As used herein, a "provirus" refers to retroviral DNA once it is integrated into the genome of a host cell. Retrovirus genomes commonly include, but are not limited to, three open reading frames that encode for proteins that can be found in the mature virus: group-specific antigen (gag) encoding for core and structural proteins of the virus; polymerase (pol) coding for reverse transcriptase, protease and integrase; and envelope (env) coding for the retroviral coat proteins.

The genera belonging to the family of Retroviridae include, but are not limited to:

Alpharetrovirus: Members of "Alpharetrovirus" have a type C morphology, and can cause sarcomas, other tumors, and anaemia of wild and domestic birds and also affect rats. Alpharetrovirus species include, but are not limited to, the Rous sarcoma virus, avian leukosis virus, and avian myeloblastosis virus. Rous sarcoma virus, Avian carcinoma Mill Hill virus 2, Avian myelocytomatosis virus 29, Avian sarcoma virus CT10, Fujinami sarcoma virus, UR2 sarcoma virus, and the Y73 sarcoma virus.

Betaretrovirus: Members of "Betaretrovirus" have a type B or type C morphology. The type B is common for a few exogenous, vertically transmitted and endogenous viruses of mice, while some primate and sheep viruses are type D. Betaretrovirus species include, but are not limited to, Jaagsiekte sheep retrovirus, Langur virus, Mason-Pfizer monkey virus, Squirrel monkey retrovirus, and mouse mammary tumour virus.

Gammaretrovirus: Members of "Gammaretrovirus" often contain oncogenes and cause sarcomas and leukemias. Gammaretrovirus species include, but are not limited to, the murine leukemia virus, the feline leukemia virus, the feline sarcoma virus, Gibbon ape leukemia virus, Guinea pig type-C oncovirus, Porcine type-C oncovirus, Finkel-Biskis-Jinkins murine sarcoma virus, Gardner-Arnstein feline sarcoma virus, Hardy-Zuckerman feline sarcoma virus, Harvey murine sarcoma virus, Kirsten murine sarcoma virus, Moloney murine sarcoma virus, Snyder-Theilen feline sarcoma virus, Woolly monkey sarcoma virus, and the avian reticuloendotheliosis viruses, including, but not limited to, Chick syncytial virus, Reticuloendotheliosis virus, and Trager duck spleen necrosis virus. Many endogenous retroviruses, closely related to exogenous gammaretroviruses are present in the DNA of mammals (including humans), birds, reptiles and amphibians.

Deltaretrovirus: The "Deltaretrovirus" genus consists of exogenous horizontally-transmitted viruses found in several groups of mammals. Examples include, but are not limited to, the bovine leukemia virus and the Human T-lymphotropic virus.

Lentiviruses: "Lentiviruses", as defined herein, are a genus of retroviruses that includes bovine lentiviruses (e.g., bovine immunodeficiency virus, Jembrana disease virus), equine lentiviruses (e.g. equine infectious anemia virus), feline lentiviruses (e.g. feline immunodeficiency virus), ovine/caprine lentivirus (e.g. caprine arthritis-encephalitis virus, ovine lentivirus, visna virus) and primate lentivirus group. The primate lentivirus group includes human immunodeficiency virus (HIV), including human immunodeficiency virus type 1 (HIV-1), human immunodeficiency virus type 2 (HIV-2), and human immunodeficiency virus type 3 (HIV-3), as well as simian AIDS retrovirus SRV-1, including human T-cell lymphotropic virus type 4 (HIV-4) and simian immunodeficiency virus (SIV). The env genes of HIV-1, HIV-2 and SIV all produce an envelope glycoprotein, which is cleaved, with one portion being an exterior viral envelope protein subunit referred to as gp120. The binding and fusion of HIV-1, HIV-2 and SIV viruses with cells is mediated by specific interaction between the external subunit of this gp120 viral envelope protein and the CD4 receptor on the target cell surface (Dalgleish, et al., Nature, 312:763-767 (1984); Klatzmann, et al., Nature, 312:767-768 (1984); Berger, et al., PNAS, 85:2357-2361 (1988)).

Pyridomyrimidone Viral Inhibitor Agents

As described herein, the inventors have discovered that the small molecule pyridomyrimidone inhibitor agents of Formula (I), such as 4-acetyl-2,3,7,8-tetrahydro-3-phenylpyrido[1,2-f]pyrimidin-1-one or CMLDBU6128, have broad-spectrum inhibitory activity on orthopoxvirus family members, and inhibit post-replicative viral intermediate and late gene expression. They have also demonstrated that the small molecule pyridomyrimidone inhibitor agents of Formula (I), such as 4-acetyl-2,3,7,8-tetrahydro-3-phenylpyrido[1,2-f]pyrimidin-1-one (CMLDBU6128), have unexpected inhibitory effects on HIV, a member of the lentiviral genus of retroviruses. Further, they have discovered that such pyridomyrimidone inhibitor agents and compounds can be identified by novel screening assays and methods comprising, in part, reporter viruses, as the term is used herein.

Accordingly, described herein are novel small molecule pyridomyrimidone inhibitor agents for use in therapeutic compositions for, and methods of, treating and inhibiting viral gene expression, infection, and transmission. In some embodiments of these aspects, the pyridomyrimidone inhibitor agents are used as orthopoxvirus inhibitors or inhibitors of orthopoxviruses. In other embodiments of these aspects, the pyridomyrimidone inhibitor agents are used as retrovirus inhibitors or inhibitors of retroviruses. In some such embodiments, the retrovirus is a lentivirus, such as HIV.

An "orthopoxvirus inhibitor" or "inhibitor of orthopoxviruses," as the terms are used herein, refer to an agent, such as a small molecule of Formula (I), that inhibits or causes or facilitates a qualitative or quantitative inhibition, decrease, or reduction in one or more processes, mechanisms, effects, responses, functions, activities or pathways mediated by an orthopoxvirus. Such changes mediated by an orthopoxvirus inhibitor, can refer to a decrease in the expression, activity or function of the viral genes expressed by an orthopoxvirus, and/or can refer to a decrease in, inhibition of, or diversion of, orthopoxvirus activity, infectivity, or replication, or any combination thereof. In some embodiments, the term orthopoxvirus inhibitor refers to an agent that inhibits or blocks expression of one or more orthopoxvirus genes, such as intermediate or late viral genes, or an agent that partially or totally blocks or arrests viral protein synthesis, viral assembly, viral infectivity, viral DNA replication, viral polymerase activity or function, or any combination thereof.

A "retrovirus inhibitor" or "inhibitor of retroviruses," as the terms are used herein, refer to an agent, such as a small molecule of Formula (I), e.g., CMLDBU6128, that inhibits or causes or facilitates a qualitative or quantitative inhibition, decrease, or reduction in one or more processes, mechanisms, effects, responses, functions, activities or pathways mediated by a retrovirus. Such changes mediated by an retrovirus inhibitor, can refer to a decrease in the expression, activity or function of the viral genes expressed by the retrovirus, and/or can refer to a decrease in, inhibition of, or diversion of, orthopoxvirus activity, infectivity, or replication, or any combination thereof. In some embodiments, the term retrovirus inhibitor refers to an agent that inhibits or blocks expression of one or more retrovirus genes, such as gag, pol, and/or env genes/open reading frames, or an agent that partially or totally blocks or arrests viral protein synthesis, viral assembly, viral infectivity, viral DNA replication, viral DNA integration, viral polymerase activity or function, viral integrase activity or function, viral reverse transcriptase activity or function, and/or any combination thereof.

As used herein, the term "expression," refers to the processes involved in producing RNA and proteins and as appropriate, secreting proteins, including where applicable, but not limited to, for example, transcription, translation, folding, modification and processing. "Expression products" include RNA or DNA transcribed from a viral gene and polypeptides obtained by translation of mRNA transcribed from a viral gene.

The invention provides, in some aspects, compositions comprising a small molecule of Formula (I) for use in a variety of applications, such as in vitro inhibition of viral replication, for example, in commercial sanitizing or cleaning products, e.g., hand sanitizers. In some aspects of the compositions and methods described herein, an orthopoxvirus inhibitor or retrovirus inhibitor is a pyridomyrimidone viral inhibitor agent of Formula (I), such as 4-acetyl-2,3,7,8-tetrahydro-3-phenylpyrido[1,2-f]pyrimidin-1-one (CMLDBU6128), having the chemical structures described herein.

The terms "inhibit," "decrease," and "reduce," are all used herein generally to mean a decrease by a statistically significant amount. Accordingly, in those embodiments of the aspects described herein related to orthopoxviruses, orthopoxvirus inhibition is achieved when the expression of one or more orthopoxvirus genes, such as intermediate or late viral genes, viral protein synthesis, viral assembly, viral infectivity, viral DNA replication, viral polymerase activity or function, or any combination thereof, is about at least 10% less, at least 20% less, at least 30% less, at least 40% less, at least 50% less, at least 60% less, at least 70% less, at least 80% less, at least 90% less, at least 95% less, at least 98% less, at least 99% less, or more, i.e., absent, or undetectable, in comparison to a reference or control level in the absence of the orthopoxvirus inhibitor. In some embodiments of the aspects described herein, the orthopoxvirus inhibitors inhibit expression of one or more orthopoxvirus intermediate or late genes.

Similarly, in those embodiments of the aspects described herein related to retroviruses, retrovirus inhibition is achieved when the expression of one or more retrovirus genes, such as the three open reading frames that encode for group-specific antigen (gag), encoding for core and structural proteins of the virus; polymerase (pol) coding for reverse transcriptase, protease and integrase; and envelope (env) coding for the retroviral coat proteins, viral protein synthesis, viral assembly, viral infectivity, viral DNA replication, viral polymerase activity or function, viral integrase activity or function, viral reverse transcriptase activity or function, or any combination thereof, is about at least 10% less, at least 20% less, at least 30% less, at least 40% less, at least 50% less, at least 60% less, at least 70% less, at least 80% less, at least 90% less, at least 95% less, at least 98% less, at least 99% less, or more, i.e., absent, or undetectable, in comparison to a reference or control level in the absence of the retrovirus inhibitor.

The term "agent," as used herein in reference to a viral inhibitor, means any compound or substance such as, but not limited to, a small molecule, nucleic acid, polypeptide, peptide, drug, ion, etc. An "agent" can be any chemical, entity, or moiety, including, without limitation, synthetic and naturally-occurring proteinaceous and non-proteinaceous entities. In some embodiments, an agent is a nucleic acid, a nucleic acid analogue, a protein, an antibody, a peptide, an aptamer, an oligomer of nucleic acids, an amino acid, or a carbohydrate, and includes, without limitation, proteins, oligonucleotides, ribozymes, DNAzymes, glycoproteins, siRNAs, lipoproteins, aptamers, and modifications and combinations thereof etc. In certain embodiments, as described herein, agents are small molecules having a chemical moiety. For example, chemical moieties include unsubstituted or substituted alkyl, aromatic, or heterocyclyl moieties. Compounds can be known to have a desired activity and/or property, e.g., inhibit viral replication, or viral gene expression, or can be selected from a library of diverse compounds, using, for example, the screening methods described herein.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

In some embodiments of the aspects described herein, an orthopoxvirus inhibitor is identified as a small molecule compound that inhibits or blocks expression of one or more orthopoxvirus genes, such as early, intermediate, or late viral genes, or a small molecule compound that partially or totally blocks or arrests viral protein synthesis, viral assembly, viral infectivity, viral DNA replication, viral polymerase activity or function, or any combination thereof, as measured or assayed using any method known to one of skill in the art; and preferably inhibits orthopoxvirus growth or replication or orthopoxvirus infectivity, as measured using any assay known to one of skill in the art. Several orthopoxviruses, including cowpox, monkeypox, camelpox, variola, and other mammalian orthopoxviruses, can, for example, be grown readily in cell culture and produce robust cytopathic effect (CPE) in 3 to 5 days. Since this CPE is directly related to viral replication, compounds that inhibit virus replication in cell culture can be identified readily as conferring protection from virus-induced CPE. Moreover, compounds having identified activity against, for example, can also be tested for activity against human variola virus given the high degree of homology (>95%) between these two viruses and as the replication proteins of orthopoxviruses are highly homologous. Inhibition of expression of one or more orthopoxvirus genes can be measured using, for example, any of the in vitro screening assays comprising reporter viruses as described herein.

As used herein, the terms "early viral genes," "intermediate viral genes," and "late viral genes," refer to the specific windows of temporal expression in which viral genes are expressed during the life cycle of orthopoxviruses. Accordingly, early viral genes, intermediate viral genes, and late viral genes, are operably linked to, regulated by, or under control of "early viral promoters," "intermediate viral promoters," or "late viral promoters," respectively. An exemplary early virus promoter is C11R. An exemplary intermediate virus promoter is G8R. An exemplary late virus promoter is F17R. Orthopoxviruses attach to glycosaminoglycans (GAGs) on the surface of a target cell or by components of the extracellular matrix, triggering membrane fusion and release of the virus core into the cytoplasm. Upon release of the virus core into the host cell cytoplasm, genes termed "early viral genes" are transcribed in the cytoplasm by viral RNA polymerase. Approximately 50% of viral genes are expressed using virally encoded and encapsulated transcriptional machinery, which includes multisubunit RNA polymerase, an RNA pol accessory protein, an early transcription factor, a capping enzyme and cap modification enzyme, termination and transcript release proteins, and poly A polymerase. Early expression begins at 30 minutes post-infection. The viral core is completely uncoated as early gene expression ends, and the viral genome is now free in the cytoplasm.

Intermediate viral genes are expressed after early viral gene expression ends, and utilize both viral transcription factors and host transcription factors for their expression, and trigger genomic DNA replication at approximately 100 minutes post-infection. Viral genomic DNA becomes nicked and replication occurs through strand displacement synthesis with formation of genome concatemers.

Late viral genes are expressed from 140 min to 48 hours post-infection, and produce all structural proteins. Assembly of progeny virions starts in association with internal membranes of the infected cell, producing an spherical immature particle. This virus particle matures into brick-shaped intracellular mature virion (IMV). IMV virion can be released upon cell lysis, or can acquire a second double membrane from trans-Golgi and bud as external enveloped virion (EEV). In some embodiments of the aspects described herein, an orthopoxvirus inhibitor is identified as a small molecule compound that inhibits or blocks expression of one or more orthopoxvirus intermediate or late viral genes.

In some embodiments of the aspects described herein, a retrovirus inhibitor is identified as a small molecule compound that inhibits or blocks expression of one or more retrovirus genes or open reading frames, such as the pol, gag, and/or env genes, or a small molecule compound that partially or totally blocks or arrests viral protein synthesis, viral assembly, viral infectivity, viral DNA replication, viral reverse transcription, viral DNA integration, viral reverse transcriptase activity or function, viral integrase activity or function, viral polymerase activity or function, or any combination thereof, as measured or assayed using any method known to one of skill in the art; and preferably inhibits retrovirus growth or replication, or retrovirus infectivity, as measured using any assay known to one of skill in the art. Infectivity of several retroviruses, including HIV, SIV, and SHIV, can be assayed for using TZM-bl cells, for example. This assay measures viral production in TZM-bl cells as a function of a reduction in Tat-induced luciferase (Luc) reporter gene expression in the presence of a potential inhibitor agent relative to corresponding samples without the inhibitor agent after a single round of virus infection. TZM-bl cells (also called JC57BL-13) can be obtained from the NIH AIDS Research and Reference Reagent Program. These cells are derived from a HeLa cell clone that was engineered to express CD4 and CCR5 [1] and contains integrated reporter genes for firefly luciferase and *E. coli* β-galactosidase under control of an HIV-1 LTR [2], permitting sensitive and accurate measurements of infection. The cells are highly permissive to infection by most strains of HIV, SIV and SHIV, including primary HIV-1 isolates and molecularly cloned Env-pseudotyped viruses. Expression of the reporter genes is induced in trans by viral Tat protein soon after infection. Luciferase activity is quantified in this assay by luminescence and is directly proportional to the number of infectious virus particles present in the initial inoculum. The assay can be performed. For example, in 96-well culture plates for high throughput capacity, and use of a clonal cell population provides enhanced precision and uniformity.

Pyridomyrimidone Viral Inhibitor Agents Accordingly, provided for use in the various aspects described herein are novel small molecule pyridomyrimidone inhibitor agents of Formula (I):

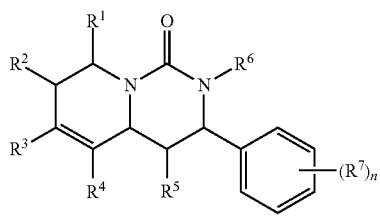

FORMULA (I)

wherein:

$R^1$, $R^2$ and $R^4$ are independently, H, alkyl, alkenyl, alkynyl, aryl, heteroaryl, cyclyl, heterocyclyl, acyl, amino, hydroxyl, alkoxy, $C(O)OR^8$, or $C(O)N(R^8)_2$, each of which can be optionally substituted;

$R^3$ is H, alkyl, alkenyl, alkynyl, aryl, heteroaryl, cyclyl, heterocyclyl, acyl, amino, or alkyl silane (e.g., trialkylsilane), each of which can be optionally substituted;

$R^5$ is H, alkyl, alkenyl, alkynyl, aryl, heteroaryl, cyclyl, heterocyclyl, acyl, amino, hydroxyl, alkoxy, mercapato, thioalkoxy, sulfinyl, sulfonyl, $C(O)OR^8$, or $C(O)N(R^8)_2$, each of which can be optionally substituted;

$R^6$ is H, alkyl, alkenyl, alkynyl, aryl, heteroaryl, cyclyl, heterocyclyl, or acyl, each of which can be optionally substituted;

$R^7$ is independently for each occurrence H, halo, cyano, amino, nitro, hydroxyl, mercapto, thioalkoxy, sulfinyl, sulfonyl, alkyl, alkenyl, alkynyl, alkoxy, acyl, aryl, heteroaryl, cyclyl, heterocyclyl, $C(O)OR^8$, or $C(O)N(R^8)_2$, each of which can be optionally substituted;

$R^8$ is H, alkyl, alkenyl, alkynyl, aryl, heteroaryl, cyclyl, or heterocyclyl, each of which can be optionally substituted;

n is 0, 1, 2, 3, 4, or 5; and pharmaceutically acceptable salts thereof.

In some embodiments of this aspect and all such aspects described herein, a compound of formula (I) is 4-acetyl-2,3,7,8-tetrahydro-3-phenylpyrido[1,2-f]pyrimidin-1-one, also referred to herein as CMLDBU6128, having the chemical structure:

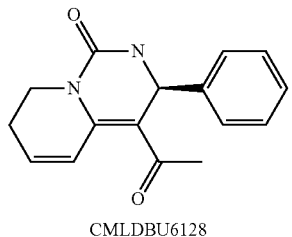 [SMILES: CC(=O)C1=C2C=CCCN2C(=O)N[C@H]1c1ccccc1]

CMLDBU6128

For simplicity, chemical moieties are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms "alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The term "halo" or "halo" refers to any radical of fluorine, chlorine, bromine or iodine.

The term "acyl" refers to an alkylcarbonyl, cycloalkylcarbonyl, arylcarbonyl, heterocyclylcarbonyl, or heteroarylcarbonyl substituent, any of which may be further substituted by substituents. Exemplary acyl groups include, but are not limited to, ($C_1$-$C_6$)alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions.

The term "alkyl" refers to saturated non-aromatic hydrocarbon chains that may be a straight chain or branched chain, containing the indicated number of carbon atoms (these include without limitation propyl, allyl, or propargyl), which may be optionally inserted with N, O, or S. For example, $C_1$-$C_6$ indicates that the group may have from 1 to 6 (inclusive) carbon atoms in it.

The term "alkenyl" refers to an alkyl that comprises at least one double bond. Exemplary alkenyl groups include, but are not limited to, for example, ethenyl, propenyl, butenyl, 1-methyl-2-buten-1-yl and the like.

The term "alkynyl" refers to an alkyl that comprises at least one triple bond.

The term "alkoxy" refers to an —O-alkyl radical.

The term "mercapto" refers to an —SH radical.

The term "thioalkoxy" refers to an —S-alkyl radical.

The term "sulfinyl" refers to an —S(O)-alkyl radical.

The term "sulfonyl" refers to an —$SO_2$-alkyl radical.

The term "aryl" refers to monocyclic, bicyclic, or tricyclic aromatic ring system wherein 0, 1, 2, 3, or 4 atoms of each ring may be substituted by a substituent. Exemplary aryl groups include, but are not limited to, phenyl, naphthyl, anthracenyl, azulenyl, fluorenyl, indanyl, indenyl, naphthyl, phenyl, tetrahydronaphthyl, and the like.

The term "cyclyl" or "cycloalkyl" refers to saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Exemplary cycloalkyl groups include, but are not limited to, cyclopropyl, cyclobutyl, cyclopentyl, cyclopentenyl, cyclohexyl, cyclohexenyl, cycloheptyl, cyclooctyl, and the like.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examplary heterocyclyl groups include, but are not limited to piperazinyl, pyrrolidinyl, dioxanyl, morpholinyl, tetrahydrofuranyl, and the like.

The term "optionally substituted" means that the specified group or moiety, such as an alkyl group, alkenyl group, alkynyl group, cyclyl group, heterocyclyl group, aryl group, heteroaryl group and the like, is unsubstituted or is substituted with one or more (typically 1-4 substituents) independently selected from the group of substituents listed below in the definition for "substituents" or otherwise specified.

The term "substituents" refers to a group "substituted" on an alkyl, alkenyl, alkynyl, cycloalkyl, aryl, heterocyclyl, or heteroaryl group at any atom of that group. Suitable substituents include, without limitation, halo, hydroxy, oxo, nitro, haloalkyl, alkyl, alkenyl, alkynyl, alkaryl, aryl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano or ureido. In some cases, two substituents, together with the carbons to which they are attached to can form a ring.

In many cases, protecting groups are used during preparation of the compounds described herein. As used herein, the term "protected" means that the indicated moiety has a protecting group appended thereon. In some preferred embodiments of the invention, compounds contain one or more protecting groups. A wide variety of protecting groups can be employed in the methods of the invention. In general, protecting groups render chemical functionalities inert to specific reaction conditions, and can be appended to and removed from such functionalities in a molecule without substantially damaging the remainder of the molecule.

Representative protecting groups, are disclosed in Greene and Wuts, *Protective Groups in Organic Synthesis*, Chapter 2, 2d ed., John Wiley & Sons, New York, 199. Examples of hydroxyl protecting groups include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p'-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate. Exemplary amino-protecting groups include, but are not limited to, carbamate protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl.

As used herein, the term "pharmaceutically-acceptable salts" refers to the conventional nontoxic salts or quaternary ammonium salts of therapeutic agents, e.g., from non-toxic organic or inorganic acids. These salts can be prepared in situ in the administration vehicle or the dosage form manufacturing process, or by separately reacting a therapeutic agent in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), content of which is herein incorporated by reference in its entirety.

In some embodiments of the aspects described herein, representative salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

*Pharmaceutical Compositions of Pyridomyrimidone Viral Inhibitor Agents and Therapeutic Uses*

Described herein are pharmaceutical compositions comprising small molecule pyridomyrimidone viral inhibitors of Formula (I) for use in methods of treating a subject having or at risk for developing an infection mediated by an virus, such as an orthopox virus or a retrovirus. The small molecule pyridomyrimidone viral inhibitors of Formula (I) described herein, such as 4-acetyl-2,3,7,8-tetrahydro-3-phenylpyrido[1,2-f]pyrimidin-1-one (CMLDBU6128), can be administered to a subject in need thereof by any appropriate route which results in an effective treatment in the subject.

Accordingly, in some aspects, provided herein are methods of inhibiting an orthopoxvirus infection in a subject. Such methods comprise administering to a subject having or at risk for an orthopoxvirus infection a therapeutically effective amount of a pharmaceutical composition comprising a small molecule pyridomyrimidone viral inhibitor of Formula (I) as described herein. In some embodiments of these aspects and all such aspects described herein, the pyridomyrimidone viral inhibitor of Formula (I) is 4-acetyl-2,3,7,8-tetrahydro-3-phenylpyrido[1,2-f]pyrimidin-1-one (CMLDBU6128).

By "inhibiting an orthopoxvirus infection" is meant that productive infection by an orthopoxvirus is reduced or decreased or inhibited. A "decrease" or "inhibition" in orthopoxvirus infection induced by the compositions and methods described herein may not directly inhibit the initial infection of a cell, but can inhibit, for example, the expression of viral genes, viral replication, and/or inhibit the generation of viral progeny. A "decrease" in orthopoxvirus infection can also refer then to a decrease in viral load, i.e., at least 10% lower, and preferably at least 20% lower, at least 30% lower, at least 40% lower, at least 50% lower, at least 60% lower, at least 70% lower, at least 80% lower, at least 90% lower, at least 95% lower, at least 99%, at least 99.5% lower, at least 99.9% or more, (i.e., no detectable viral load).

In other aspects, provided herein are methods of inhibiting a retrovirus infection in a subject. Such methods comprise administering to a subject having or at risk for a retrovirus infection a therapeutically effective amount of a pharmaceutical composition comprising a small molecule pyridomyrimidone viral inhibitor of Formula (I) as described herein. In some embodiments of these aspects and all such aspects described herein, the pyridomyrimidone viral inhibitor of Formula (I) is 4-acetyl-2,3,7,8-tetrahydro-3-phenylpyrido[1,2-f]pyrimidin-1-one (CMLDBU6128).

By "inhibiting a retrovirus infection" is meant that productive infection by a retrovirus is reduced or decreased or inhibited. A "decrease" or "inhibition" in retroviral infection induced by the compositions and methods described herein may not directly inhibit the initial infection of a cell, but can inhibit, for example, the proviral state and/or inhibit the generation of viral progeny. A "decrease" in retroviral infection can also refer then to a decrease in viral load, i.e., at least 10% lower, and preferably at least 20% lower, at least 30% lower, at least 40% lower, at least 50% lower, at least 60% lower, at least 70% lower, at least 80% lower, at least 90% lower, at least 95% lower, at least 99%, at least 99.5% lower, at least 99.9% or more, up to and including a 100% reduction (i.e., no viral load).

In some embodiments of these aspects, a sample or a cell from the subject infected with the retrovirus is contacted ex vivo or in vitro. In some embodiments, the cell being contacted expresses the cell-surface antigen CD4. In some embodiments, the cell expressing CD4 is a CD4 T lymphocyte. In some embodiments, the cell expressing CD4 is a macrophage.

The terms "subject" and "individual" are used interchangeably herein, and refer to an animal, for example a human, that an orthopoxvirus or retrovirus is capable of infecting, and/or a recipient of the small molecule pyridomyrimidone viral inhibitors of Formula (I) described herein, e.g., 4-acetyl-2,3,7,8-tetrahydro-3-phenylpyrido[1,2-f]pyrimidin-1-one (CMLDBU6128). For treatment of those viral infections that are specific for a specific animal, such as a human subject, the term "subject" refers to that specific animal. While some viruses are specific for only one species, other viruses can infect multiple species. The terms 'non-human animals' and 'non-human mammals' are used interchangeably herein, and include, for example, mammals such as rats, mice, rabbits, sheep, cats, dogs, cows, pigs, and non-human primates.

In some aspects, provided herein are methods of treatment of a subject having an orthopoxvirus infection, or at risk for an orthopoxvirus infection, the methods comprising administering to a subject having an orthopoxvirus infection, or at risk for an orthopoxvirus infection, a therapeutically effective amount of a pharmaceutical composition comprising a small molecule pyridomyrimidone viral inhibitor of Formula (I) described herein. In some embodiments of these aspects and all such aspects described herein, the pyridomyrimidone viral inhibitor of Formula (I) is 4-acetyl-2,3,7,8-tetrahydro-3-phenylpyrido[1,2-f]pyrimidin-1-one (CMLDBU6128).

As used herein, the term "orthopoxvirus infection" describes a disease state, in which an orthopoxvirus invades a healthy cell, uses the cell's reproductive machinery to multiply or replicate and ultimately lyse the cell resulting in cell death, release of viral particles and the infection of other cells by the newly produced progeny viruses. Latent infection by orthopoxviruses is also a possible result of viral infection.

As used herein, the term "treating or preventing orthopoxvirus infection" means to inhibit the replication of the particular orthopoxvirus, to inhibit orthopoxvirus transmission, and/or to prevent the orthopox from establishing itself in its host, and to ameliorate or alleviate the symptoms of the disease caused by the orthopoxvirus infection. The treatment is considered therapeutic if there is a reduction in viral load, viral replication, viral counts, decrease in mortality, and/or morbidity.

In some embodiments of the aspects described herein, a subject refers to a human subject having an orthopoxvirus infection, or at risk for an orthopoxvirus infection. A subject that has an orthopoxvirus infection is a subject having objectively measurable cells infected with an orthopoxvirus present in the subject's body. Subjects that have increased risk for an orthopoxvirus infection, or are at risk for an orthopoxvirus infection includes subjects with possible exposure to an orthopoxvirus, such as, for example, members of the armed or diplomatic services. In some such embodiments of the aspects described herein, the orthopoxvirus is a variola virus or monkeypox virus.

In some embodiments of the aspects described herein, the methods of treating an orthopoxvirus infection further comprise the step of selecting, diagnosing, or identifying a subject having an orthopoxvirus infection, or who is at increased risk for an orthopoxvirus infection. In such embodiments, a subject is identified as having orthopoxvirus infection by objective determination of the presence of infected cells in the subject's body by one of skill in the art. Such objective determinations can be performed through the sole or combined use of assays suitable for rapid and specific detection of orthopoxvirus infections. Preferably, such assays should be virus specific, and should allow for detection of exposure to orthopoxvirus before the active stages of the disease; for example, prior to formation of skin lesions. Such assays for use in identifying a subject as having or having had an orthopoxvirus infection include, but are not limited to, PCR-based assays that detect specific polynucleotides that are present during viral infection and replication; ELISA-based assays that detect viral antigens present or neutralizing antibodies present in a subject sample; plaque-reduction assays, which can be used to determine the serum dilution at which 50% of the infectious virus (e.g., vaccinia) is neutralized ($NT_{50}$), in addition to the monitoring of specific symptoms associated with the orthopoxvirus infection, such as, for example, presence of skin lesions.

Examples of orthopoxvirus infections that can be inhibited or treated using the compositions and methods described herein include, but are not limited to, aractuba virus, BeAn 58058 virus, buffalopox virus, camelpox virus (such as, for example, Camelpox virus 903, Camelpox virus CMG, Camelpox virus CMS, Camelpox virus CP1, Camelpox virus CP5, and Camelpox virus M-96), cantagalo orthopoxvirus, cowpox virus (such as, for example, Cowpox virus strain Hamburg-1985 and Cowpox virus strain Turkmenia-1974), Ectromelia virus (such as, for example, Belo Horizonte virus), elephantpox virus, horsepox virus, monkeypox virus (such as Monkeypox virus strain Sierra Leone 70-0266 and Monkeypox virus strain Zaire 77-0666), myxomaxvirus, rabbitpox virus (such as Rabbitpox strain Utrecht), raccoonpox virus, skunkpox virus, tanapoxvirus, taterapox virus, vaccinia virus (including, but not limited to, the following strains: strain Ankara, strain Copenhagen, strain Dairen I, strain IHD-J, strain L-IPV, strain LC 16M8, strain LC 16M0, strain Lister, strain LIVP, strain Tian Tan, strain WR 65-16, strain WR, and strain Wyeth), Variola virus (such as variola major virus and variola minor virus), and volepox virus.

In other aspects, provided herein are methods of treatment of a subject having a retrovirus infection, or at risk for a retrovirus infection, the methods comprising administering to a subject having a retrovirus infection, or at risk for a retrovirus infection, a therapeutically effective amount of a pharmaceutical composition comprising a small molecule pyridomyrimidone viral inhibitor of Formula (I) described herein, thereby decreasing retroviral infection and/or replication in the subject. Accordingly, in some embodiments, the subject having a retrovirus infection has been diagnosed with an infection with a retrovirus. In some embodiments, the retrovirus is a lentivirus. In some such embodiment, the lentivirus is HIV. In some embodiments of these aspects and all such aspects described herein, the pyridomyrimidone viral inhibitor of Formula (I) is 4-acetyl-2,3,7,8-tetrahydro-3-phenylpyrido[1,2-f]pyrimidin-1-one (CMLDBU6128).

As used herein, the term "retrovirus infection" describes a disease state, in which a retrovirus invades a healthy host cell, uses the cell's reproductive machinery to multiply or replicate, integrates its viral genome into the host cell genome, and ultimately lyses the cell, resulting in cell death, release of viral particles and the infection of other cells by the newly produced progeny viruses. Latent infection by retroviruses is also a possible result of viral infection.

As used herein, the term "treating or inhibiting a retrovirus infection" means to inhibit the replication of the particular retrovirus, and/or to inhibit retrovirus transmission, and/or to prevent the retrovirus from establishing itself in its host and/or preventing the retroviral genome from integrating into the host cell genome, and/or to ameliorate or alleviate the symptoms of the disease caused by the retrovirus infection. The treatment is considered therapeutic if there is a reduction in viral load, viral replication, viral genomic integration, viral counts, decrease in mortality, and/or morbidity.

In some embodiments of the aspects described herein, a subject refers to a human subject having a retrovirus infection, or at risk for a retrovirus infection. A subject that has a retrovirus infection is a subject having objectively measurable cells infected with an orthopoxvirus present in the subject's body. Subjects that have increased risk for a retrovirus infection, or are at risk for a retrovirus infection includes subjects with possible exposure to a retrovirus. In some such embodiments of the aspects described herein, the retrovirus is a lentivirus, such as, for example, HIV.

In some embodiments of the aspects described herein, the methods of treating a retrovirus infection further comprise the step of selecting, diagnosing, or identifying a subject having a retrovirus infection or who is at increased risk for a retrovirus infection. In such embodiments, a subject is identified as having a retrovirus infection by objective determination of the presence of infected cells in the subject's body by one of skill in the art. Such objective determinations can be performed through the sole or combined use of assays suitable for rapid and specific detection of retrovirus infections. Preferably, such assays should be virus specific, and should allow for detection of exposure to the retrovirus before the active stages of the disease; for example, prior to development of AIDS, in the case of the lentivirus HIVs. Such assays for use in identifying a subject as having or having had a retrovirus infection include, but are not limited to, PCR-based assays that detect specific polynucleotides that are present during viral infection and replication; ELISA-based assays that detect viral antigens present or neutralizing antibodies present in a subject sample; plaque-reduction assays, which can be used to determine the serum dilution at which 50% of the infectious virus (e.g., HIV) is neutralized ($NT_{50}$), as demonstrated herein, in addition to the monitoring of specific symptoms associated with the retrovirus infection.

Examples of retrovirus infections that can be inhibited or treated using the compositions and methods described herein include, but are not limited to, bovine lentiviruses (e.g., bovine immunodeficiency virus, Jembrana disease virus), equine lentiviruses (e.g., equine infectious anemia virus), feline lentiviruses (e.g., feline immunodeficiency virus), ovine/caprine lentivirus (e.g., caprine arthritis-encephalitis virus, ovine lentivirus, visna virus) and primate lentiviruses, such as, human immunodeficiency virus (HIV), including human immunodeficiency virus type 1 (HIV-1), human immunodeficiency virus type 2 (HIV-2), human immunodeficiency virus type 3 (HIV-3), simian AIDS retrovirus SRV-1, including human T-cell lymphotropic virus type 4 (HIV-4) and simian immunodeficiency virus (SIV), Rous sarcoma virus, avian leukosis virus, and avian myeloblastosis virus, Avian carcinoma Mill Hill virus 2, Avian myelocytomatosis virus 29, Avian sarcoma virus CT10, Fujinami sarcoma virus, UR2 sarcoma virus, Y73 sarcoma virus, Jaagsiekte sheep retrovirus, Langur virus, Mason-Pfizer monkey virus, Squirrel monkey retrovirus, mouse mammary tumour virus, murine leukemia virus, feline leukemia virus, feline sarcoma virus, Gibbon ape leukemia virus, Guinea pig type-C oncovirus, Porcine type-C oncovirus, Finkel-Biskis-Jinkins murine sarcoma virus, Gardner-Arnstein feline sarcoma virus, Hardy-Zuckerman feline sarcoma virus, Harvey murine sarcoma virus, Kirsten murine sarcoma virus, Moloney murine sarcoma virus, Snyder-Theilen feline sarcoma virus, Woolly monkey sarcoma virus, avian reticuloendotheliosis viruses, including, but not limited to, Chick syncytial virus, Reticuloendotheliosis virus, and Trager duck spleen necrosis virus, bovine leukemia virus and Human T-lymphotropic virus.

In some embodiments, the compositions and methods described herein are useful for the treatment or inhibition of the human lentivirus known as "human immunodeficiency virus-1" or "HIV-1", also referred to herein as HTLV-III, LAV or HTLV-III/LAV, the etiological agent of the acquired immune deficiency syndrome (AIDS) and related disorders. (Barre-Sinoussi, et al., Science, 220:868-871 (1983); Gallo, et al., Science, 224:500-503 (1984); Levy, et al., Science, 225:840-842 (1984); Popovic, et al., Science, 224:497-500 (1984); Sarngadharan, et al., Science, 224:506-508 (1984); Siegal, et al., New England Journal of Medicine, 305:1439-1444 (1981)). AIDS is characterized by a long asymptomatic period followed by the progressive degeneration of the immune system and the central nervous system. Studies of the HIV-1 virus indicate that replication is highly regulated, and both latent and lytic infection of the CD4 positive helper subset of T-lymphocytes occur in tissue culture (Zagury, et al., Science, 231:850-853 (1986)). The expression of the virus in infected patients also appears to be regulated as the titer of infectious virus remains low throughout the course of the disease. Molecular studies of the replication and genomic organization of HIV-1 show that it encodes a number of genes (Ratner, et al., Nature, 313:277-284 (1985); Sanchez-Pescador, et al., Science, 227:484-492 (1985); Muesing, et al., Nature, 313:450-457 (1985); Wain-Hobson, et al., Cell, 40:9-17 (1985)). Three of the genes, the gag, pol and env genes are common to all retroviruses. The genome also encodes additional genes that are not common to most retroviruses, the tat, rev (formerly referred to as art), nef, vif, vpr and vpu genes (Sodroski, et al., Science, 231:1549-1553 (1986); Arya, et al., Science, 229:69-73 (1985); Sodroski, et al., Nature, 321:412-417 (1986); Feinberg, et al., Cell, 46:807-817 (1986); Haseltine, Journal of Acquired Immune Deficiency Syndrome, 1:217-240 (1988); Cohen, et al., Nature, 334:532-534 (1988); Wong-Staal, et al., AIDS Res. and Human Retro Viruses, 3:33-39 (1987)). Nucleotide sequences from viral genomes of other retroviruses, particularly HIV-2 and simian immunodeficiency viruses, SIV (previously referred to as STLV-III), also contain the structural genes including env as well as regulatory sequences such as tat, rev and nef (Guyader, et al., Nature, 326:662-669 (1987); Chakrabarti, et al., Nature, 328:543-547 (1987)). These three HIV viruses share a similar genetic organization, even though there can be sequence variations.

Infection with HIV leads, in most cases, to a progressive decline in the number and functions of CD4+ T cells with the eventual appearance of clinical manifestations of cellular immunodeficiency, such as opportunistic infections and malignancies, i.e., AIDS (Fauci, et al., Ann. Int. Med., 100:92-99 (1984)). The entry of HIV-1 into the target cells requires, in association with the CD4 molecule, the simultaneous virus binding to a chemokine receptor. CXCR4 and CCR5, members of the chemokine receptor family of proteins, serve as secondary coreceptors for HIV-1 isolates that are tropic for T-cell lines or macrophages, respectively. Deng et al. (1996) Nature 381:661-6; Doranz et al. (1996) Cell 86:1149-59; and Berger et al. (1998) Nature 391:240. CXCR4 or CCR5, in conjunction with CD4, form a functional cellular receptor for entry of certain strains of HIV into cells. Reports indicated that the viral envelope glycoprotein gp120 interacts directly with chemokine receptors generally at a step following CD4 binding. Lapham et al. (1996) Science 274:602-605; Moore (1997) Science 276:51; Wu et al. (1996) Nature 384:179-183; and Hesselgesser et al. (1997) Current Biology 7:112-121. Envelope variants will selectively interact with either CXCR4 or CCR5.

HIV-1 strains transmitted in vivo generally use CCR5 (CCR5 viruses). Fenyo et al. (1998) Nature 391:240; Samson et al. (1996) Nature 382:722-5; Shankarappa et al. (1999) J. Virol. 73:10489-502; and Scarlatti et al. (1997) Nature Med. 3:1259-65. These viruses typically infect macrophages and primary CD4+ lymphocytes, and do not form syncytia in vitro. Bjorndal et al. (1997) J. Virol. 71:7478-87. These viruses are said to be macrophage tropic (M-tropic). After primary HIV-1 infection, viral populations are usually characterized by molecular heterogeneity. Shankarappa et al. (1999); and Glushakova et al. (1999) J. Clin. Invest. 104:R7-R11. Years after chronic infection is established, strains using CXCR4 emerge in about 50% of infected individuals (Berger et al. (1998); Scarlatti et al. (1997); Koot et al. (1993); and Connor et al. (1997) J. Exp. Med. 185:621-8). CXCR4 strains not only infect primary T-lymphocytes but also replicate in T-cell lines and induce syncytia (Bjorndal et al. (1997)). These viruses are said to be T-cell tropic (T-tropic). This difference in cell tropism correlates with disease progression. During HIV infection, strains isolated from individuals early in the course of their infection are usually M-tropic, while viruses isolated from approximately 50% of individuals with advanced immunodeficiency also include viruses that are T-tropic.

CXCR4 strains have been shown to have a striking influence on HIV-1 disease progression. Cytopathicity toward the general CD4+T cell population in lymphoid tissue is associated with the use of CXCR4. Glushakova et al. (1999). The emergence of CXCR4 virus is predictive of rapid depletion of CD4+ cells and acceleration of HIV-1 disease progression. Berger et al. (1998); Scarlatti et al. (1997); and Connor et al. (1997). (1997). A recent analysis of HIV-1 coreceptor use in infected individuals suggested that the rapid CD4+ cell decline is related to the ability of CXCR4 viruses to infect an expanded spectrum of crucial target cells as compared to CCR5 strains. Blaak et al. (2000) Proc. Natl. Acad. Sci. USA 97:1269-74. In vitro results suggest that selective blockade of CXCR4 receptors may prevent the switch from the less pathogenic CCR5 strains to the more pathogenic CXCR4 strains. Este et al. (1999) J. Virol. 73:5577-85. Coreceptor use plays a critical role in viral tropism, pathogenesis, and disease progression.

Efficacy of Treatment

One key advantage of the methods, uses, and compositions comprising the small molecule pyridomyrimidone viral inhibitors of Formula (I), e.g., 4-acetyl-2,3,7,8-tetrahydro-3-phenylpyrido[1,2-f]pyrimidin-1-one or CMLDBU6128, is the ability of producing marked anti-viral effects in a human subject without causing significant toxicities or adverse effects. The efficacy of the treatments described herein can be measured by various parameters commonly used in evaluating treatment of viral infections, including, but not limited to, viral lesions, viral genomic integration, viral load, rate of virus production, rate of viral replication, time to symptoms of infection, duration of survival, overall response rate, duration of response, and/or quality of life.

As used herein, the terms "treat," "treatment," "treating," or "amelioration" refer to therapeutic treatments, wherein the object is to reverse, alleviate, ameliorate, inhibit, slow down or stop the progression or severity of a condition associated with, an infection, disease, or disorder. The term "treating" includes reducing or alleviating at least one adverse effect or symptom of a condition, disease or disorder associated with, for example, an orthopoxvirus infection, such as, but not limited to, fevers or skin lesions. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

Accordingly, the "therapeutically effective amount" of a small molecule pyridomyrimidone viral inhibitor of Formula (I) described herein, e.g., 4-acetyl-2,3,7,8-tetrahydro-3-phenylpyrido[1,2-f]pyrimidin-1-one (CMLDBU6128), to be administered is governed by such considerations, and, as used herein, refers to the minimum amount necessary that is safe and sufficient to prevent, ameliorate, or treat, or stabilize, a disorder or condition mediated by a viral infection, such as an orthopoxvirus infection or a retroviral infection. Thus, the therapeutically effective amount of a small molecule pyridomyrimidone viral inhibitor of Formula (I), e.g., 4-acetyl-2,3,7,8-tetrahydro-3-phenylpyrido[1,2-f]pyrimidin-1-one (CMLDBU6128), described herein is the minimum amount necessary to, for example, increase the time of survival; to inhibit, reduce, or prevent: viral gene expression, viral replication, viral genomic integration, viral transmission; to treat or prevent the occurrence or recurrence of a viral infection; ameliorate the symptoms of the viral infection; slow the course of disease progression resulting from the viral infection; slow or inhibit a symptom of the viral infection; slow or inhibit the establishment of secondary symptoms of the viral infection; and/or inhibit the development of a secondary symptom of a viral infection; or any combination thereof.

An effective amount, as used herein, also includes an amount sufficient to delay the development of a symptom of the viral infection, alter the course of the viral infection, for example, but not limited to, slow the progression of a symptom of the viral infection, reverse a symptom of the viral infection, or any combination thereof. Thus, it is not possible to specify the exact "effective amount." However, for any given case, an appropriate "effective amount" can be determined by one of ordinary skill in the art using only routine experimentation.

For example, in some embodiments, the methods described herein comprise administering an effective amount of a pharmaceutical composition comprising a small molecule pyridomyrimidone viral inhibitor of Formula (I), e.g., 4-acetyl-2,3,7,8-tetrahydro-3-phenylpyrido[1,2-f]pyrimidin-1-one (CMLDBU6128), described herein to a subject in order to alleviate a symptom of an orthopoxvirus infection, or other such disorder. As used herein, "alleviating a symptom of an orthopoxvirus infection" is ameliorating or reducing any condition or symptom associated with the orthopoxvirus infection. As compared with an equivalent untreated control, such reduction or degree of prevention is at least 5%, at least 10%, at least 20%, at least 30%, at least 40%, at least 50%, at least 60%, at least 70%, at least 80%, at least 90%, at least 95%, or more, as measured by any standard technique. Ideally, the infection is completely cleared as detected by any standard method known in the art. A patient who is being treated for an orthopoxvirus infection is one who a medical practitioner has diagnosed as having such a condition. Diagnosis can be by any suitable means. Diagnosis and monitoring can involve, for example, detecting the level of infected cells in a biological sample (for example, a tissue or lymph node sample, blood test, or urine test), using, for example, PCR assays for detection of viral genome, ELISA assays for detection of viral antigens, detecting the level of a surrogate marker of the infection in a biological sample, detecting symptoms associated with the specific infection, or detecting immune cells involved in the immune response typical of such infections.

Symptoms of infection with an orthopoxvirus that can be treated or inhibited using the compositions and methods described herein include, but are not limited to, fever, malaise, head and body aches, vomiting, skin lesions, severe edema and erythema, encephalitis (alteration of mental status and focal neurologic deficits), and/or myelitis (upper- and lower-motor neuron dysfunction, sensory level and bowel and bladder dysfunction).

In such embodiments of the aspects described herein related to orthopoxvirus infections, a small molecule pyridomyrimidone viral inhibitor of Formula (I) described herein, e.g., 4-acetyl-2,3,7,8-tetrahydro-3-phenylpyrido[1,2-f]pyrimidin-1-one (CMLDBU6128), can be optionally formulated with one or more agents currently used for the treatment of the orthopoxvirus infection, such as, for example, vaccines against the orthopoxvirus, Cidofovir, STI-571 (Reeves et al. 2005, Nature Med. 11:731-739) and/or ST-246 (Yang et al. 2005, J. Virol. 79:13139-13149). The effective amount of such other agents depends on the amount of the viral inhibitor of Formula (I) present in the formulation, the strain or species of viral infection or treatment, and other factors discussed herein, and as understood by one of skill in the art. These are generally used in the same dosages and with administration routes as used herein before or about from 1 to 99% of the heretofore employed dosages.

In other embodiments, the methods described herein comprise administering an effective amount of a pharmaceutical composition comprising a small molecule pyridomyrimidone viral inhibitor of Formula (I), e.g., 4-acetyl-2,3,7,8-tetrahydro-3-phenylpyrido[1,2-f]pyrimidin-1-one (CMLDBU6128), described herein to a subject in order to alleviate a symptom of a retrovirus infection, or other such disorder. As used herein, "alleviating a symptom of a retrovirus infection" is ameliorating or reducing any condition or symptom associated with the retrovirus infection. As compared with an equivalent untreated control, such reduction or degree of prevention is at least 5%, at least 10%, at least 20%, at least 30%, at least 40%, at least 50%, at least 60%, at least 70%, at least 80%, at least 90%, at least 95%, or more, as measured by any standard technique. Ideally, the infection is completely cleared as detected by any standard method known in the art. A patient who is being treated for a retrovirus infection is one who a medical practitioner has diagnosed as having such a condition. Diagnosis can be by any suitable means. Diagnosis and monitoring can involve, for example, detecting the level of infected cells in a biological sample (for example, a tissue or lymph node sample, blood test, or urine test), using, for example, PCR assays for detection of viral genome, ELISA assays for detection of viral antigens, detecting the level of a surrogate marker of the infection in a biological sample, detecting symptoms associated with the specific infection, or detecting immune cells involved in the immune response typical of such infections.

In some embodiments of the methods described herein, the subject having or at risk for the retroviral infection is infected with HIV. In some such embodiments, the symptoms associated with the HIV infection comprise the symptoms associated with the development of AIDS. The symptoms associated with HIV infection can include, but are not limited to, reduction in CD4+ T cell numbers, pain (peripheral neuropathy); fever, cough, and other cold/flu symptoms; night sweats; diarrhea, nausea, and other indigestion symptoms; lymph swelling or other immunological symptoms; weight loss and loss of appetite; candida in the mouth; secondary bacterial and/or viral infections; elevated liver enzymes; reduction in central nervous system and brain function; depression; overall reduced immunity; AIDS-related complications (ARC), including, but not limited to, progressive generalization lymphadenia (PGL), Kaposi's sarcoma, Pneumocystis carinii pneumonia, cataplectic purpura thrombocytopenica; AIDS related neurological syndromes, including, but not limited to, AIDS dementia complications, AIDS encephalopathy, disseminated sclerosis ortropical paraplegia; as well as anti HIV antibody-positive and HIV-positive syndrome including that in silent patients.

In such embodiments of the aspects described herein related to retroviral infections, a small molecule pyridomyrimidone viral inhibitor of Formula (I) described herein, e.g., 4-acetyl-2,3,7,8-tetrahydro-3-phenylpyrido[1,2-f]pyrimidin-1-one (CMLDBU6128), can be optionally formulated with one or more agents currently used for the treatment of the retroviral infection, such as, for example, one or more anti-HIV agents known to be useful in the treatment of HIV infection or AIDS. The effective amount of such other agents depends on the amount of the viral inhibitor of Formula (I) present in the formulation, the strain or species of viral infection or treatment, and other factors discussed herein, and as understood by one of skill in the art. These are generally used in the same dosages and with administration routes as used herein before or about from 1 to 99% of the heretofore employed dosages.

Administration, Dosages, and Durations

A small molecule pyridomyrimidone viral inhibitor of Formula (I) described herein, e.g., 4-acetyl-2,3,7,8-tetrahydro-3-phenylpyrido[1,2-f]pyrimidin-1-one (CMLDBU6128), can be formulated, dosed, and administered in a fashion consistent with good medical practice for use in the treatment of the infections described herein, such as a smallpox virus infection or HIV infection. Factors for consideration in this context include the particular viral species or viral strain being treated, the particular subject being treated, the clinical condition of the individual subject, the site of delivery of the agent, the method of administration, the scheduling of administration, and other factors known to medical practitioners.

Effective amounts, toxicity, and therapeutic efficacy of the small molecule pyridomyrimidone orthopoxvirus inhibitors of Formula (I), e.g., 4-acetyl-2,3,7,8-tetrahydro-3-phenylpyrido[1,2-f]pyrimidin-1-one (CMLDBU6128), can be determined by standard pharmaceutical procedures in cell cultures or experimental animals, and as described herein, e.g., for determining the $LD_{50}$ (the dose lethal to 50% of the population) and the $ED_{50}$ (the dose therapeutically effective in 50% of the population). The dosage can vary depending upon the dosage form employed and the route of administration utilized. The dose ratio between toxic and therapeutic effects is the therapeutic index and can be expressed as the ratio $LD_{50}/ED_{50}$. Compositions and methods that exhibit large therapeutic indices are preferred. A therapeutically effective dose can be estimated initially from cell culture assays. Also, a dose can be formulated in animal models to achieve a circulating plasma concentration range that includes the $IC_{50}$ (i.e., the concentration of the viral inhibitor), which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

Depending on the type and severity of the disease, about 1 μg/kg to 100 mg/kg (e.g., 0.1-20 mg/kg) of a small molecule pyridomyrimidone viral inhibitor of Formula (I), e.g., 4-acetyl-2,3,7,8-tetrahydro-3-phenylpyrido[1,2-f]pyrimidin-1-one (CMLDBU6128), is an initial candidate dosage range for administration to the subject, whether, for example, by one or more separate administrations, or by continuous infusion. A typical daily dosage might range from about 1 μg/kg to about 100 mg/kg or more, depending on the factors mentioned above. For repeated administrations over several days or longer, depending on the condition, the treatment is sustained until the infection is treated or cleared, as measured by the methods described herein or known in the art. However, other dosage regimens can be useful. The progress of the therapeutic methods described herein is easily monitored by conventional techniques and assays, such as those described herein, or known to one of skill in the art.

The duration of the therapeutic methods described herein can continue for as long as medically indicated or until a desired therapeutic effect (e.g., those described herein) is achieved. In certain embodiments, administration of a small molecule pyridomyrimidone viral inhibitor of Formula (I), i.e., "antiviral therapy" is continued for at least 1 month, at least 2 months, at least 4 months, at least 6 months, at least 8 months, at least 10 months, at least 1 year, at least 2 years, at least 3 years, at least 4 years, at least 5 years, at least 10 years, at least 20 years, or for at least a period of years up to the lifetime of the subject.

The small molecule pyridomyrimidone viral inhibitors of Formula (I), e.g., 4-acetyl-2,3,7,8-tetrahydro-3-phenylpyrido[1,2-f]pyrimidin-1-one (CMLDBU6128), can be administered to a subject, e.g., a human subject, in accordance with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Local administration can be used if, for example, extensive side effects or toxicity is associated with the viral inhibitor. An ex vivo strategy can also be used for therapeutic applications. A viral inhibitor can be administered by any appropriate route which results in effective treatment in the subject, i.e. administration results in delivery to a desired location in the subject where at least a portion of the composition delivered, i.e., at least one small molecule pyridomyrimidone viral inhibitors of Formula (I), is active in the desired site for a period of time.

Exemplary modes of administration of the small molecule pyridomyrimidone orthopoxvirus inhibitors of Formula (I), e.g., 4-acetyl-2,3,7,8-tetrahydro-3-phenylpyrido[1,2-f]pyrimidin-1-one or CMLDBU6128, include, but are not limited to, injection, infusion, inhalation (e.g., intranasal or intratracheal), ingestion, rectal, vaginal, and topical (including buccal and sublingual) administration. The phrases "parenteral administration" and "administered parenterally" as used herein, refer to modes of administration other than enteral and topical administration, usually by injection. As used herein, "injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration," "administered systemically", "peripheral administration" and "administered peripherally" as used herein refer to the administration of a small molecule pyridomyrimidone viral inhibitor of Formula (I), e.g., 4-acetyl-2,3,7,8-tetrahydro-3-phenylpyrido[1,2-f]pyrimidin-1-one (CMLDBU6128), other than directly into a target site, tissue, or organ, such as the lung, such that it enters the subject's circulatory system and, thus, is subject to metabolism and other like processes.

In some embodiments of the aspects described herein, the small molecule pyridomyrimidone viral inhibitors of Formula (I), e.g., 4-acetyl-2,3,7,8-tetrahydro-3-phenylpyrido[1,2-f]pyrimidin-1-one (CMLDBU6128), are administered by intravenous infusion or injection. In some embodiments, where local treatment is desired, for example, at or near a site of an infection or lymph node, the small molecule pyridomyrimidone viral inhibitors of Formula (I), e.g., 4-acetyl-2,3,7,8-tetrahydro-3-phenylpyrido[1,2-f]pyrimidin-1-one (CMLDBU6128), can be administered by intralesional administration. Additionally, in some embodiments, the viral inhibitors described herein can be administered by pulse infusion, particularly with declining doses of the inhibitors. Preferably the dosing is given by injections, most preferably intravenous or subcutaneous injections, depending in part on whether the administration is brief or chronic.

Pharmaceutical Formulations

Therapeutic formulations of the viral inhibitors described herein can be prepared, in some aspects, by mixing a small molecule pyridomyrimidone viral inhibitor of Formula (I), e.g., 4-acetyl-2,3,7,8-tetrahydro-3-phenylpyrido[1,2-f]pyrimidin-1-one (CMLDBU6128), having the desired degree of purity with one or more pharmaceutically acceptable carriers, excipients or stabilizers (Remington's Pharmaceutical Sciences 16th edition, Osol, A. Ed. (1980)), in the form of lyophilized formulations or aqueous solutions. Such therapeutic formulations of the viral inhibitors described herein include formulation into pharmaceutical compositions or pharmaceutical formulations for parenteral administration, e.g., intravenous; mucosal, e.g., intranasal; enteral, e.g., oral; topical, e.g., transdermal; ocular, or other mode of administration.

As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the activity of, carrying, or transporting the small molecule pyridomyrimidone viral inhibitors of Formula (I), e.g., 4-acetyl-2,3,7,8-tetrahydro-3-phenylpyrido[1,2-f]pyrimidin-1-one (CMLDBU6128), from one organ, or portion of the body, to another organ, or portion of the body.

Some non-limiting examples of acceptable carriers, excipients, or stabilizers that are nontoxic to recipients at the dosages and concentrations employed, include pH buffered solutions such as phosphate, citrate, and other organic acids; antioxidants, including ascorbic acid and methionine; lubricating agents, such as magnesium stearate, sodium lauryl sulfate and talc; excipients, such as cocoa butter and suppository waxes; oils, such as peanut oil, cottonseed oil, safflower oil, sesame oil, olive oil, corn oil and soybean oil; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, HDL, LDL, or immunoglobulins; hydrophilic polymers, such as polyvinylpyrrolidone; amino acids such as glycine, glutamine, asparagine, histidine, arginine, or lysine; monosaccharides, disaccharides, and other carbohydrates including mannose, starches (corn starch or potato starch), or dextrins; cellulose, and its derivatives, such as sodium carboxymethyl cellulose, methylcellulose, ethyl cellulose, microcrystalline cellulose and cellulose acetate; chelating agents such as EDTA; sugars such as sucrose, glucose, lactose, mannitol, trehalose or sorbitol; salt-forming counter-ions such as sodium; metal complexes (e.g. Zn-protein complexes); glycols, such as propylene glycol; polyols, such as glycerin; esters, such as ethyl oleate and ethyl laurate; agar; buffering agents, such as magnesium hydroxide and aluminum hydroxide; alginic acid; pyrogen-free water; isotonic saline; Ringer's solution; polyesters, polycarbonates and/or polyanhydrides; C2-C12 alcohols, such as ethanol; powdered tragacanth; malt; and/or non-ionic surfactants such as TWEEN™, PLURONICS™ or polyethylene glycol (PEG); and/or other non-toxic compatible substances employed in pharmaceutical formulations. Wetting agents, coloring agents, release agents, coating agents, sweetening agents, flavoring agents, perfuming agents, preservative and antioxidants can also be present in the formulation.

In some embodiments of the aspects described herein, the therapeutic formulations comprising a small molecule pyridomyrimidone viral inhibitor of Formula (I) comprises a pharmaceutically acceptable salt, typically, e.g., sodium chloride, and preferably at about physiological concentrations. Optionally, the formulations described herein can contain a pharmaceutically acceptable preservative. In some embodiments of the aspects described herein, the preservative concentration ranges from 0.1 to 2.0%, typically v/v. Suitable preservatives include those known in the pharmaceutical arts. Benzyl alcohol, phenol, m-cresol, methylparaben, and propylparaben are examples of preservatives. Optionally, the formulations of the invention can include a pharmaceutically acceptable surfactant at a concentration of 0.005 to 0.02%.

In some embodiments of the aspects described herein, a small molecule pyridomyrimidone viral inhibitor of Formula (I), e.g., 4-acetyl-2,3,7,8-tetrahydro-3-phenylpyrido[1,2-f]pyrimidin-1-one (CMLDBU6128), can be specially formulated for administration of the compound to a subject in solid, liquid or gel form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam, or part of, for example, a comtraceptive device or composition; (5) sublingually; (6) ocularly; (7) transdermally; (8) transmucosally; or (9) nasally. Additionally, a small molecule pyridomyrimidone viral inhibitor of Formula (I), e.g., 4-acetyl-2,3,7,8-tetrahydro-3-phenylpyrido[1,2-f]pyrimidin-1-one (CMLDBU6128), can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquids such as suspensions (e.g., aqueous or non-aqueous liquid suspensions, oil-in-water emulsions, or water-in-oil liquid emulsions), solutions, and elixirs; and sterile solids (e.g., crystalline or amorphous solids) that can be reconstituted to provide liquid dosage forms.

In some embodiments of the aspects described herein, parenteral dosage forms of the small molecule pyridomyrimidone viral inhibitors of Formula (I), e.g., 4-acetyl-2,3,7,8-tetrahydro-3-phenylpyrido[1,2-f]pyrimidin-1-one (CMLDBU6128), can be administered to a subject with a viral infection or at increased risk for a viral infection by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

Suitable vehicles that can be used to provide parenteral dosage forms described herein are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

In some embodiments of the aspects described herein, the small molecule pyridomyrimidone viral inhibitors of Formula (I), e.g., 4-acetyl-2,3,7,8-tetrahydro-3-phenylpyrido[1,2-f]pyrimidin-1-one (CMLDBU6128), are formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington's Pharmaceutical Sciences, 18th ed., Mack Publishing, Easton, Pa. (1990).

Due to their ease of administration, tablets and capsules represent the most advantageous solid oral dosage unit forms, in which case solid pharmaceutical excipients are used. If desired, tablets can be coated by standard aqueous or nonaqueous techniques. These dosage forms can be prepared by any of the methods of pharmacy. In general, pharmaceutical compositions and dosage forms are prepared by uniformly and intimately admixing the active ingredient(s) with liquid carriers, finely divided solid carriers, or both, and then shaping the product into the desired presentation if necessary.

Typical oral dosage forms of the compositions are prepared by combining the pharmaceutically acceptable salt of a small molecule pyridomyrimidone viral inhibitor of Formula (I), e.g., 4-acetyl-2,3,7,8-tetrahydro-3-phenylpyrido[1,2-f]pyrimidin-1-one (CMLDBU6128), in an intimate admixture with at least one excipient according to conventional pharmaceutical compounding techniques. Excipients can take a wide variety of forms depending on the form of the composition desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, kaolin, diluents, granulating agents, lubricants, binders, and disintegrating agents.

Binders suitable for use in the pharmaceutical formulations described herein include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical formulations described herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions described herein is typically present in from about 50 to about 99 weight percent of the pharmaceutical composition.

Disintegrants are used in the oral pharmaceutical formulations described herein to provide tablets that disintegrate when exposed to an aqueous environment. A sufficient amount of disintegrant that is neither too little nor too much to detrimentally alter the release of the active ingredient(s) should be used to form solid oral dosage forms of the small molecule pyridomyrimidone viral inhibitors of Formula (I), e.g., 4-acetyl-2,3,7,8-tetrahydro-3-phenylpyrido[1,2-f]pyrimidin-1-one (CMLDBU6128). The amount of disintegrant used varies based upon the type of formulation, and is readily discernible to those of ordinary skill in the art. Disintegrants that can be used to form oral pharmaceutical formulations include, but are not limited to, agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums, and mixtures thereof.

Lubricants that can be used to form oral pharmaceutical formulations of the orthopoxvirus inhibitors described herein, include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL® 200, manufactured by W. R. Grace Co. of Baltimore, Md.), a coagulated aerosol of synthetic silica (marketed by Degussa Co. of Piano, Tex.), CAB-O-SIL® (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

In other embodiments, lactose-free pharmaceutical formulations and dosage forms are provided, wherein such compositions preferably contain little, if any, lactose or other mono- or disaccharides. As used herein, the term "lactose-free" means that the amount of lactose present, if any, is insufficient to substantially increase the degradation rate of an active ingredient. Lactose-free compositions of the disclosure can comprise excipients which are well known in the art and are listed in the USP (XXI)/NF (XVI), which is incorporated herein by reference.

The oral formulations of the small molecule pyridomyrimidone viral inhibitors of Formula (I), e.g., 4-acetyl-2,3,7,8-tetrahydro-3-phenylpyrido[1,2-f]pyrimidin-1-one (CMLDBU6128), further encompass, in some embodiments of the aspects described herein, anhydrous pharmaceutical compositions and dosage forms comprising the orthopoxvirus inhibitors described herein as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Anhydrous pharmaceutical compositions and dosage forms described herein can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected. Anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

A viral inhibitor described herein, such as a small molecule pyridomyrimidone viral inhibitor of Formula (I), e.g., 4-acetyl-2,3,7,8-tetrahydro-3-phenylpyrido[1,2-f]pyrimidin-1-one (CMLDBU6128) can be administered directly to the airways in the form of an aerosol or by nebulization. Accordingly, for use as aerosols, in some embodiments of the aspects described herein, a viral inhibitor described herein, such as a small molecule pyridomyrimidone viral inhibitor of Formula (I), e.g., 4-acetyl-2,3,7,8-tetrahydro-3-phenylpyrido[1,2-f]pyrimidin-1-one (CMLDBU6128), can be packaged in a pressurized aerosol container together with suitable propellants, for example, hydrocarbon propellants like propane, butane, or isobutane with conventional adjuvants. In other embodiments of the aspects described herein, the orthopoxvirus inhibitor can be administered in a non-pressurized form such as in a nebulizer or atomizer.

The term "nebulization" is well known in the art to include reducing liquid to a fine spray. Preferably, by such nebulization small liquid droplets of uniform size are produced from a larger body of liquid in a controlled manner. Nebulization can be achieved by any suitable means, including by using many nebulizers known and marketed today. As is well known, any suitable gas can be used to apply pressure during the nebulization, with preferred gases being those which are chemically inert to small molecule pyridomyrimidone viral inhibitors of Formula (I), e.g., 4-acetyl-2,3,7,8-tetrahydro-3-phenylpyrido[1,2-f]pyrimidin-1-one (CMLDBU6128). Exemplary gases include, but are not limited to, nitrogen, argon or helium.

In other embodiments of the aspects described herein, a small molecule pyridomyrimidone viral inhibitor of Formula (I), e.g., 4-acetyl-2,3,7,8-tetrahydro-3-phenylpyrido[1, 2-f]pyrimidin-1-one (CMLDBU6128), can be administered directly to the airways in the form of a dry powder. For use as a dry powder, an orthopoxvirus inhibitor can be administered by use of an inhaler. Exemplary inhalers include metered dose inhalers and dry powdered inhalers.

Suitable powder compositions include, by way of illustration, powdered preparations of a small molecule pyridomyrimidone viral inhibitor of Formula (I), e.g., 4-acetyl-2,3,7,8-tetrahydro-3-phenylpyrido[1,2-f]pyrimidin-1-one (CMLDBU6128), thoroughly intermixed with lactose, or other inert powders acceptable for, e.g., intrabronchial administration. The powder compositions can be administered via an aerosol dispenser or encased in a breakable capsule which may be inserted by the subject into a device that punctures the capsule and blows the powder out in a steady stream suitable for inhalation. The compositions can include propellants, surfactants, and co-solvents and may be filled into conventional aerosol containers that are closed by a suitable metering valve.

Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic an diagnostic agents to the respiratory tract," in Critical Reviews in Therapeutic Drug Carrier Systems, 6:273-313 (1990); Anderson et al., Am. Rev. Respir. Dis., 140: 1317-1324 (1989)) and have potential for the systemic delivery of peptides and proteins as well (Patton and Platz, Advanced Drug Delivery Reviews, 8:179-196 (1992)); Timsina et. al., Int. J. Pharm., 101: 1-13 (1995); and Tansey, I. P., Spray Technol. Market, 4:26-29 (1994); French, D. L., Edwards, D. A. and Niven, R. W., Aerosol Sci., 27: 769-783 (1996); Visser, J., Powder Technology 58: 1-10 (1989)); Rudt, S, and R. H. Muller, J. Controlled Release, 22: 263-272 (1992); Tabata, Y, and Y. Ikada, Biomed. Mater. Res., 22: 837-858 (1988); Wall, D. A., Drug Delivery, 2: 10 1-20 1995); Patton, J. and Platz, R., Adv. Drug Del. Rev., 8: 179-196 (1992); Bryon, P., Adv. Drug. Del. Rev., 5: 107-132 (1990); Patton, J. S., et al., Controlled Release, 28: 15 79-85 (1994); Damms, B. and Bains, W., Nature Biotechnology (1996); Niven, R. W., et al., Pharm. Res., 12(9); 1343-1349 (1995); and Kobayashi, S., et al., Pharm. Res., 13(1): 80-83 (1996), contents of all of which are herein incorporated by reference in their entirety.

Topical dosage forms of the small molecule pyridomyrimidone viral inhibitors of Formula (I), e.g., 4-acetyl-2,3,7,8-tetrahydro-3-phenylpyrido[1,2-f]pyrimidin-1-one (CMLDBU6128), are also provided in some embodiments, and include, but are not limited to, creams, lotions, ointments, gels, shampoos, sprays, aerosols, solutions, emulsions, and other forms known to one of skill in the art. See, e.g., Remington's Pharmaceutical Sciences, 18th ed., Mack Publishing, Easton, Pa. (1990); and Introduction to Pharmaceutical Dosage Forms, 4th ed., Lea & Febiger, Philadelphia, Pa. (1985). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well known in the art. See, e.g., Remington's Pharmaceutical Sciences, 18.sup.th Ed., Mack Publishing, Easton, Pa. (1990). and Introduction to Pharmaceutical Dosage Forms, 4th Ed., Lea & Febiger, Philadelphia, Pa. (1985). Dosage forms suitable for treating mucosal tissues within the oral cavity can be formulated as mouthwashes, as oral gels, or as buccal patches. Additional transdermal dosage forms include "reservoir type" or "matrix type" patches, which can be applied to the skin and worn for a specific period of time to permit the penetration of a desired amount of active ingredient.

Examples of transdermal dosage forms and methods of administration that can be used to administer a small molecule pyridomyrimidone viral inhibitor of Formula (I), e.g., 4-acetyl-2,3,7,8-tetrahydro-3-phenylpyrido[1,2-f]pyrimidin-1-one (CMLDBU6128) in some embodiments of the aspects described herein, include, but are not limited to, those disclosed in U.S. Pat. Nos. 4,624,665; 4,655,767; 4,687,481; 4,797,284; 4,810,499; 4,834,978; 4,877,618; 4,880,633; 4,917,895; 4,927,687; 4,956,171; 5,035,894; 5,091,186; 5,163,899; 5,232,702; 5,234,690; 5,273,755; 5,273,756; 5,308,625; 5,356,632; 5,358,715; 5,372,579; 5,421,816; 5,466,465; 5,494,680; 5,505,958; 5,554,381; 5,560,922; 5,585,111; 5,656,285; 5,667,798; 5,698,217; 5,741,511; 5,747,783; 5,770,219; 5,814,599; 5,817,332; 5,833,647; 5,879,322; and 5,906,830, each of which are incorporated herein by reference in their entirety.

Suitable excipients (e.g., carriers and diluents) and other materials that can be used to provide transdermal and mucosal dosage forms of the inhibitors described herein are well known to those skilled in the pharmaceutical arts, and depend on the particular tissue or organ to which a given pharmaceutical composition or dosage form will be applied. In addition, depending on the specific tissue to be treated, additional components may be used prior to, in conjunction with, or subsequent to treatment with a small molecule pyridomyrimidone viral inhibitor of Formula (I), e.g., 4-acetyl-2,3,7,8-tetrahydro-3-phenylpyrido[1,2-f]pyrimidin-1-one (CMLDBU6128). For example, penetration enhancers can be used to assist in delivering the active ingredients to or across the tissue.

In some embodiments of the aspects described herein, the pharmaceutical formulations comprising the small molecule pyridomyrimidone viral inhibitors of Formula (I), e.g., 4-acetyl-2,3,7,8-tetrahydro-3-phenylpyrido[1,2-f]pyrimidin-1-one (CMLDBU6128), can further comprise more than one active compound as necessary for the particular indication being treated, preferably those with complementary activities that do not adversely affect each other. For example, in some embodiments, it can be desirable to further provide antibodies that bind to and/or neutralize the virus being treated or inhibited in the formulation comprising the viral inhibitor of Formula (I). In other embodiments, the formulation comprising the viral inhibitor of Formula (I) can further comprise a cytotoxic agent, cytokine, growth inhibitory agent and/or nucleoside analog. Such molecules are suitably present in combination in amounts that are effective for the purpose intended.

In some embodiments of the aspects described herein, the active ingredients of the formulations comprising the small molecule pyridomyrimidone viral inhibitors of Formula (I), e.g., 4-acetyl-2,3,7,8-tetrahydro-3-phenylpyrido[1,2-f]pyrimidin-1-one (CMLDBU6128), described herein, can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In some embodiments of these aspects, the small molecule pyridomyrimidone viral inhibitors of Formula (I), e.g., 4-acetyl-2,3,7,8-tetrahydro-3-phenylpyrido[1,2-f]pyrimidin-1-one (CMLDBU6128), can be administered to a subject by controlled- or delayed-release means. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Chemg-ju, Controlled Release Dosage Form Design, 2 (Technomic Publishing, Lancaster, Pa.: 2000)). Controlled-release formulations can be used to control an Orthopoxvirus inhibitor's onset of action, duration of action, plasma levels within the therapeutic window, and peak blood levels. In particular, controlled- or extended-release dosage forms or formulations can be used to ensure that the maximum effectiveness of the small molecule pyridomyrimidone viral inhibitors of Formula (I), e.g., 4-acetyl-2,3,7,8-tetrahydro-3-phenylpyrido[1,2-f]pyrimidin-1-one (CMLDBU6128), is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with the small molecule pyridomyrimidone viral inhibitors of Formula (I), e.g., 4-acetyl-2,3,7,8-tetrahydro-3-phenylpyrido[1,2-f]pyrimidin-1-one (CMLDBU6128). Examples include, but are not limited to, those described in U.S. Pat. Nos. 3,845,770; 3,916,899; 3,536,809; 3,598,123; 4,008,719; 5674,533; 5,059,595; 5,591,767; 5,120,548; 5,073,543; 5,639,476; 5,354,556; 5,733,566; and 6,365,185 B1; each of which is incorporated its entirety herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, DUOLITE® A568 and DUOLITE® AP143 (Rohm&Haas, Spring House, Pa. USA).

In some embodiments of the aspects described herein, the s small molecule pyridomyrimidone viral inhibitors of Formula (I), e.g., 4-acetyl-2,3,7,8-tetrahydro-3-phenylpyrido[1,2-f]pyrimidin-1-one (CMLDBU6128), for use in the various therapeutic formulations and compositions, and methods thereof, described herein, is administered to a subject by sustained release or in pulses. Pulse therapy is not a form of discontinuous administration of the same amount of a composition over time, but comprises administration of the same dose of the composition at a reduced frequency or administration of reduced doses. Sustained release or pulse administrations are particularly preferred in chronic conditions, such as cancer, as each pulse dose can be reduced and the total amount of a compound of a viral inhibitor administered over the course of treatment to the patient is minimized.

The interval between pulses, when necessary, can be determined by one of ordinary skill in the art. Often, the interval between pulses can be calculated by administering another dose of the composition when the composition or the active component of the composition is no longer detectable in the subject prior to delivery of the next pulse. Intervals can also be calculated from the in vivo half-life of the composition. Intervals may be calculated as greater than the in vivo half-life, or 2, 3, 4, 5 and even 10 times greater the composition half-life. Various methods and apparatus for pulsing compositions by infusion or other forms of delivery to the patient are disclosed in U.S. Pat. Nos. 4,747,825; 4,723,958; 4,948,592; 4,965,251 and 5,403,590.

In some embodiments of the aspects described herein, sustained-release preparations comprising the small molecule pyridomyrimidone viral inhibitors of Formula (I), e.g., 4-acetyl-2,3,7,8-tetrahydro-3-phenylpyrido[1,2-f]pyrimidin-1-one (CMLDBU6128), can be prepared. Suitable examples of sustained-release preparations include semipermeable matrices of solid hydrophobic polymers containing the inhibitor, in which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as those used in the LUPRON DEPOT™ (injectable microspheres composed of lactic acid-glycolic acid copolymer and leuprolide acetate), and poly-D-(−)-3-hydroxybutyric acid.

The formulations comprising the small molecule pyridomyrimidone viral inhibitors of Formula (I), e.g., 4-acetyl-2,3,7,8-tetrahydro-3-phenylpyrido[1,2-f]pyrimidin-1-one (CMLDBU6128), to be used for in vivo administration are preferably sterile. This is readily accomplished by filtration through, for example, sterile filtration membranes, and other methods known to one of skill in the art.

Combination Therapies

In some embodiments of the aspects described herein, the compositions and methods comprising the novel small molecule pyridomyrimidone viral inhibitors of Formula (I), e.g., 4-acetyl-2,3,7,8-tetrahydro-3-phenylpyrido[1,2-f]pyrimidin-1-one (CMLDBU6128), further comprise administration or treatment with one or more additional therapies specific for the virus being treated, or any broad-spectrum viral therapy. Examples of such additional therapies include, without limitation, neutralizing antibodies specific for one or more viral family members, vaccination against one or more viral family members, 4'-thio-2'-deoxynucleosides, therapeutic cytokine agents, such as interferon (IFN), interferon α-2a, interferon α-2b, consensus interferon (CIFN), and interleukin-12, ursodeoxycholic acid (UDCA), Nevirapine, ribavirin, amantadine, remantadine, and glycyrrhizin, or any combination of these therapies.

For the treatment or prevention of viral infections in such embodiments comprising combination therapies, the appropriate dosage of a small molecule pyridomyrimidone viral inhibitor of Formula (I), e.g., 4-acetyl-2,3,7,8-tetrahydro-3-phenylpyrido[1,2-f]pyrimidin-1-one (CMLDBU6128), will depend on the type of infection to be treated, as defined above, the severity and course of the infection, whether the viral inhibitor is administered for preventive or therapeutic purposes, previous therapy, the subject's clinical history and response to the viral inhibitor, and the discretion of the attending physician. The viral inhibitor is suitably administered to the subject at one time or over a series of treatments.

In those embodiments where a combination therapy regimen is applied, a small molecule pyridomyrimidone viral inhibitor of Formula (I), e.g., 4-acetyl-2,3,7,8-tetrahydro-3-phenylpyrido[1,2-f]pyrimidin-1-one (CMLDBU6128), and one or more anti-viral therapeutic agents as described herein are administered in a therapeutically effective or synergistic amount. As used in such embodiments encompassing combination therapies, a therapeutically effective amount is such that co-administration of a small molecule pyridomyrimidone viral inhibitor of Formula (I), e.g., 4-acetyl-2,3,7,8-tetrahydro-3-phenylpyrido[1,2-f]pyrimidin-1-one (CMLDBU6128), and one or more additional therapeutic agents, or administration of a therapeutic composition or formulation comprising a viral inhibitor as described herein, results in reduction or inhibition of the infection as described herein. A "therapeutically synergistic amount" is that amount of a small molecule pyridomyrimidone viral inhibitor of Formula (I), e.g., 4-acetyl-2,3,7,8-tetrahydro-3-phenylpyrido[1,2-f]pyrimidin-1-one (CMLDBU6128), and one or more other therapeutic agents necessary to synergistically or significantly reduce or eliminate conditions or symptoms associated with a particular infection.

In some embodiments of the aspects described herein, a small molecule pyridomyrimidone viral inhibitor of Formula (I), e.g., 4-acetyl-2,3,7,8-tetrahydro-3-phenylpyrido[1,2-f]pyrimidin-1-one (CMLDBU6128), and one or more other therapeutic agents can be administered simultaneously or sequentially in an amount and for a time sufficient to reduce or eliminate the occurrence or recurrence of a viral infection. In some embodiments, the small molecule pyridomyrimidone viral inhibitors of Formula (I), e.g., 4-acetyl-2,3,7,8-tetrahydro-3-phenylpyrido[1,2-f]pyrimidin-1-one (CMLDBU6128), and one or more other therapeutic agents can be administered as maintenance or prophylactic therapy to prevent or reduce the likelihood of infection.

As will be understood by those of ordinary skill in the art, the appropriate doses of additional therapeutic agents will be generally around those already employed in clinical therapies, e.g., where the therapeutics are administered alone or in combination with other therapeutics. Variation in dosage will likely occur depending on the condition being treated. The physician administering treatment will be able to determine the appropriate dose for the individual subject.

As used herein, the term "orthopoxvirus therapy" or "orthopoxvirus therapeutic agent" refers to a therapy known to be useful in treating an orthopoxvirus infection. Examples of orthopoxvirus therapeutic agents include, but are not limited to, e.g., Vaccinia virus immunoglobulin (VIG), Cidofovir ([(S)-1-(3-hydroxy-2-phosphonylmethoxypropyl) cytosine-] [HPMPC]), methisazone, inhibitors of S-adenosylhomocysteine hydrolase (SAH), analogs of the nucleoside adenosine, such as Neplanacin A and 3-Deazaneplanacin A, interferons, cytokines, antagonists (e.g., neutralizing antibodies) that bind to one or more of the orthopoxvirus family members, and other bioactive and organic chemical agents, etc. Combinations thereof are also included in the embodiments described herein.

As used herein, the term "retroviral therapy" or "retroviral therapeutic agent" refers to a therapy known to be useful in treating a retroviral infection, such as an anti-HIV agent or anti-HIV therapeutic agent. As used herein, an "anti-HIV agent" is any agent which is directly or indirectly effective in the inhibition of HIV integrase or another enzyme required for HIV replication or infection, the treatment or prophylaxis of HIV infection, and/or the treatment, prophylaxis or delay in the onset of AIDS. It is understood that an anti-HIV agent is effective in treating, preventing, or delaying the onset of HIV infection or AIDS and/or diseases or conditions arising therefrom or associated therewith. For example, the compounds described herein can be effectively administered, whether at periods of pre-exposure and/or post-exposure, in combination with effective amounts of one or more HIV antivirals, immunomodulators, antiinfectives, or vaccines useful for treating HIV infection or AIDS, such as those disclosed in Table 1 of WO 01/38332 or in the Table in WO 02/30930. Suitable HIV antivirals for use in combination with the compounds described herein for antiretroviral therapy can include, but are not limited to, HAART, protease inhibitors, fusion inhibitors, integrase inhibitors, co-receptor specific agents, 3TC, AZT, nevirapine, non-nucleoside analogue reverse transcriptase inhibitors and nucleoside analogue reverse transcriptase inhibitors. HAART can be three or more antiretroviral drugs in combination, including as examples regimens that have at least one protease inhibitor, or at least a reverse transcriptase inhibitor and a protease inhibitor; or at least two reverse transcriptase inhibitors with at least one protease inhibitor.

Typical HIV reverse transcriptase inhibitors for use in the present invention include nucleoside analogs, e.g., AZT (Zidovudine), ddi (didanosine), ddc (zalcitabine), D4T (stavudine), 3TC (lamivudine), tenofovir, ZIAGEN (abacavir), COMBIVIR (mix of AZT and 3TC), and non-nucleoside analogs, e.g., VIRAMUNE (nevirapine), RESCRIPTOR (delavirdine), SUSTIVA (efavirenz). Typical HIV protease inhibitors include INVIRASE (saquinavir), NORVIR (ritonavir), ATAZANAVIR, CRIXIVAN (indinavir), VIRACEPT (nelfinavir), AGENERASE (amprenivir), KALETRA (lopinavir and ritonavir) and FORTOVASE (saquinavir in a soft gelatin form). Thus, HAART can also be "triple cocktail" therapy—a three drug regimen to combat HIV wherein one of the three drugs is usually a protease inhibitor (and the other two are usually reverse transcriptase inhibitors). It will be understood that the scope of combinations of the compounds of this invention with HIV antivirals, immunomodulators, anti-infectives or vaccines is not limited to the foregoing substances or to the list in the above-referenced Tables in WO 01/38332 and WO 02/30930, but includes in principle any combination with any pharmaceutical composition useful for the treatment of HIV infection or AIDS. The HIV antivirals and other agents will typically be employed in these combinations in their conventional dosage ranges and regimens as reported in the art, including, for example, the dosages described in the Physicians' Desk Reference, 63rd edition, Thomson PDR, 2009. The dosage ranges for a compound of the invention in these combinations are the same as those set forth above. It is understood that pharmaceutically acceptable salts of the compounds of the invention and/or the other agents (e.g., indinavir sulfate) can be used as well.

The term "cytokine" is a generic term for proteins released by one cell population which act on another cell as intercellular mediators. Examples of such cytokines are lymphokines, monokines, and traditional polypeptide hormones. Included among cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); epidermal growth factor; hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta and -gamma colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12, IL-13, IL-15, IL-16, IL-17, IL-18, IL-20, IL-21, IL-22, IL-23, IL-25, IL-27, IL-29, IL-33, etc.; a tumor necrosis factor such as TNF-alpha or TNF-beta; and other polypeptide factors including LIF and kit ligand (KL). As used herein, the term cytokine includes proteins from natural sources or from recombinant cell culture and biologically active equivalents of the native sequence cytokines.

Viral Inhibitor Screening Assays and Methods

Also provided herein, in some aspects, are novel screening assays and methods for the identification and characterization of viral inhibitors, such as the inhibitors described herein. These assays and methods are based on the use of replication-competent engineered "reporter viruses," as described herein, that express reporter molecules operably linked to or under control of viral temporally regulated promoter elements. By expressing one or more reporter molecules under the control of early viral promoters, intermediate viral promoters, or late viral promoters, the stage of viral life cycle can be determined based on the reporter molecule being expressed. Such engineered reporter viruses can then be used to identify inhibitors of viral gene expression in high-throughput screening assays of test compounds, as described herein, based on which reporter molecule is inhibited by a given test compound.

Accordingly, in some aspects, provided herein are high-throughput inhibitor screening assays for identifying novel viral inhibitors. Such assays can comprise: (a) contacting a population of cells infected with a reporter virus with a test compound; (b) maintaining the reporter virus infected cells of step (a) in the presence of the test compound; (c) measuring or analyzing the expression of one or more reporter molecules expressed by the reporter virus following the contacting with the test compound, such that decreased expression or lack of expression of the reporter molecule relative to a control population of cells that was not contacted with the test compound is indicative of the test compound being a viral inhibitor.

The reporter viruses used in the screening assays described herein are engineered to express one or more different reporter molecules operably linked to an early viral promoter, an intermediate viral promoter, and/or a late viral promoter. In some embodiments of the aspects described herein, a screening assay comprises different reporter viruses each having a different reporter molecule operably linked to only one type of viral promoter, i.e., an early viral promoter, an intermediate viral promoter, or a late viral promoter, such that each reporter virus is specific for and indicative of a particular stage of the viral cycle. In other embodiments of the aspects described herein, a screening assay comprises a single reporter virus having a different reporter molecules operably linked to more than one type of viral promoter, such that expression of each reporter molecule is specific for and indicative of a particular stage of the viral cycle. In some embodiments of the aspects described herein, various combinations of reporter viruses can be used in the screening assays.

As used herein, a "reporter molecule" refer to a protein or molecule that can be used to produce a measurable signal such as fluorescence, color, or luminescence. Reporter protein coding sequences encode proteins whose presence in the cell or organism is readily observed. For example, fluorescent proteins cause a cell to fluoresce when excited with light of a particular wavelength, luciferases cause a cell to catalyze a reaction that produces light, and enzymes such as β-galactosidase convert a substrate to a colored product.

There are several different ways to measure or quantify a reporter molecule for use in the screening assays described herein, depending on the particular reporter and what kind of characterization data is desired. In some embodiments of the aspects described herein, microscopy can be a useful technique for obtaining both spatial and temporal information on reporter activity, particularly at the single cell level. In other embodiments of the aspects described herein, flow cytometers can be used for measuring the distribution in reporter activity across a large population of cells, as well as in plate-based multi-well formats. In some embodiments of the aspects described herein, plate readers can be used for taking population average measurements of many different samples over time, In other embodiments of the aspects described herein, instruments that combine such various functions, can be used, such as multiplex plate readers designed for flow cytometers, and combination microscopy and flow cytometric instruments.

Fluorescence from fluorescent reporter molecules can be readily quantified using a microscope, plate reader or flow cytometer equipped to excite the fluorescent protein with the appropriate wavelength of light. Since several different fluorescent proteins are available, multiple gene expression measurements can be made in parallel. Non-limiting examples of fluorescent proteins useful for the reporter viruses described herein are provided in Table 1.

TABLE 1

Examples of Fluorescent Protein Molecules

| Name | Protein | Description | Tag | Emission | Excitation | Length |
|---|---|---|---|---|---|---|
| BBa_E0030 | EYFP | enhanced yellow fluorescent protein derived from *A. victoria* GFP | None | 527 | 514 | 723 |
| BBa_E0020 | ECFP | engineered cyan fluorescent protein derived from *A. victoria* GFP | None | 476 | 439 | 723 |
| BBa_E1010 | mRFP1 | highly engineered mutant of red fluorescent protein from *Discosoma striata* (coral) | None | 607 | 584 | 681 |
| BBa_E2050 | mOrange | derivative of mRFP1, yeast-optimized | None | 562 | 548 | 744 |
| BBa_E0040 | GFPmut3b | green fluorescent protein derived from jellyfish *Aequeora victoria* wild-type GFP (SwissProt: P42212 | None | 511 | 501 | 720 |
| BBa_J52021 | | dnTraf6-linker-GFP | | | | 1446 |
| BBa_J52026 | | dnMyD88-linker-GFP | | | | 1155 |
| BBa_I715022 | | Amino Portion of RFP | | | | 462 |
| BBa_I715023 | | Carboxyl portion of RFP | | | | 220 |
| BBa_I712028 | | CherryNLS - synthetic construct monomeric red fluorescent protein with nuclear localization sequence | | | | 733 |
| BBa_K125500 | | GFP fusion brick | | | | 718 |
| BBa_K106000 | | GFP, AarI BD part | | | | 714 |
| BBa_K106004 | | mCherry, AarI AB part | | | | 708 |
| BBa_K106005 | | mCherry, AarI BD part | | | | 708 |
| BBa_K106028 | | GFP, AarI AB part | | | | 714 |
| BBa_K165005 | | Venus YFP, yeast optimized for fusion | | | | 744 |
| BBa_K157005 | | Split-Cerulean-cCFP | | | | 261 |
| BBa_K157006 | | Split-Cerulean-nCFP | | | | 483 |
| BBa_K157007 | | Split-Venus-cYFP | | | | 261 |
| BBa_K157008 | | Split-Venus-nYFP | | | | 486 |
| BBa_K125810 | | slr2016 signal sequence + GFP fusion for secretion of GFP | | | | 779 |
| BBa_K082003 | GFP | GFP(+LVA) | | | | 756 |
| BBa_K156009 | | OFP (orange fluorescent protein) | | | | 864 |
| BBa_K156010 | | SBFP2 (strongly enhanced blue fluorescent protein) | | | | 720 |
| BBa_K106671 | | GFP, AarI AD part | | | | 714 |
| BBa_K294055 | GFPmut3b | GFP RFP Hybrid | None | 511 | 501 | 720 |
| BBa_K192001 | | CFP +tgt +lva | | | | 858 |
| BBa_K180001 | GFPmut3b | Green fluorescent protein (+LVA) | LVA | | | 754 |
| BBa_K283005 | | lpp_ompA_eGFP_streptavidin | | | | 1533 |
| BBa_K180008 | mCherry | mCherry (rights owned by Clontech) | | | | 708 |
| BBa_K180009 | mBanana | mBanana (rights owned by Clontech) | | | | 708 |

Luminescence can be readily quantified using a plate reader or luminescence counter. Luciferases can be used as reporter molecules for various embodiments described herein, for example, in samples where background fluorescence might result in an inability to distinguish between cells expressing an output and those that do not, because cells tend to have little to no background luminescence in the absence of a luciferase. Non-limiting examples of luciferases are provided in Table 2.

TABLE 2

Examples of Luciferases

| Name | Description | Length |
| --- | --- | --- |
| BBa_J52011 | dnMyD88-linker-Rluc | 1371 |
| BBa_J52013 | dnMyD88-linker-Rluc-linker-PEST191 | 1872 |
| BBa_I712019 | Firefly luciferase - luciferase from Photinus pyralis | 1653 |

In other embodiments, enzymes that produce colored substrates can be quantified using spectrophotometers or other instruments that can take absorbance measurements including plate readers. Like luciferases, enzymes like β-galactosidase tend to amplify low signals.

TABLE 3

Examples of Enzymes that Produce Colored Substrates

| Name | Protein | Description | Length |
| --- | --- | --- | --- |
| BBa_I732006 | | lacZ alpha fragment | 234 |
| BBa_I732005 | | lacZ (encoding beta-galactosidase, full-length) | 3075 |
| BBa_K147002 | | xylE | 924 |

In some embodiments, the test compounds or agents are not added until after about 1 day, about 2, days, about 3 days, about 4 days, about 5 days, about 6 days, or more after infection of the cells with the reporter virus(es).

Following addition of the test compounds or agents, the reporter virus-infected cells can be cultured or maintained for additional time, e.g. 1 day, 2 days, 3 days, 4 days, 5 days, 6 days, 7 days, 8 days or more, prior to measuring or analyzing the expression of one or more reporter molecules expressed by the reporter virus, e.g., by a fluorescence based measurement system.

As used herein, the term "test compound or agent" refers to compounds or agents and/or compositions of the same that are to be screened for their ability to modulate (e.g., inhibit or increase) virus activity, including, but not limited to, viral gene expression, viral replication, viral infectivity, etc. Test compounds or agents can be small molecules, peptides, antibodies, antibody fragments, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Depending upon the particular embodiment being practiced, the test compounds may be provided free in solution, or may be attached to a carrier, or a solid support, e.g., beads.

Additionally, for the methods described herein, test compounds can be screened individually, or in groups. Group screening is particularly useful where hit rates for effective test compounds are expected to be low such that one would not expect more than one positive result for a given group. The compound screening assays can be used in a high through-put screen. High through-put screening is a process in which libraries of compounds are tested for a given activity. High through-put screening seeks to screen large numbers of compounds rapidly and in parallel. For example, using microtiter plates and automated assay equipment, a pharmaceutical company can perform as many as 100,000 assays per day in parallel.

A number of small molecule libraries are known in the art and commercially available. These small molecule libraries can be screened for inflammasome inhibition using the screening methods described herein. A chemical library or compound library is a collection of stored chemicals usually used ultimately in high-throughput screening or industrial manufacture. The chemical library can comprise in simple terms of a series of stored chemicals. Each chemical has associated information stored in some kind of database with information such as the chemical structure, purity, quantity, and physiochemical characteristics of the compound. For example, the libraries used herein, and libraries from Vitas-M Lab and Biomol International, Inc. Chemical compound libraries such as those from of 10,000 compounds and 86,000 compounds from NIH Roadmap, Molecular Libraries Screening Centers Network (MLSCN) can be screened. A comprehensive list of compound libraries can be found at http://www.broad.harvard.edu/chembio/platform/screening/compound_libraries/index.htm. Commercially available compound libraries can be obtained from, e.g., Sigma Aldrich (St. Louis, Mo.), ArQule (Woburn, Mass.), Panvera (Madison, Wis.), Vitas-M Lab (Moscoe, Russia), Biomol International (Plymouth, Mass.). These libraries can be screened using the screening devices and methods described herein.

Nucleic acid agents, include but are not limited to, antisense oligonucleotide, RNA interfering agents (e.g. siRNA, shRNA), ribozyme, aptamers, and decoy oligonucleotides. Methods of preparing such nucleic acids are known in the art and easily available to those skilled in the art.

In some embodiments of the aspects described herein, the test agent is an antibody. As used herein, the term "antibody" includes complete immunoglobulins, antigen binding fragments of immunoglobulins, as well as antigen binding proteins that comprise antigen-binding domains of immunoglobulins. Antigen binding fragments of immunoglobulins include, for example, Fab, Fab', F(ab')2, scFv and dAbs.

In some embodiments of the aspects described herein, the test compound or agent decreases viral gene expression by at least 5%, at least 10%, at least 20%, at least 30%, at least 40%, at least 50%, at least 60%, at least 70%, at least 80%, at least 90%, at least 1-fold, at least 1.1-fold, at least 1.5-fold, at least 2-fold, at least 3-fold, at least 4-fold, at least 5-fold, or more.

Generally, compounds can be tested at any concentration that can inhibit viral gene expression in an infected population of cells relative to a control over an appropriate time period. In some embodiments, compounds are tested at concentration in the range of about 0.01 nM to about 1000 mM. In some embodiments, the compound is tested in the range of about 0.1 nM to about 500 µM, about 0.1 µM to about 20 µM, about 0.1 µM to about 10 µM, or about 0.1 µM to about 5 µM.

The screening assays described herein can involve more than one measurement of the observable reporter function. Multiple measurements can allow for following the viral gene expression and activity over incubation time with the test compound. In some embodiments, the reporter molecule expression is measured at a plurality of times to allow monitoring of the effects of the test compound at different times following infection with the reported virus.

The screening assay can be followed by one or more subsequent assays to further identify whether the identified test compound has properties desirable for the intended use. For example, the screening assay can be followed by a second assay selected from the group consisting of measurement of any of: bioavailability, toxicity, or pharmacokinetics of the identified test compound, but is not limited to these methods.

Embodiments of the various aspects described herein can be illustrated by the following numbered paragraphs:

1. A pharmaceutical composition comprising a pyridopyrimidinone viral inhibitor of Formula (I):

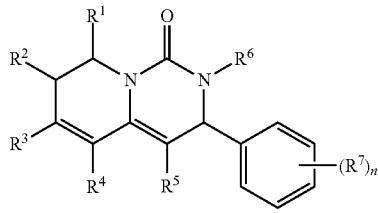

FORMULA (I)

wherein:
$R^1$, $R^2$ and $R^4$ are independently, H, alkyl, alkenyl, alkynyl, aryl, heteroaryl, cyclyl, heterocyclyl, acyl, amino, hydroxyl, alkoxy, $C(O)OR^8$, or $C(O)N(R^8)_2$, each of which can be optionally substituted;
$R^3$ is H, alkyl, alkenyl, alkynyl, aryl, heteroaryl, cyclyl, heterocyclyl, acyl, amino, or alkyl silane (e.g., trialkylsilane), each of which can be optionally substituted;
$R^5$ is H, alkyl, alkenyl, alkynyl, aryl, heteroaryl, cyclyl, heterocyclyl, acyl, amino, hydroxyl, alkoxy, mercapato, thioalkoxy, sulfinyl, sulfonyl, $C(O)OR^8$, or $C(O)N(R^8)_2$, each of which can be optionally substituted;
$R^6$ is H, alkyl, alkenyl, alkynyl, aryl, heteroaryl, cyclyl, heterocyclyl, or acyl, each of which can be optionally substituted;
$R^7$ is independently for each occurrence H, halo, cyano, amino, nitro, hydroxyl, mercapto, thioalkoxy, sulfinyl, sulfonyl, alkyl, alkenyl, alkynyl, alkoxy, acyl, aryl, heteroaryl, cyclyl, heterocyclyl, $C(O)OR^8$, or $C(O)N(R^8)_2$, each of which can be optionally substituted;
$R^8$ is H, alkyl, alkenyl, alkynyl, aryl, heteroaryl, cyclyl, or heterocyclyl, each of which can be optionally substituted;
n is 0, 1, 2, 3, 4, or 5; and
pharmaceutically acceptable salts thereof in a pharmaceutically acceptable carrier.

2. The pharmaceutical composition of paragraph 1, wherein the pyridopyrimidinone viral inhibitor of Formula (I) is 4-acetyl-2,3,7,8-tetrahydro-3-phenylpyrido[1,2-f]pyrimidin-1-one (CMLDBU6128), having a chemical structure:

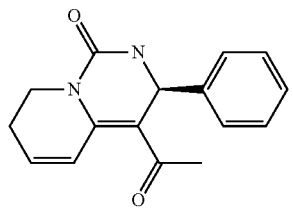

CMLDBU6128

3. A method of preventing an orthopoxvirus infection in a subject in need thereof, the method comprising administering to a subject having, or at risk for, an orthopoxvirus infection, a therapeutically effective amount of any of the pharmaceutical compositions of paragraphs 1-2.

4. A method of treating an orthopoxvirus infection in a subject in need thereof, the method comprising administering to a subject having an orthopoxvirus infection a therapeutically effective amount of any of the pharmaceutical compositions of paragraphs 1-2.

5. The method of any one of paragraphs 3 or 4, further comprising the step of selecting, diagnosing, or identifying a subject having an orthopoxvirus infection or who is at increased risk for an orthopoxvirus infection.

6. The method of one any of paragraphs 3-5, wherein the orthopoxvirus is a Vaccinia virus or a Variola virus.

7. The method of any one of paragraphs 3-6, further comprising administration of one or more additional orthopoxvirus therapeutic agents.

8. A method of preventing a retrovirus infection in a subject in need thereof, the method comprising administering to a subject having, or at risk for, a retrovirus infection a therapeutically effective amount of any of the pharmaceutical compositions of any one of paragraphs 1-2.

9. A method of treating a retrovirus infection in a subject in need thereof, the method comprising administering to a subject having a retrovirus infection a therapeutically effective amount of any of the pharmaceutical compositions of any one of paragraphs 1-2.

10. The method of any one of paragraphs 8 or 9, further comprising the step of selecting, diagnosing, or identifying a subject having a retrovirus infection or who is at increased risk for a retrovirus infection.

11. The method of any one of paragraphs 8-10, wherein the retrovirus is a lentivirus.

12. The method of paragraph 11, wherein the lentivirus is HIV.

13. The method of any one of paragraphs 8-12, further comprising administration of one or more additional retroviral therapeutic agents.

14. The method of paragraph 13, wherein the retroviral therapeutic agent is an anti-HIV agent.

15. A method of inhibiting viral replication comprising contacting a cell infected with a virus an effective amount of any of the pharmaceutical compositions of any one of paragraphs 1-2.

16. The method of paragraph 15, wherein the contacting is in vitro or ex vivo.

17. The method of paragraph 15, wherein the contacting is in vivo.

18. The method of any one of paragraphs 15-17, wherein the virus is an orthopoxvirus.

19. The method of any one of paragraphs 15-17, wherein the virus is a retrovirus.

20. The method of paragraph 19, wherein the retrovirus is a lentivirus.

21. The method of paragraph 20, wherein the lentivirus is HIV.

22. A pyridopyrimidinone viral inhibitor of Formula (I) for use in treating an orthopoxvirus infection:

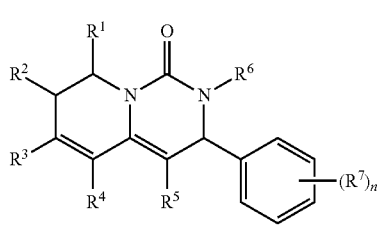

FORMULA (I)

wherein:

R$^1$, R$^2$ and R$^4$ are independently, H, alkyl, alkenyl, alkynyl, aryl, heteroaryl, cyclyl, heterocyclyl, acyl, amino, hydroxyl, alkoxy, C(O)OR$^8$, or C(O)N(R$^8$)$_2$, each of which can be optionally substituted;

R$^3$ is H, alkyl, alkenyl, alkynyl, aryl, heteroaryl, cyclyl, heterocyclyl, acyl, amino, or alkyl silane (e.g., trialkylsilane), each of which can be optionally substituted;

R$^5$ is H, alkyl, alkenyl, alkynyl, aryl, heteroaryl, cyclyl, heterocyclyl, acyl, amino, hydroxyl, alkoxy, mercapato, thioalkoxy, sulfinyl, sulfonyl, C(O)OR$^8$, or C(O)N(R$^8$)$_2$, each of which can be optionally substituted;

R$^6$ is H, alkyl, alkenyl, alkynyl, aryl, heteroaryl, cyclyl, heterocyclyl, or acyl, each of which can be optionally substituted;

R$^7$ is independently for each occurrence H, halo, cyano, amino, nitro, hydroxyl, mercapto, thioalkoxy, sulfinyl, sulfonyl, alkyl, alkenyl, alkynyl, alkoxy, acyl, aryl, heteroaryl, cyclyl, heterocyclyl, C(O)OR$^8$, or C(O)N(R$^8$)$_2$, each of which can be optionally substituted;

R$^8$ is H, alkyl, alkenyl, alkynyl, aryl, heteroaryl, cyclyl, or heterocyclyl, each of which can be optionally substituted;

n is 0, 1, 2, 3, 4, or 5; and pharmaceutically acceptable salts thereof in a pharmaceutically acceptable carrier.

23. The use of paragraph 22, wherein the pyridopyrimidinone viral inhibitor of Formula (I) is 4-acetyl-2,3,7,8-tetrahydro-3-phenylpyrido[1,2-f]pyrimidin-1-one (CMLDBU6128), having a chemical structure:

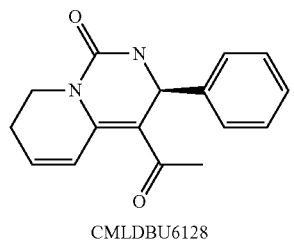 [SMILES: CC(=O)C1=C2C=CCCN2C(=O)N[C@H]1c1ccccc1]

CMLDBU6128

24. The use of one any of paragraphs 22-23, wherein the orthopoxvirus is a Vaccinia virus or a Variola virus.

25. A pyridopyrimidinone viral inhibitor of Formula (I) for use in treating a retrovirus infection:

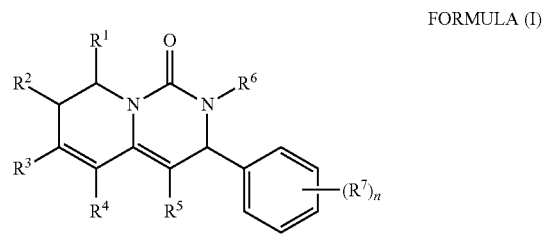

FORMULA (I)

wherein:

R$^1$, R$^2$ and R$^4$ are independently, H, alkyl, alkenyl, alkynyl, aryl, heteroaryl, cyclyl, heterocyclyl, acyl, amino, hydroxyl, alkoxy, C(O)OR$^8$, or C(O)N(R$^8$)$_2$, each of which can be optionally substituted;

R$^3$ is H, alkyl, alkenyl, alkynyl, aryl, heteroaryl, cyclyl, heterocyclyl, acyl, amino, or alkyl silane (e.g., trialkylsilane), each of which can be optionally substituted;

R$^5$ is H, alkyl, alkenyl, alkynyl, aryl, heteroaryl, cyclyl, heterocyclyl, acyl, amino, hydroxyl, alkoxy, mercapato, thioalkoxy, sulfinyl, sulfonyl, C(O)OR$^8$, or C(O)N(R$^8$)$_2$, each of which can be optionally substituted;

R$^6$ is H, alkyl, alkenyl, alkynyl, aryl, heteroaryl, cyclyl, heterocyclyl, or acyl, each of which can be optionally substituted;

R$^7$ is independently for each occurrence H, halo, cyano, amino, nitro, hydroxyl, mercapto, thioalkoxy, sulfinyl, sulfonyl, alkyl, alkenyl, alkynyl, alkoxy, acyl, aryl, heteroaryl, cyclyl, heterocyclyl, C(O)OR$^8$, or C(O)N(R$^8$)$_2$, each of which can be optionally substituted;

R$^8$ is H, alkyl, alkenyl, alkynyl, aryl, heteroaryl, cyclyl, or heterocyclyl, each of which can be optionally substituted;

n is 0, 1, 2, 3, 4, or 5; and pharmaceutically acceptable salts thereof in a pharmaceutically acceptable carrier.

26. The use of paragraph 25, wherein the pyridopyrimidinone viral inhibitor of Formula (I) is 4-acetyl-2,3,7,8-tetrahydro-3-phenylpyrido[1,2-f]pyrimidin-1-one (CMLDBU6128), having a chemical structure:

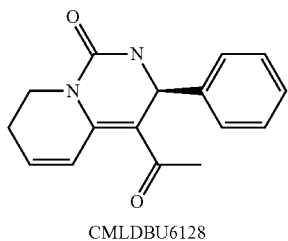 [SMILES: CC(=O)C1=C2C=CCCN2C(=O)N[C@H]1c1ccccc1]

CMLDBU6128

27. The use of one any of paragraphs 25-26, wherein the retrovirus is a lentivirus.
28. The use of paragraph 27, wherein the lentivirus is HIV.
29. A screening assay for identifying an orthopoxvirus inhibitor, the assay comprising:
   a. contacting a population of cells infected with a reporter orthopoxvirus with a test compound, wherein said reporter orthopoxvirus comprises one or more reporter molecules each operably linked to a different viral gene promoter, wherein expression of the one or more reporter molecules is indicative of a particular stage of the orthopoxvirus life cycle;
   b. contacting the population of cells of step (a) with a test compound; and
   c. measuring or analyzing the expression of the one or more reporter molecules expressed by the reporter orthopoxvirus following the contacting with the test compound, wherein a significant decrease in expression or lack of expression of the one or more reporter molecules relative to a control population of cells infected with the reporter orthopoxvirus that was not contacted with the test compound is indicative of the test compound being an orthopoxvirus inhibitor.
30. The screening assay of paragraph 29, wherein the one or more reporter molecules is a fluorescent molecule, a luciferase molecule, or an enzyme.
31. The screening assay of any one of paragraphs 29-30, wherein the viral gene promoter is an intermediate viral promoter or a late viral promoter.

This invention is further illustrated by the following examples which should not be construed as limiting.

EXAMPLES

The Poxyiridae family of DNA viruses includes the orthopoxviruses Variola (smallpox) and the emerging pathogen monkeypox. Naturally occurring smallpox was eradicated through concerted vaccination with the prototypical orthopoxvirus, vaccinia, and routine vaccination has since been discontinued[1]. The potential use of smallpox as a bioweapon, however, has heightened interest in developing countermeasures[2]. In addition, recent reports show an increase in human monkeypox cases in Africa over the last 30 years[3], and the first report of human monkeypox in the Western Hemisphere occurred in 2003[4]. There is consequently renewed effort to develop effective strategies to treat orthopoxvirus-infected individuals[5].

Orthopoxviruses replicate in the cytoplasm and encode macromolecular machinery for transcription, post-transcriptional mRNA processing, and DNA genome replication[6]. Gene expression proceeds in a classical cascade mechanism that is broadly categorized into early, intermediate, and late phases[7]. Viral replication occurs in perinuclear viral factories and a major mode of transmission of these predominantly intracellular viruses is to adjacent cells via trafficking to the cell membrane or upon infected cell rupture[8]. While these core viral functions are conserved across orthopoxviruses, host-range and virulence factors are divergent[9][10] Variola is an obligate human pathogen with a mortality rate of 30-50% which caused an estimated 300-500 million deaths in the 20$^{th}$ century[11]. Monkeypox has a mortality rate of 1-10% and can transmit to humans zoonotically from animal reservoirs[12].

There is currently no treatment approved by the Food and Drug Administration for orthopoxvirus-infected individuals. Although a number of small-molecule inhibitors have been identified, many are nucleoside analogs where selectivity for viral over host enzymes poses developmental challenges 13 14. Compounds that show promise in a clinical setting are the cidofovir derivative, CMX001 15, which is a nucleoside analog, and ST-246 16, which has a unique mechanism of action in preventing viral egress from infected cells. With the majority of inhibitors, including CMX001 and ST-246, viral resistance is rapidly achieved in cell culture[16][17][18]. As with many antimicrobial strategies, effective treatment is likely to involve combination therapy.

As described herein, we generated a series of high-yield reporter vaccinia viruses to allow rapid screening of compounds for antiviral activity. These viruses were used in a screen of a diversity-oriented synthesis library to discover a non-nucleoside analog, CMLDBU6 128, which was able to inhibit several orthopoxviruses in vitro. Herein, we report identification and the characterization of its antiviral effects.
Assays Used for Identification of Inhibitory Agents HeLa cells were infected with high MOI of a reporter virus in the presence or absence of test compounds. Differential gene expression of genes expressed at various stages of the viral replication cycle were measured, such as an early gene (Venus), and a late gene (Chemy). Reference compounds also used within the assays included Arabinose C, which inhibits viral DNA replication, and ST-256, which inhibits assembly of virus infectious progeny.
Identification of an Orthopoxvirus Inhibitor We generated replication-competent reporter vaccinia viruses with fluorescent reporter proteins under control of temporally regulated early, intermediate, and/or late viral promoters (Table 1). For screening, we used a dual reporter virus with mCherry under control of the late F1 7R promoter and Venus under control of the C11R early promoter (late red early Venus; LREV virus). Compounds were screened for their ability to reduce well fluorescence after high multiplicity of infection (MOI) of A549 cell monolayers (FIG. 1A). The compound library was developed at the Center for Chemical Methodology and Library Development at Boston University (CMLD-BU) and comprised 2,070 compounds with high stereochemical and positional variation to provide broad coverage of chemical space in a limited screen.

None of the library compounds reduced early Venus expression at 12 h postinfection with LREV virus. The majority also did not affect late mCherry expression. However, three compounds showed reductions between 30-70% at a screening concentration of approximately 10 μM. Of these three compounds, one did not show activity upon re-synthesis and another was antiviral but showed a cell-type specific cytopathic effect. The third compound, CMLDBU6 128, was strongly antiviral, not cytotoxic, and was chosen for further characterization.

CMLDBU6 128 is a pyridopyrimidone compound. It was constructed by an auric acid-catalyzed cyclization19 of dihydropyrimidinones possessing pendant propargyl groups20 (compounds 1 & 2, FIG. 1B). Initial synthesis methods afforded only small amounts of CMLDBU6128 3a (<10%). The conversion of ester 2a to 4a was similarly low-yielding, whereas compounds 1b, 1c, 2b, and 2c readily underwent cyclization in 63-94% isolated yield. A more efficient synthesis of CMLDBU6128 was thus developed and is described herein; TMS-pyrimidone 3c was subjected to AgF-mediated desilylation21-23 to afford 3a in 53% yield. All compounds in this collection were evaluated in viral proliferation assays: compounds 3b and 4c demonstrated antiviral activity but were significantly less active than CMLDBU6 128. The optimized synthetic procedure afforded sufficient quantities of CMLDBU6128 to enable further study.

The effect of CMLDBU6128 on a single reporter virus with Venus under control of the late F17R promoter (late Venus; LV virus) is shown in FIG. 1C. The $IC_{50}$ for LV reporter expression was ~5.3 µM and $IC_{90}$ was ~10.4 µM, and similar $IC_{50}$s were observed in both A549 and HeLa cells with little to no cell cytotoxicity at up to 80 µM. A compound concentration of 20 µM was chosen for subsequent experiments.

Figure 1D:
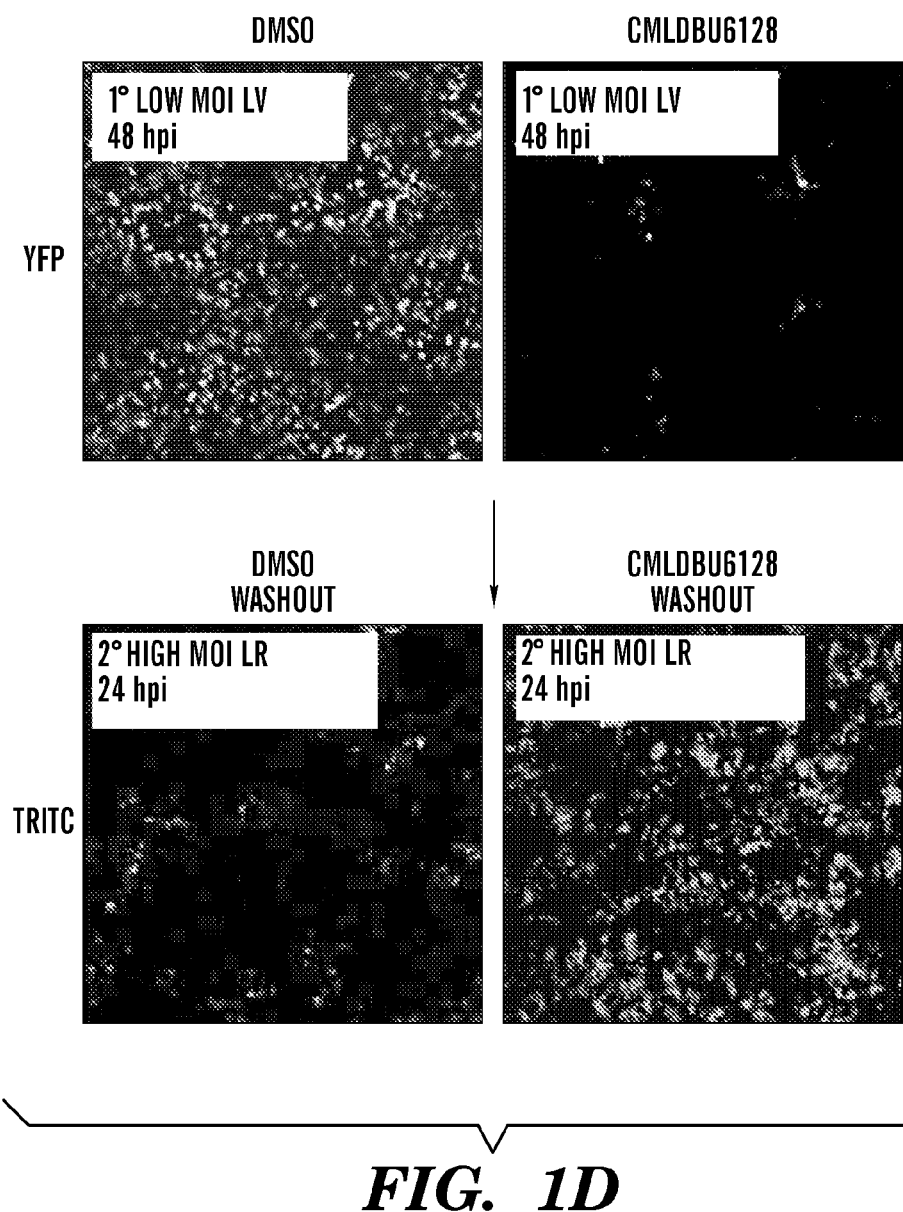
FIG. 1D shows sequential low MOI-high MOI infection. A549 cells were infected with low MOI Venus-expressing reporter virus and infections proceeded for 48 h (primary infection). Medium exchange was followed by high MOI infection with mCherry-expressing reporter virus for 24 h (secondary infection). Images were taken using a 2.5× objective.

These non-cytotoxic, antiviral properties of CMLDBU6128 are further illustrated in FIG. 1D. A549 cells were infected with a low MOI of LV virus and infection was allowed to proceed for 48 h. With dimethylsulfoxide (DMSO), but not CMLDBU6128, this resulted in a monolayer of Venus-expressing cells from complete virus spread after the primary low MOI infection. Medium exchange to drug-free medium was then followed by secondary infection with high MOI of a single reporter virus with mCherry under control of the late F1 7R promoter (late red, LR virus). mCherry-expressing cells were observed only after the CMLDBU6 128-limited primary infection as vaccinia-infected cells do not support super-infection[24][25]. These data showed that CMLDBU6 128 limits viral spread after low MOI infection and that viable, infection-supporting cells remain in this limited infection.

Figure 2A:
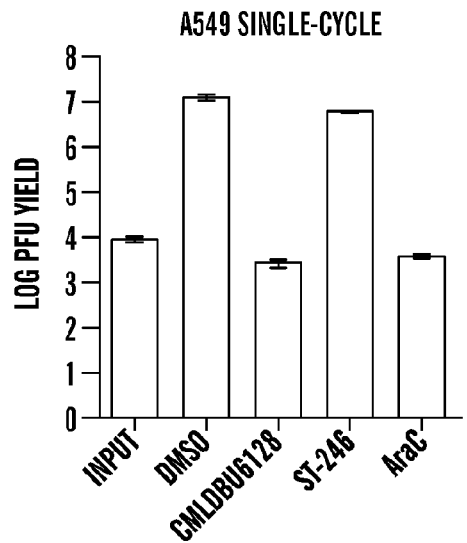
FIG. 2A shows single-cycle growth curve in A549.
Figure 2B:
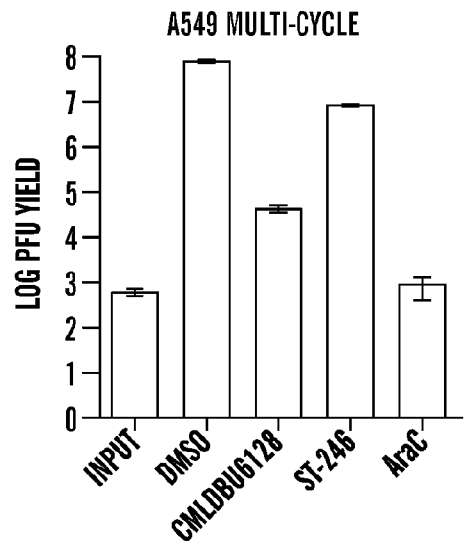
FIGS. 2B and 2C demonstrate multi-cycle growth curves in A549 and Vero, respectively.
Figure 2C:
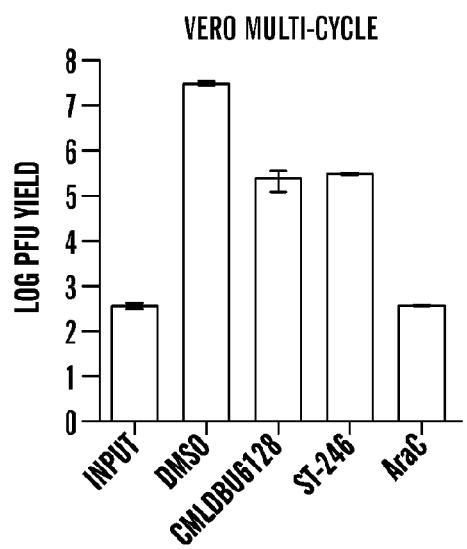
Figure 2D:
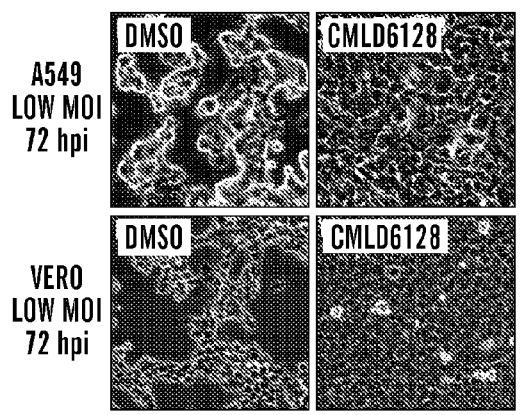
FIG. 2D demonstrates phase-contrast microscopy of cell monolayers of A549 and Vero at the endpoint of multi-step growth curves from B and C above (10× objective). All growth curves were with vaccinia strain Western Reserve. Compound concentrations used were as follows: 20 µM CMLDBU6 128, 5 µM ST-246, and 1 µg/ml of AraC.

To confirm that reduced viral reporter expression correlated with decreased virus production, single- and multi-cycle growth assays with wild-type vaccinia strain Western Reserve were performed (FIGS. 2A-2D). Two reference compounds were included: ST-246, which inhibits the assembly of infectious viral progeny, and AraC, a nucleoside analog and inhibitor of viral DNA replication[26][16]. In A549 single-cycle assays (FIG. 2A), virus yield was reduced by 3.6-log (CMLDBU6128), 0.3-log (ST-246), and 3.5-log (AraC). In A549 multi-cycle assays (FIG. 2B), virus yield was reduced by 3.3-log (CMLDBU6128), 1.0-log (ST-246), and 4.5-log (AraC). Similar results were obtained in multi-cycle assays on Vero cells, showing that the inhibitory effect was not cell- or species-specific (FIG. 2C; 1.9-, 2.0-, and 4.9-log reductions by CMLDBU6128, ST-246, and AraC, respectively). Microscopy of the multi-cycle endpoints with DMSO or CMLDBU6128 showed intact cell monolayers with the inhibition of low MOI virus spread (FIG. 2D).

CMLDBU6128 Interferes with Viral Intermediate and Late Gene Expression

To determine when during viral replication a CMLDBU6 128 block occurs, we utilized a series of single reporter viruses (Table 1). Early Venus (EV virus) contains Venus under control of the early C11B promoter, intermediate Venus (IV virus) contains Venus under control of the intermediate G8R promoter, and late Venus (LV virus) is described above. A fluorescence plate reader was used for real-time monitoring of Venus expression after high MOI infection of A549 cells with EV, IV, or LV virus in the presence of DMSO or CMLDBU6128 (FIGS. 3A-3E).

Figure 3A:
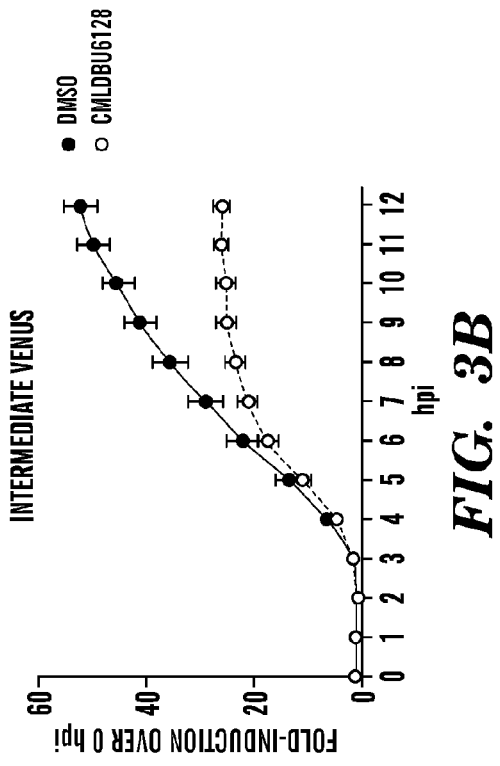
FIGS. 3A-3C shows A549 cells infected with high MOI early Venus (EV; 3A), intermediate Venus (IV; 3B), or late Venus (LV; 3C) reporter viruses in the presence of DMSO or CMLDBU6 128. Viral reporter fluorescence was measured hourly for 12 h.
Figure 3B:
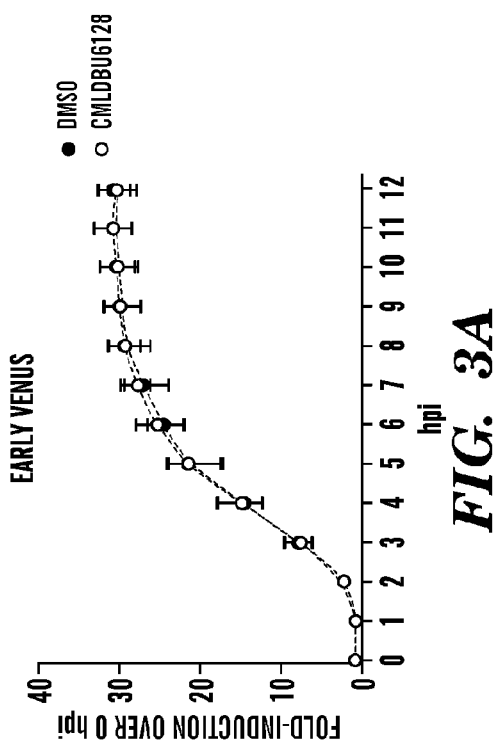
Figure 3C:
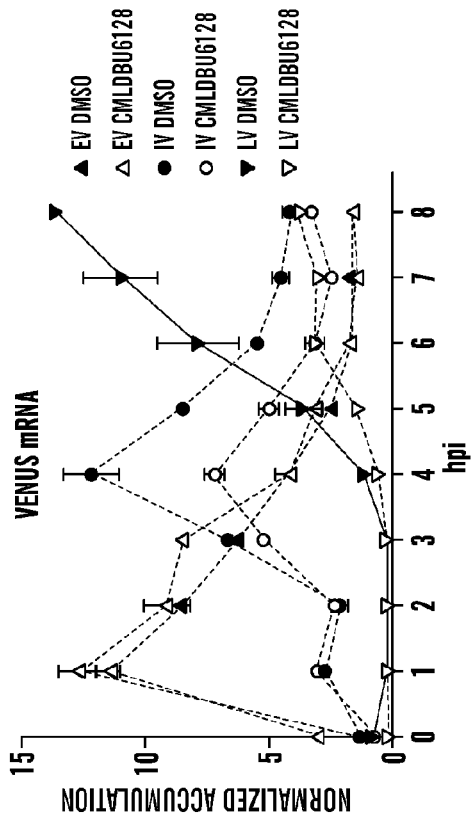

Reporter expression driven by these canonical viral promoters occurred with the expected timing and magnitude, and there was no detectable Venus expression with a reporter virus that contained Venus with no preceding promoter element (promoter-less Venus; PLV virus. FIGS. 3A-3C). In the presence of CMLDBU6128, EV reporter expression was unaffected and had an induction profile that super-imposed with DMSO treatment (FIG. 3A). In contrast IV reporter expression initiated with the proper kinetics but only reached half-maximal levels (FIG. 3B). A more pronounced defect was observed with LV reporter expression, where maximum fluorescence was reduced by approximately 85% (FIG. 3C). Virtually identical results were obtained when CMLDBU6128 was added 4 h before virus as opposed to simultaneously, indicating that these differences were not due to kinetic limitations of drug uptake or action.

Figure 3D:
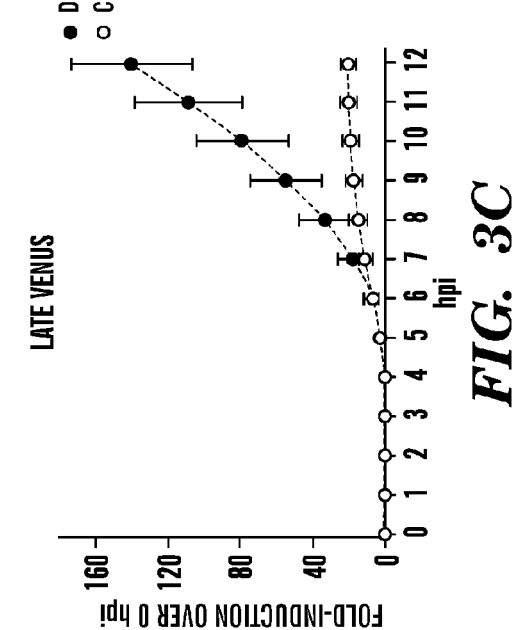
FIG. 3D shows promoter-dependent Venus mRNA accumulation over a time-course of infection with EV, IV, or LV.

We performed mRNA analysis to determine if the observed defects were due to reduced reporter transcript accumulation. Promoter-dependent mRNA accumulation was calculated by normalizing Venus RT-PCR threshold cycles (Ct) after EV, IV, or LV virus infection to Ct values after infection with promoter-less PLV virus. Over an 8 h time-course, peak Venus mRNA accumulations for EV, IV, and LV infections occurred at 1, 4, and 8 h postinfection, respectively (FIG. 3D). EV reporter mRNA accumulation was unaffected by CMLDBU6128. However IV and LV reporter mRNA accumulation initiated correctly but failed to reach maximal levels. CMLDBU6128 reduced peak IV reporter mRNA by 41% and peak LV reporter mRNA by 73%, mirroring the expression defects above.

These results with single reporter viruses were validated by microscopy using the multi-reporter triple virus (TrpV) in which Venus, mCherry, and TagBFP were under control of early C1 1R, intermediate G8R, and late F1 7R promoters, respectively. A549 cells were infected with high MOI of TrpV and visualized at 12 h postinfection (FIG. 3E). CMLDBU6128 had no detectable effect on early Venus expression and reduced mCherry and late TagBFP expression uniformly across the infected cell population. Phase contrast imaging after this high MOI infection showed that it did not prevent the cell morphological changes associated with infection-induced cytopathic events (CPE).

CMLDBU6128 does not Inhibit Viral DNA Replication or Factory Formation

Figure 4A:
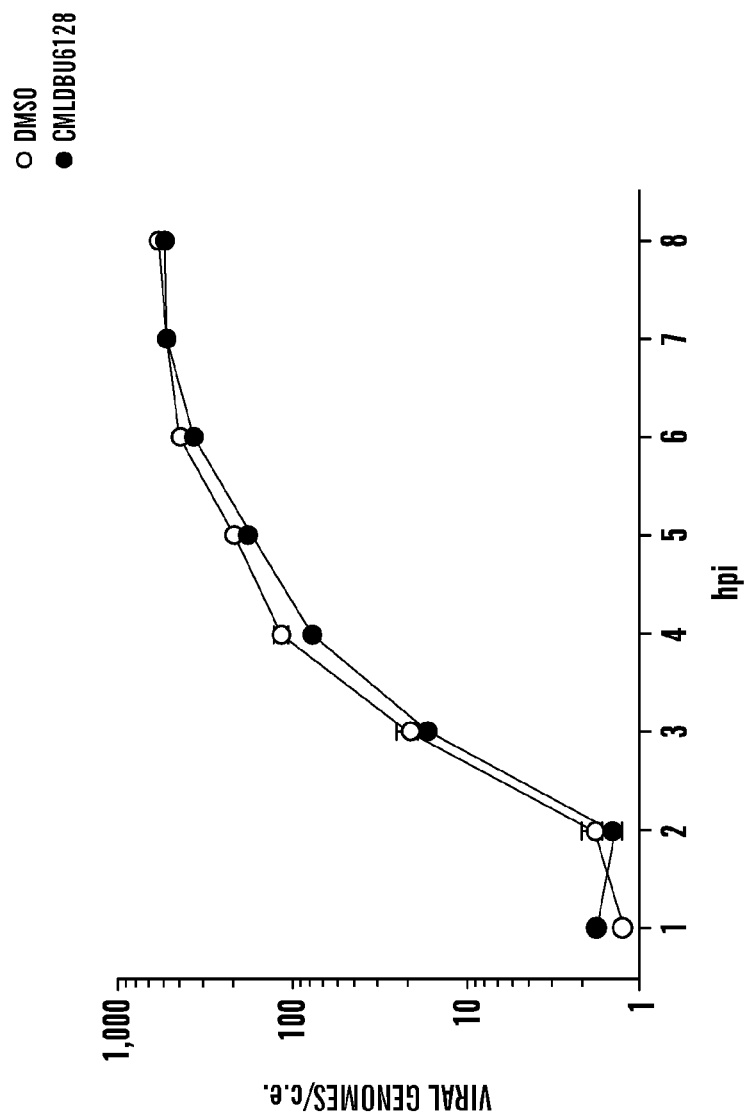
FIG. 4A shows Venus DNA copy numbers per A549 cell equivalent (c.e.) after high MOI infection with LV reporter virus. Venus copy numbers were calculated from a standard curve of Venus-containing plasmid.

Viral DNA replication resets the transcriptional landscape to post-replicative gene expression, and consequently DNA replication inhibitors cause a loss of intermediate and late gene expression[27][28]. Typically, there is also concomitant failure to terminate early gene expression, an effect that was not seen with CMLDBU6 128 (FIG. 3A). To monitor viral DNA replication we tracked Venus DNA copy numbers after infection of A549 cells with LV virus. FIG. 4A is a log-scale plot of Venus copies per cell equivalent (c.e.) and shows that viral DNA replication occurred normally in the presence of CMLDBU6128. The onset of DNA replication was between 2-3 h postinfection and Venus DNA copies/c.e. increased from 1-2 (1 h postinfection) to 574 and 529 (8 h postinfection) with DMSO and CMLDBU6128, respectively.

Figure 4B:
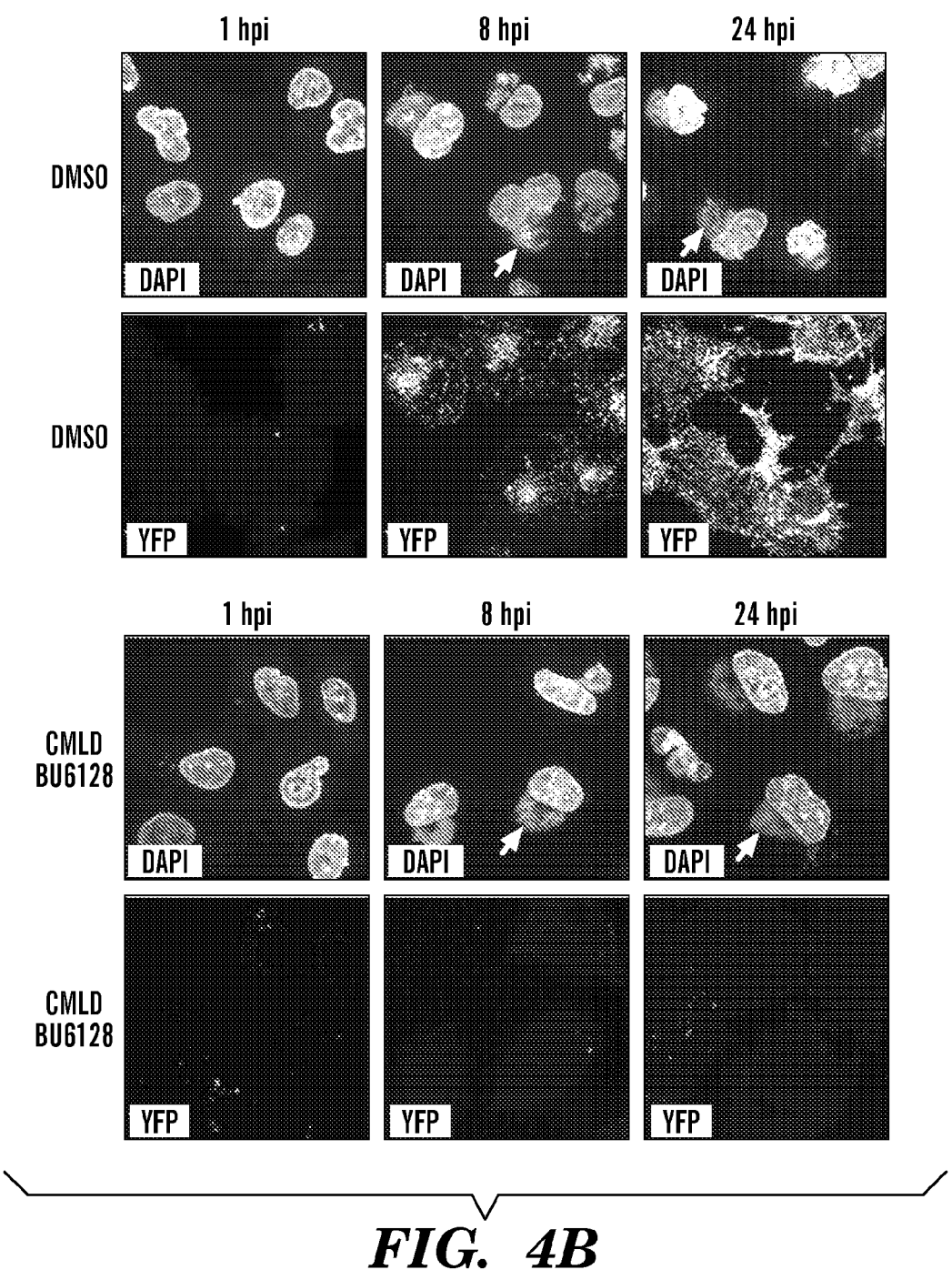
FIG. 4B shows high magnification microscopy after infection of A549 cells with Venus-A4L virus. DMSO- or CMLDBU6 128-treated infections are shown at 1, 8, and 24 h postinfection. Cells were fixed and stained with DAPI before visualization of viral DNA factories (DAPI) and Venus-A4L (YFP). Images taken using a 63× objective. Arrowheads point to representative perinuclear viral factories.

Viral factory morphology also appeared normal in the presence of CMLDBU6128. FIGS. 4A-4B show the results of high-magnification microscopy at 1, 8, and 24 h after infection of A549 cells with a vaccinia virus harboring a Venus fusion of the late-expressed viral core protein A4L (Venus-A4L virus). With both DMSO and CMLDBU6 128 treatment, a DAPI-staining perinuclear viral factory was evident by 8 h and persisted to 24 h postinfection (FIG. 4B). However, only in the control infection was Venus-A4L visible as punctuate signal in and around viral factories at 8 h postinfection. By 24 h this signal had spread throughout the cells as Venus-A4Lcontaining progeny viruses trafficked away from the factory[29][39]. The CMLDBU6128-induced defects in intermediate and late viral gene expression were therefore uncoupled from any gross defects in viral DNA replication or factory formation.

CMLDBU6128-arrested Infection has a General Loss of Protein Synthesis

Figures 5A, 5B:
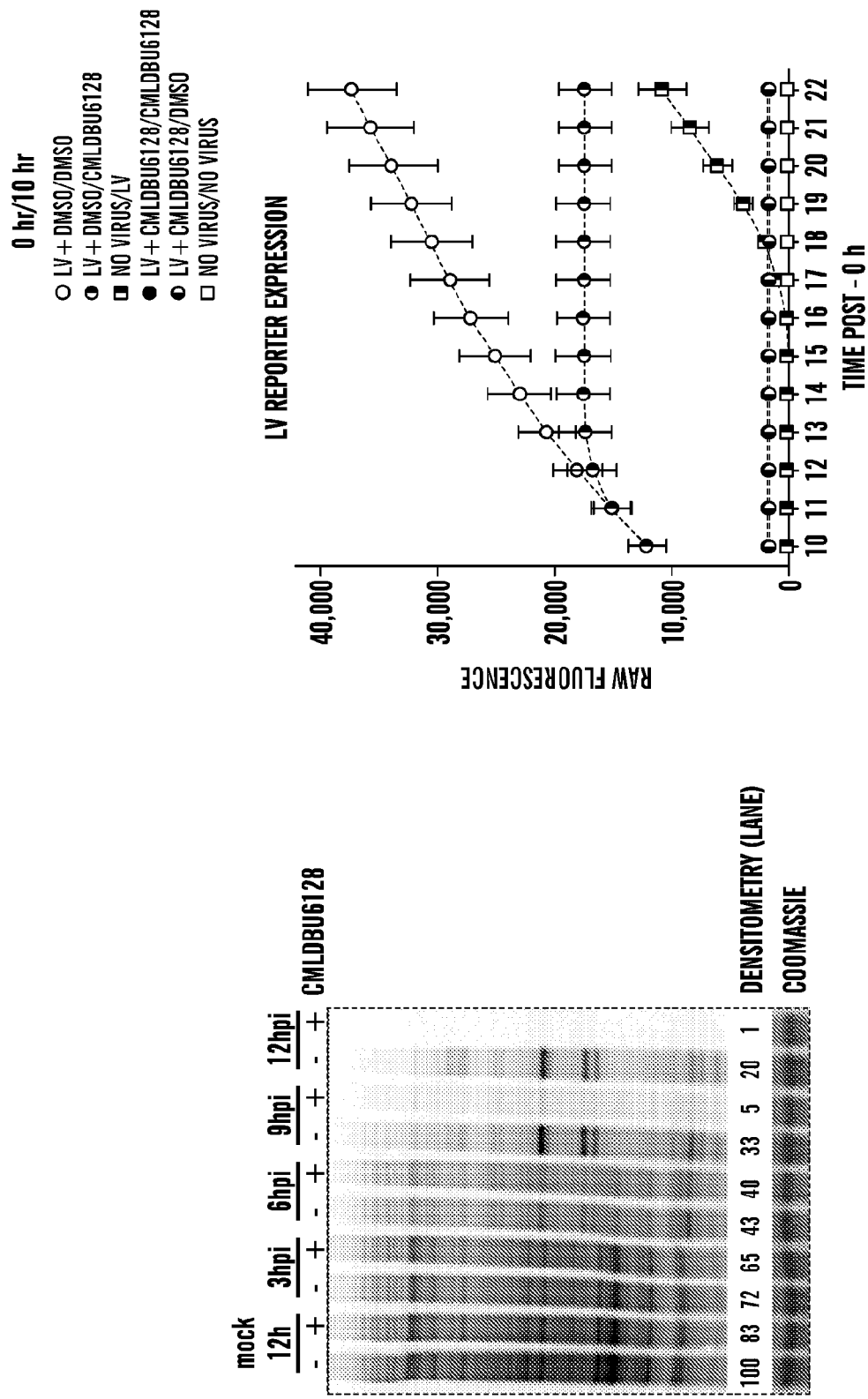
FIG. 5A demonstrates $^{35}$S methionine labeling of cells to visualize active translation. Densitometry values are provided normalized to 12 h mock-infected cells ("-" CMLDBU6 128). A representative slice of the Coomassie-stained gel is also shown.
FIG. 5B depicts a time-course analysis of Venus expression in A549 cells subjected to various treatments. The legend indicates the treatments at time 0 h and at time 10 h, separated by "/". Reporter fluorescence was measured hourly for 12 h after the initial 10 h treatment, up to 22 h. "LV" indicates high MOI infection with late Venus reporter virus. For example LV+DMSO/CMLDBU6128 indicates an initial treatment of high MOI LV reporter virus in the presence of DMSO, followed 10 h later by medium removal and replacement with CMLDBU6128-containing medium.
Figure 6A:
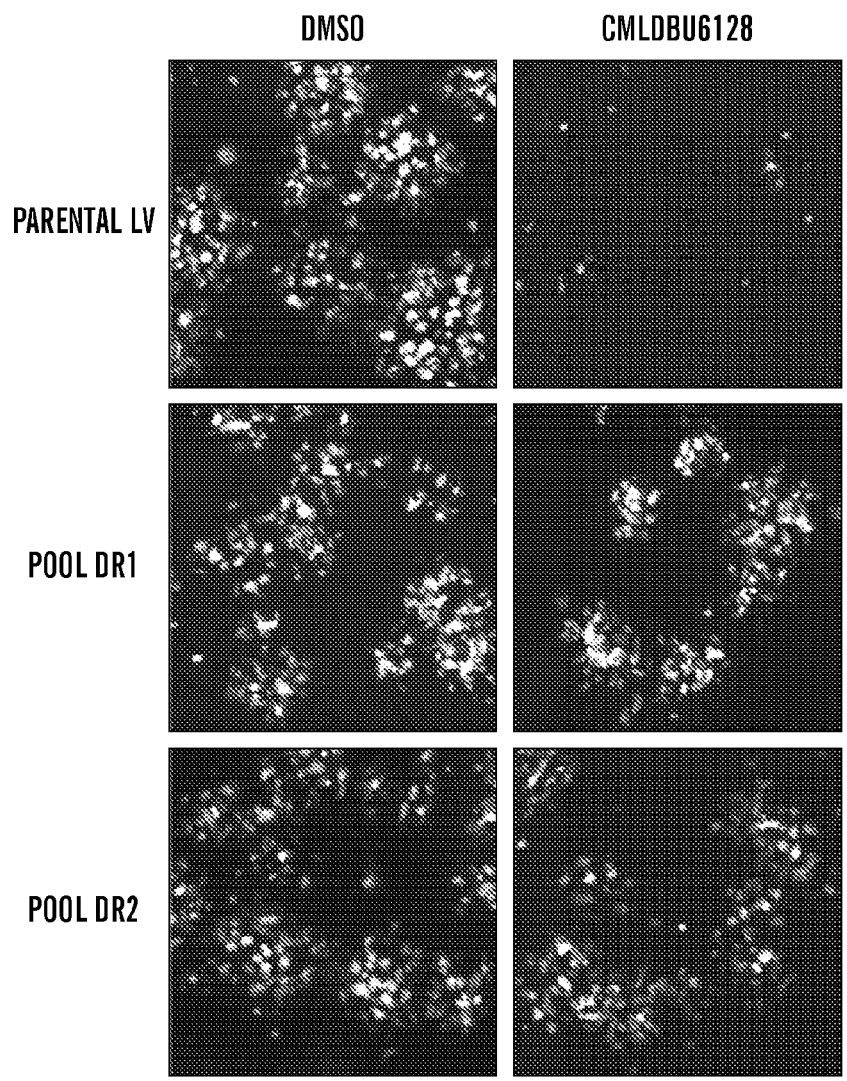
FIG. 6A shows fluorescent foci from low MOI infection of A549 cell monolayers with parental LV or two selection pools (DR1 and DR2) in the absence or presence of CMLDBU6 128. Images taken using a 2.5× objective.
Figure 8A:
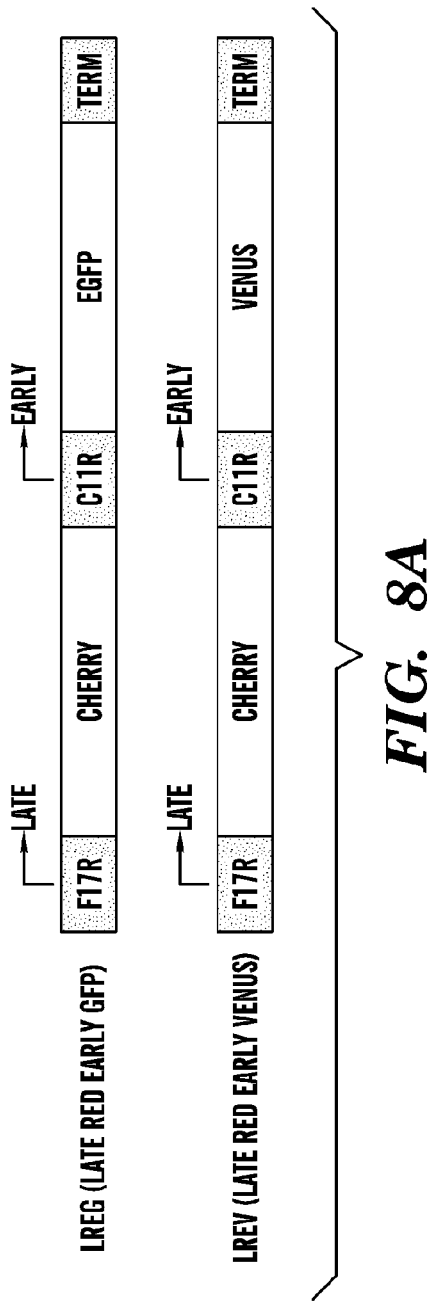
FIG. 8A shows a schematic of inserts used in one embodiment of the aspects described herein for Late Chemy Early GFP (LREG) and Late Chemy Early Venus (LREV) multi-reporter viruses. There are no intervening sequences between promoter and reporter elements. Inserts were placed between the Vaccinia J4R and J5L genes.
Figure 8B:
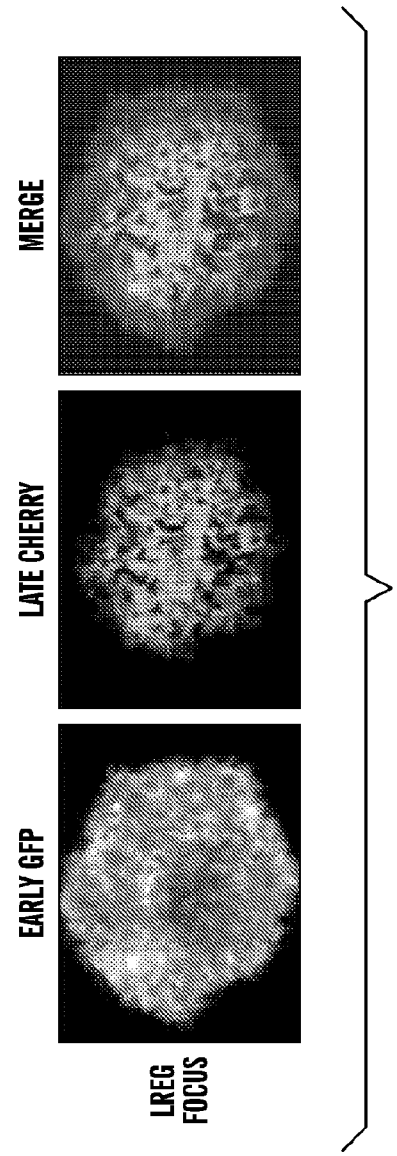
FIGS. 8B-8C show GFP and Chemy fluorescence in a focus of Vero cells 48 hpi following low MOI LREG infection, and a summary of the results obtained 10× magnification.
Figure 8C:
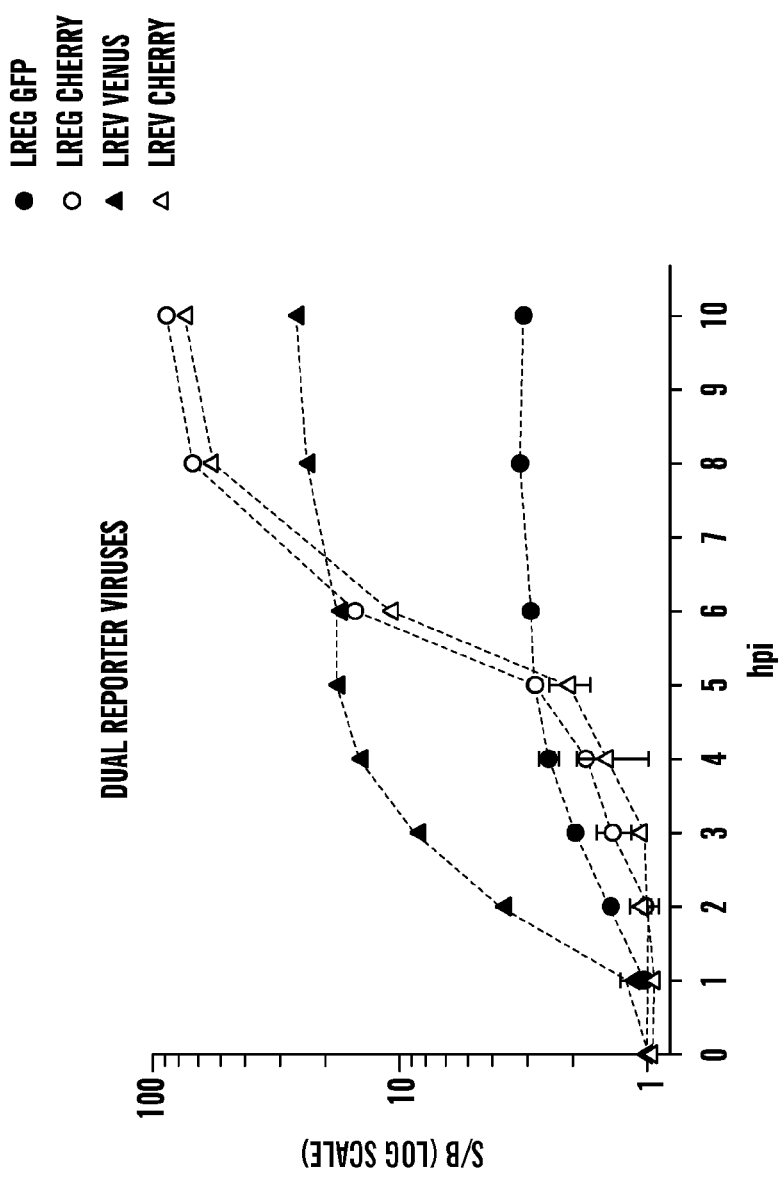
Figure 8D:
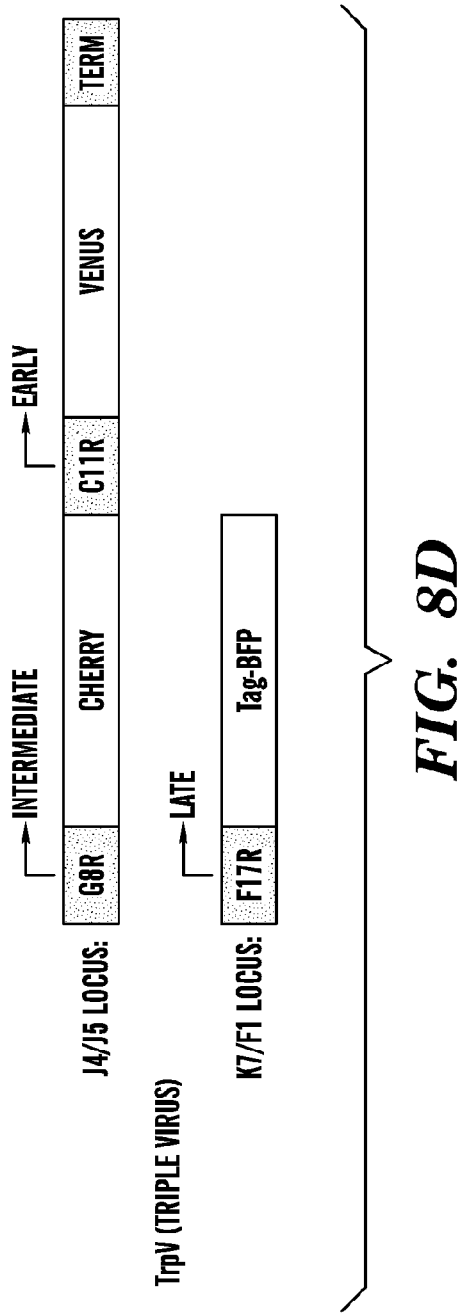
FIG. 8D shows a schematic of the inserts for Intermediate Chemy, Early Venus, and Late Tag-BFP in the multi-reporter Triple Virus (TrpV). Intergenic insertion sites are noted (J4/J5 and K7/F1).
Figure 8E:
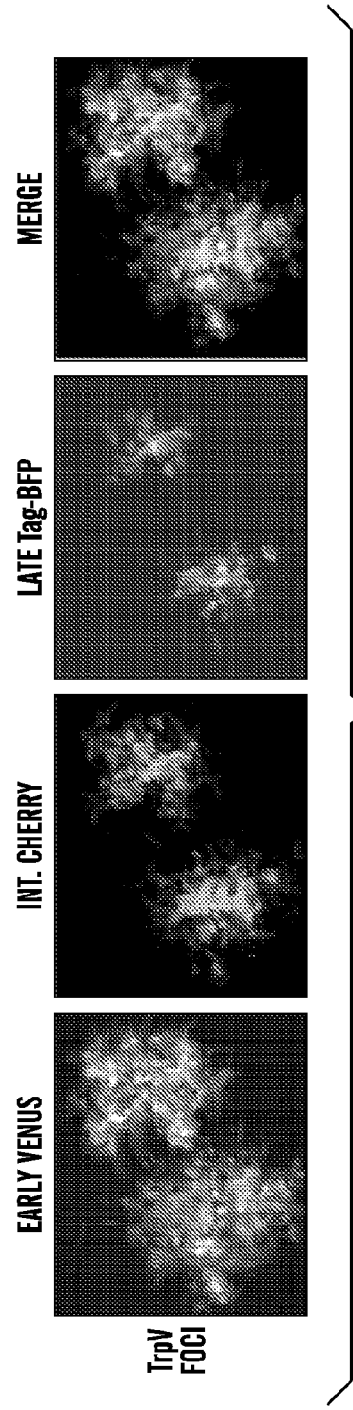
FIG. 8E shows Venus, Chemy, and Tag-BFP fluorescence in two foci of A549 cells 24 hpi following low MOI TrpV infection. 10× magnification.

To establish if CMLDBU6128 inhibited expression of a few or all intermediate and late genes, we used 35 S-methionine/cysteine pulse-labeling at times postinfection to monitor active protein translation (FIG. 5A). Cellular protein synthesis in mock-infected cells was unaffected after 12 h incubation with CMLDBU6 128. In control infected cells a characteristic shut-off of host gene expression and transition to viral protein synthesis was observed. While CMLDBU6 128 treatment did not prevent this host cell shut-off, viral protein synthesis was globally reduced. The appearance of viral proteins was diminished slightly at 6 h postinfection and greatly reduced at late time-points. Despite the virtual absence of active protein synthesis, these infection-arrested cells continued to be viable in metabolic activity assays at 12 and 24 h after infection.

Because viral gene expression occurs in a cascade mechanism, we next tested whether delayed drug addition could inhibit established late gene expression. We also tested whether drug removal would result in a recovery of late gene expression. For quantitative kinetic measurement, the effect on reporter expression after infection with LV virus was analyzed (FIG. 5B). Cells received an initial 10 h treatment followed by medium removal and second treatment (designated as 0 h treatment/10 h treatment) and LV reporter fluorescence was measured hourly for 12 h, up to 22 h. Control infections showed high Venus expression at 10 h and a steady increase over the time-course. CMLDBU6128 addition to an unimpeded 10 h infection resulted in a flattening of late reporter expression within 2 h. The CMLDBU6128-arrested infection had significantly reduced Venus expression at 10 h, as expected. However drug removal did not result in a restart of reporter expression, and Venus fluorescence was indistinguishable from that with sustained drug inclusion. By comparison infection of cells with LV virus at 10 h showed a clear rise in reporter expression within this time-course. These results indicate that CMLDBU6128 can inhibit late gene expression after it is already established, and indicate that a CMLDBU6128-arrested infection is irreparably defunct.

Mutations in the Conserved Viral RNA Polymerase Bypass CMLDBU6128 Inhibition

Taken together, the results described herein indicated that CMLDBU6128 interfered with post-replicative viral mRNA accumulation. To gain insight into mechanisms, we serially passaged LV virus in the presence of CMLDBU6128 to determine if drug-resistant viruses could be obtained. After six serial passages this resulted in clear resistance to CMBLDBU6 128, as seen in low MOI viral spread assays with the final harvests of two independent selection pools (FIG. 6A; drug-resistant pools DR1 and DR2). Two clones each from the two pools were randomly chosen and plaque purified to yield clones DR1a, DR1c, DR2b, and DR2c. Single-cycle high MOI infection of A549 cells showed that these viruses were completely resistant to CMLDBU6 128 (FIG. 6B).

The parental LV virus and all four clones were sequenced by Illumina whole-genome sequencing. When compared to the reference GenBank sequence for vaccinia strain Western Reserve the parental LV virus had four potential differences: G1091A, A1092G, T194371C, and G194372T. These fell within terminal repeat regions and were likely mapping errors. In addition, all four drug-resistant viruses contained a silent mutation (G1 85627T; VACWR208P140P), which we presume was acquired by the LV stock in an intermediate passage. Each drug-resistant pool yielded a single, different coding change in the same gene. Both DR1a and DR1c had a T85842G mutation, which is a V576G mutation in the viral RNA polymerase large subunit J6R, and both DR2b and DR2c had a C86976T mutation, which is a A954V mutation in J6R (FIG. 6C). Therefore, virtually complete drug resistance was conferred by either V576G or A954V mutation in the large subunit of the multimeric viral RNA polymerase.

J6R is highly conserved among orthopoxviruses with >96% identity between vaccinia, monkeypox, cowpox, and Variola, suggesting that CMLDBU6128 might act as a broad-spectrum inhibitor. We tested the effect of CMLDBU6128 on orthopoxviruses other than vaccinia strain Western Reserve. The results of single-cycle growth assays of monkeypox Zaire 1979 (MPDX), cowpox Brighton red (CPX), and vaccinia virus strain IHDJ on A549 cells are shown in FIG. 6D. CMLDBU6 128 inhibited the replication of all these viruses and reduced viral yields by 2.5-log (MPDX), 4.0-log (CPX), and 2.4-log (VACV IHDJ). The replication of these orthopoxviruses was also inhibited on Vero cells. The results are consistent with inhibition of a conserved feature of orthopoxvirus replication by CMLDBU6128.

Discussion

We have identified novel anti-orthopoxyiral compounds from screening of a diversity-oriented synthesis compound library. Using a series of newly developed systems, we demonstrate that a pyridopyrimidinone compound CMLDBU6 128 interferes with post-replicative mRNA accumulation. This drug phenotype shares similarities with the structurally unrelated inhibitors IBT and distamycin A, although the accumulated evidence described herein indicates different mechanisms are in play[31 32 33]. The presence of CMLDBU6128 early in infection resulted in a defect partway through intermediate gene expression, and delayed addition experiments indicated that inhibition of late reporter expression could be elicited even after preceding transcriptional events had occurred. We also found that drug removal did not result in a restart of late reporter gene expression, which we believe is likely due either to irretrievable disruption of orchestrated viral events or to host-cell shutdown in the aborted infection. The observations are potentially promising for a therapeutic effect, as the window for CMLDBU6128 inhibition does not appear to be narrow, and there could be persistent inhibition after peak drug exposure.

Structurally, CMLDBU6128 does not resemble a nucleoside analog. In addition, although drug-resistant mutations mapped to viral RNA polymerase large subunit (J6R), homology modeling with the crystal structure of yeast RNA Polymerase II34 indicates that these mutations are in regions distal to the active site. This is consistent with the interpretation that the compound is not directly blocking polymerase catalytic activity. Given their putative peripheral locations, the resistance mutations could alter interactions between J6R and other polymerase subunits. In this model the resulting changes in the multimeric viral polymerase complex would allow for productive transcription despite the presence of CMLDBU6128. The finding that two independent and apparently distal mutations in J6R can confer resistance, together with the apparent stage-specificity of inhibition and differences in requirements for stage-specific gene expression 7, support such a model. However an alternative explanation is that CMLDBU6128 is a general inhibitor of viral transcription but early transcription, which is believed to occur within the viral core shortly after entry, is physically inaccessible to the drug[35][36]. In this model the observed effects of CMLDBU6128 on stage-specific reporter viruses is due to drug inaccessibility of viral cores or early factories. These possibilities are currently under investigation, as are further studies to elucidate drug mechanism of action.

Given these findings it is interesting that significant structural similarity exists between CMLDBU6128 and the HIV reverse transcriptase inhibitor Nevirapine (FIG. 7A). Comparison of the two compounds shows they are both planar 3-ring compounds with a single major sidegroup located on the center ring, and structurally they show a 73% overlap when aligned (FIG. 7B). This structural class may therefore represent a chemical space for further exploration in targeting viral polymerases more generally. The similarity of these compounds, and disparity between HIV reverse transcriptase and multimeric vaccinia RNA polymerase, may indicate that CMLDBU6128 is a general inhibitor of vaccinia transcription, potentially targeting J6R directly.

Figure 9:
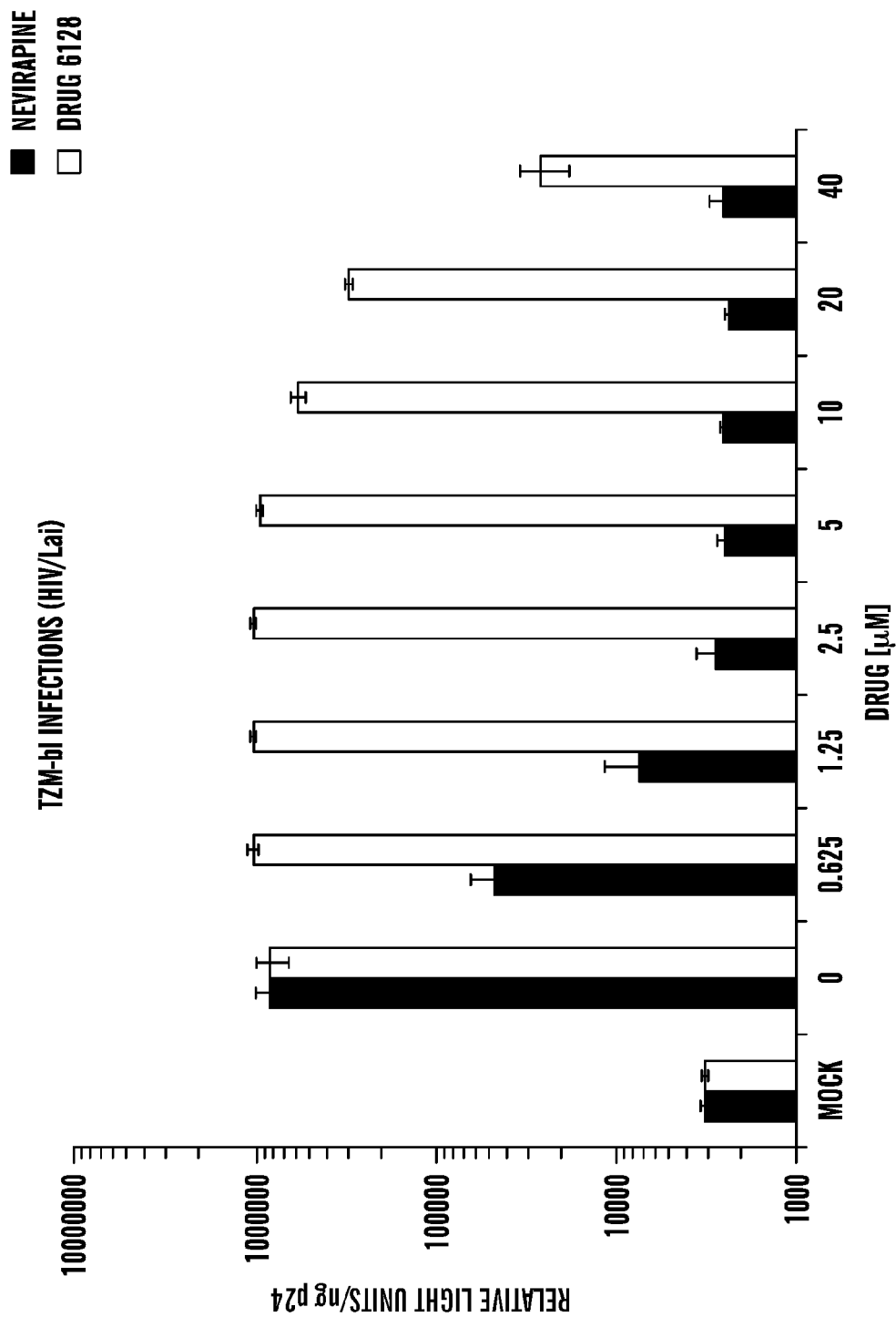
FIG. 9 demonstrates inhibition of HIV by CMLDBU6128. Cells were treated with drug following infection of cells with HIV/Lai. Following virus growth, media was harvested and used to infect TZM-bl cells. Following infection of TZM-bl cells, luciferase production was determined. Total virus production is listed as a light units normalized to nanograms of HIV p24 input. Inhibition of virus production by nevirapine and CMLDBU1628 are compared. Inhibition of HIV by CMLDBU6128 shows an $IC_{50}$ of approximately 20 micromolar.

Further, FIG. 9 demonstrates inhibition of HIV by CMLDBU6128. Cells were treated with drug following infection of cells with HIV/Lai. Following virus growth, media was harvested and used to infect TZM-bl cells. Following infection of TZM-bl cells, luciferase production was determined. Total virus production is listed as a light units normalized to nanograms of HIV p24 input. Inhibition of virus production by nevirapine and CMLDBU1628 are compared. Inhibition of HIV by CMLDBU6128 shows an $IC_{50}$ of approximately 20 micromolar.

In summary, we have identified small-molecule inhibitors that have broad spectrum activity against orthopoxviruses, as well as the retrovirus HIV. The identification of these compounds from a library with increased chemical diversity using the methods described herein demonstrates that structurally complex libraries are a source of novel chemotypes for anti-infective therapies.

Methods

Cell Culture and Viruses

A549 (CCL-85), HeLa (CCL-2), and Vero (CCL-81) were obtained from ATCC. All infections were performed and maintained in 2% fetal bovine serum-containing medium. Unless noted, VACV used in this study were strain Western Reserve or derivative. Experiments with monkeypox strain Zaire 1979, vaccinia strain IHDJ, and wild-type cowpox were performed at USAMRIID under appropriate containment. Cell viability experiments were performed by colorimetric MTT assay (Invitrogen V-1 3154). Fluorescence reporter proteins under control of canonical early, intermediate, and late viral promoters were inserted into vaccinia strain Western Reserve. Recombination strategies, promoter sequences, and insertion sites are described in detail elsewhere (Dower et al, submitted). The Venus-A4L virus contains Venus coding sequence immediately after the A4L ATG start codon in the following sequence: CAATTT-TAAAGCCTTAAATGGACTTCTTTAACAAGTTCTC (SEQ ID NO: 1). A flexible glycineserine linker encoded by the sequence GGTGGAGGCGGTTCA (SEQ ID NO: 2) was introduced between Venus and A4L.

Library Screening and Compounds

Screening library generation and chemical syntheses were performed at the Chemical Methodology and Library Development group at Boston University (CMLD; Boston University, Boston, Mass.). A549 cells were seeded at 20,000 cells/well in 96-well plates (Corning 3603) the previous day and infected with MOI 10 LREV in the presence of compound. Final compound concentrations were estimated to be approximately 10 µM. At 12 h postinfection, cells were fixed with PBS containing 4% formaldehyde for next-day scoring. Well fluorescence was measured in a Tecan plate reader to identify wells with reduced viral reporter fluorescence (see below). ST-246 was obtained from Siga Labs (Corvalis, Oreg.). AraC was from obtained from Sigma (C6645). Unless noted, compound concentrations used were as follows: 20 µM CMLDBU6128, 5 µM ST-246, and 1 µg/ml AraC.

CMLDBU6128 Synthesis 4-acetyl-3-phenyl-6-(trimethylsilyl)-2,3,7,8-tetra-hydro-1H-pyrido[1,2-c]pyrimidin-1-one (3c)

Compound 1c (110 mg, 0.32 mmol, 1.0 equiv) and auric acid trihydrate (13 mg, 0.03 mmol, 10 mol %) were weighed into a two-dram reaction vial which was immediately capped, purged, and flushed with argon. Anhydrous 1,2-dichloroethane (3.2 mL, 0.1M) was introduced by syringe and the sealed reaction was heated to 80° C. for 14 h. The reaction mixture was allowed to cool and directly purified via flash column chromatography (35% to 40% to 50% to 75% ethyl acetate in hexanes). Compound 3c (103 mg, 94%) was isolated as a tan solid.

4-acetyl-3-phenyl-2,3,7,8-tetrahydro-1H-pyrido[1,2-c]pyrimidin-1-one (3a)

Compound 3c (150 mg, 0.44 mmol, 1.0 equiv) and AgF (112 mg, 0.88 mmol, 2.0 equiv) were weighed into a foil-wrapped two-dram reaction vial equipped with a stir bar. The vial was flushed with nitrogen and 2.2 ml of a 10:2:2:1 mixture of THF:MeOH:DMSO:$H_2O$ was added. The vial was capped and the reaction stirred at room temperature overnight. The reaction mixture was filtered through a cotton plug, rinsing with dichloromethane. After solvent removal, the resultant residue was purified by flash column chromatography (20% to 40% to 70% ethyl acetate in hexanes) to afford compound 3a as an orange foam (62 mg, 53%). Detailed experimental procedures and spectroscopic data for all compounds are described herein.

Growth Curves

High MOI infections with vaccinia WR used an MOI of 10 and excess input virus was removed after 1 h by cell washing and medium change. Low MOI infections used an MOI of 0.005 and there was no 1 h medium change. For these multi-cycle assays media was refreshed every 24 h to replenish compound. Crude virus preparations were made and yields were determined on Vero cells using standard methods, with inputs determined from 1 h harvests. Monkeypox, cowpox, and vaccinia IHDJ replication curves used an MOI of 5 with 22 h postinfection endpoint.

Venus mRNA and DNA Measurement

Nucleic acid analyses for Venus RNA and DNA were performed as described in detail elsewhere (Dower et al., submitted). Briefly, RNA analysis was performed directly on cell lysates (Ambion AM 1728) using this Venus Taqman primer/probe set: AAAGACCCCAACGAGAAGC (forward) (SEQ ID NO: 3), GTCCATGCCGAGAGTGATC (reverse) (SEQ ID NO: 4), 6-FAM-TGCTGGAGTTCGT-GACCGCC-IBFQ (probe) (SEQ ID NO: 5). DNA analysis was performed similarly on cell lysates with the reverse transcription and DNAse step omitted. [35]S metabolic labeling

[35]S metabolic labeling was carried out using standard methods[37]. Gels were stained with Coomassie before 35 S visualization and measurement using a transilluminator.

Isolation of Drug-Resistant Viruses

Drug-resistant viruses were generated by serial passage in the presence of compound. The initial infection was with 1×10[5] pfu of LV reporter virus in triplicate wells of a 6-well plate. BUCMLD6 128 was added to 20 μM final concentration and infections were allowed to proceed for 2 days. A protein of the resulting crude virus preparation, ~½0th, was applied to fresh cells in the presence of 20 μM compound. This process was repeated for a total of six passages with crude virus preparations pooled at passage 2. The final two passages were with a super-inhibitory concentration of 40 μM compound. Clonal isolates from passage 6 were isolated by two plaque purifications. Picked plaques were tested for replication in the presence of 20 μM compound in 96-well plates by visualizing Venus expression, which provided seed stocks for virus amplification.

Viral Genome Sequencing

Total DNA from crude virus preparations were isolated using Qiagen Genomic DNA isolation kits. Sequencing libraries were prepared using the Illumina gDNA-sequencing kit with 5 μg of DNA input per sample. Libraries were validated and measured by qPCR then sequenced on an ILLUMINA GENOME ANALYZER IIx for 37 cycles (parental) or 84 cycles (drug-resistant clones). Resulting reads were mapped to a modified version of the vaccinia virus WR genome (NC_006998.1, parental) containing the late Venus insertion between J4L and J5R, or to the parental consensus sequence (drug-resistant clones), using MAQ (found on the worldwide web at www.ncbi.nlm.nih.gov/pubmed/1 8714091). Mutations were called using MAQ then filtered and analyzed using SNiPnfo. Between 47,668 and 5,403,566 sequencing reads were generated for each virus. Of those, between 15,472 and 417,317 mapped to vaccinia. Coverage ranged from 5.6×/97.5% to 89.6×/100. %.

Mutations for each virus were analyzed separately then correlated with their clones (e.g., DR1a with DR1b). For each clonal pair, only one coding mutation was detected: V576G J6R, with an average depth of 33 (DR1), and A954V in J6R, with an average depth of 76 (DR2)

Synthesis Methods

General Information.

All $^1$H NMR and $^{13}$C NMR spectra were recorded using Varian Unity Plus 400 or Varian Unity Plus 500 spectrometers at ambient temperature. Chemical shifts are reported in parts per million as follows: chemical shift, multiplicity (s=singlet, d=doublet, t=triplet, q=quartet, m=multiplet, br=broad), coupling constant and integration. Infrared spectra were recorded on NICOLET NEXUS 670 FT-IR ESP spectrophotometer. High resolution mass spectrometry data was obtained on a WATERS QTOF (hybrid quadrupolar/time-of-flight) API US system by electrospray (ESI) in the positive mode. Mass correction was done by an external reference using a Waters Lockspray accessory. Analytical thin layer chromatography was performed using EMD 0.25 mm silica gel 60-F plates. Flash column chromatography was performed on Sorbent Technologies 60 Å A silica gel. All reactions were performed under an atmosphere of nitrogen or argon with magnetic stirring. Dichloromethane and tetrahydrofuran were obtained from a dry solvent system (alumina). Anhydrous 1,2-dichloroethane was obtained from Sigma-Aldrich and used without further purification. Hydrogen tetrachloroaurate hydrate, gold (I) chloride and tetrakis (triphenylphosphine)palladium (0) were purchased from Strem. MP-TMT resin was obtained from Argonaut Technologies, Inc, stored at 4° C., and rinsed with three portions of dichloromethane prior to use.

Also provided herein, in some aspects, are methods of purifying pyridopyrimidinone viral inhibitors.

General Procedure for Compound Purification.

In addition to purification as described herein, all compounds underwent additional mass-guided preparative HPLC purification prior to biological assays. In addition, prior to HPLC purification all bicyclic compounds were dissolved in dichloromethane, shaken with MP-TMT resin (50 wt %) for two hours at room temperature, filtered and condensed.

General Procedure for N-3 acylation of dihydropyrimidinones.

N3-acyl dihydropyrimidinones were obtained from the parent Biginelli products[1-3] according to a modified version of Kappe's procedure.[4] Namely the parent dihydropyrimidinone (1.0 equiv) was dissolved in acetonitrile (0.5M) in a round-bottom flask under nitrogen. DMAP (0.2 equiv), triethylamine (2.5 equiv) and acetic anhydride (2.5 equiv) were added and the reaction was heated to 130° C. for 1.5 hours. The reaction was cooled to room temperature and filtered over a Buchner funnel wet-packed (acetonitrile) with 3 cm of silica. After rinsing with two additional reaction volumes of acetonitrile, the mother liquor was condensed to give a residue that was triturated with ether and allowed to stand overnight before isolating by filtration.

1,1'-(4-methyl-2-oxo-6-phenyl-2,3-dihydropyrimidine-1,5(6H)-diyl)diethanone (S1)[5]

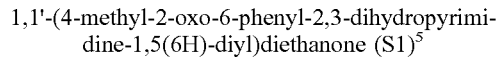

Tan solid (12.2 g, 69%); mp: 181-183° C.; TLC (EtOAc: Hexanes, 1:1 v/v): $R_f$=0.24; $^1$H NMR (500 MHz, DMSO-d6) δ 10.14 (br s, 1H), 7.34-7.28 (m, 2H), 7.27-7.22 (m, 1H), 7.16 (d, J=7.6 Hz, 2H), 6.59 (s, 1H), 2.43 (s, 3H), 2.34 (s, 3H), 2.29 (s, 3H); $^{13}$C NMR (125 MHz, DMSO-d6) M94.1, 170.8, 150.9, 146.8, 139.6, 128.4, 127.6, 126.1, 113.9, 51.3, 30.3, 25.6, 18.1; IR (thin film): 3253, 1722, 1628 cm$^{-1}$; HRMS (m/z): [M+H]$^+$ calcd. for $C_{15}H_{16}N_2O_3$, 273.1239. Found, 272.1248.

methyl 3-acetyl-6-methyl-2-oxo-4-phenyl-1,2,3,4-tetrahydropyrimidine-5-carboxylate (S2)

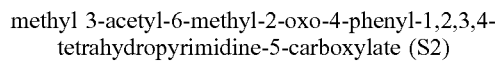

Off-white solid (3.62 g, 62%); mp: 156-159° C.; TLC (EtOAc:Hexanes, 1:1 v/v): $R_f$=0.46; $^1$H NMR (400 MHz, CDCl$_3$) δ 8.48 (br. s., 1H), 7.40-7.14 (m, 5H), 6.63 (s, 1H), 3.68 (s, 3H), 2.53 (s, 3H), 2.37 (s, 3H); $^{13}$C NMR (100 MHz, CDCl$_3$) δ 171.4, 165.4, 152.7, 145.8, 139.5, 128.6, 127.9, 126.7, 105.2, 53.1, 51.6, 26.5, 17.6; IR (thin film): 3230, 1700, 1647 cm$^{-1}$; HRMS (m/z): [M+Na]$^+$ calcd. for $C_{15}H_{16}N_2O_4Na$, 311.1008. Found, 311.1010.

General procedure for N-1 alkylation of N-3-acyl dihydropyrimidinones

N-Acyl dihydropyrimidinone (S1 or S2) (1.0 equiv) and triphenylphosphine (1.2 equiv) were charged into an oven-dried, nitrogen-flushed flask. Anhydrous THF (0.2M) was added, followed by the requisite alcohol (1.2 equiv). DIAD (1.2 equiv) was then introduced dropwise via syringe (caution: DIAD addition is slightly exothermic). The reaction was stirred at room temperature for 24-4 8 hours until TLC indicated full consumption of starting material (50% EtOAc in hexanes, visualized with UV and p-anisaldehyde stain). Upon reaction completion, the mixture was diluted to quadruple volume with dichloromethane and the resultant solution was washed with brine, dried over sodium sulfate, filtered, condensed in vacuo and purified by flash column chromatography as specified.

1,1'-(4-methyl-2-oxo-6-phenyl-3-(prop-2-yn-1-yl)-2,3-dihydropyrimidine-1,5(6H)-diyl)diethanone (S3)

White solid (3.4 g, 74%); Purification: flash column chromatography, gradient of 5% to 10% to 13% EtOAc in hexanes followed by short column eluting with 2% methanol in chloroform to remove hydrazine dicarboxylate contamination. mp: 116-118° C.; TLC (EtOAc:Hexanes, 1:1 v/v): Rf=0.50; $^1$H NMR (500 MHz, CDCl$_3$) δ 7.30 (s, 5H), 6.70 (s, 1H), 4.59 (dd, J=2.3, 18.0 Hz, 1H), 4.35 (dd, J=2.2, 18.0 Hz, 1H), 2.67 (s, 3H), 2.56 (s, 3H), 2.32 (t, J=2.2 Hz, 1H), 2.26 (s, 3H); $^{13}$C NMR (125 MHz, CDCl$_3$) δ 196.4, 171.6, 151.4, 146.7, 137.5, 128.9, 128.5, 127.1, 117.3, 78.0, 73.0, 51.5, 33.3, 29.9, 25.8, 15.9; IR (thin film): 3274, 2123, 1700, 1601, 753, 613 cm$^{-1}$; HRMS (m/z): [M+H]$^+$ calcd. for C$_{18}$H$_{19}$N$_2$O$_3$, 311.1396. Found, 311.1402.

methyl 3-acetyl-6-methyl-2-oxo-4-phenyl-1-(prop-2-yn-1-yl)-1,2,3,4-tetrahydropyrimidine-5-carboxylate (S4)

White solid (0.74 g, 87%); Purification: flash column chromatography, gradient of 5% to 10% to 11% EtOAc in hexanes followed by short column eluting with 2% methanol in chloroform to remove hydrazine dicarboxylate contamination; mp: 99-101° C.; TLC (EtOAc:Hexanes, 1:1 v/v): Rf=0.53; $^1$H NMR (400 MHz, CDCl$_3$) δ 7.35-7.19 (m, 5H), 6.72 (s, 1H), 4.58 (dd, J=2.3, 18.0 Hz, 1H), 4.38 (dd, J=2.3, 18.0 Hz, 1H), 3.73 (s, 3H), 2.72 (s, 3H), 2.55 (s, 3H), 2.35 (t, J=2.3 Hz, 1H); $^{13}$C NMR (100 MHz, CDCl$_3$) δ 171.5, 165.5, 151.7, 148.1, 128.5, 128.1, 126.6, 109.4, 78.0, 72.8, 51.8, 51.0, 33.3, 25.8, 15.6; IR (thin film): 3279, 2952, 2123, 1699, 1641, 625 cm$^{-1}$; HRMS (m/z): [M+Na]$^+$ calcd. for C$_{18}$H$_{18}$N$_2$O$_4$Na, 349.1164. Found, 349.1166.

1,1'-(3-(but-2-yn-1-yl)-4-methyl-2-oxo-6-phenyl-2,3-dihydropyrimidine-1,5(6H)-diyl)diethanone (S5)

White solid (612 mg, 69%); Purification: flash column chromatography, gradient of 5% to 10% to 15% to 20% EtOAc in hexanes. Tailing fractions heavily contaminated with hydrazine dicarboxylate were pooled and re-purified on a short silica column with 2% methanol in chloroform; mp: 9 1-93° C.; TLC (EtOAc:Hexanes, 1:1 v/v): Rf=0.53; $^1$H NMR (500 MHz, CDCl$_3$) δ 7.32-7.19 (m, 5H), 6.64 (s, 1H), 4.49 (qd, J=2.3, 17.6 Hz, 1H), 4.24 (qd, J=2.3, 17.6 Hz, 1H), 2.62 (s, 3H), 2.50 (s, 3H), 2.20 (s, 3H), 1.76 (t, J=2.3 Hz, 3H); $^{13}$C NMR (100 MHz, CDCl$_3$) δ 196.2, 171.5, 151.2, 147.1, 137.6, 128.7, 128.2, 127.1, 116.9, 80.6, 73.3, 51.4, 38.6, 26.5, 15.8, 3.6; IR (thin film): 3342, 2982, 2252, 1700, 1601, 750 cm$^{-1}$; HRMS (m/z): [M+H]$^+$ calcd. for C19H21N2O3, 325.1552. Found, 325.1550.

methyl 3-acetyl-1-(but-2-yn-1-yl)-6-methyl-2-oxo-4-phenyl-1,2,3,4-tetrahydropyrimidine-5-carboxylate (S6)

White solid (3.3 g, 70%); Purification: Flash column chromatography, gradient of 5% to 10% to 12% EtOAc in hexanes. Tailing fractions heavily contaminated with hydrazine dicarboxylate were pooled and re-purified on a short silica column with 2% methanol in chloroform; mp: 92-93° C.; TLC (EtOAc:Hexanes, 1:1 v/v): Rf=0.60; NMR (400 MHz, CDCl$_3$) δ 7.39-7.11 (m, 5H), 6.74 (s, 1H), 4.58 (qd, J=2.1, 17.8 Hz, 1H), 4.34 (qd, J=2.3, 17.8 Hz, 1H), 3.76 (s, 3H), 2.75 (s, 3H), 2.58 (s, 3H), 1.84 (t, J=2.1 Hz, 3H); $^{13}$C NMR (100 MHz, CDCl$_3$) δ 171.5, 165.5, 151.6, 148.5, 128.4, 128.2, 126.6, 109.0, 80.5, 73.4, 51.7, 50.9, 33.7, 25.8, 15.5, 3.4; IR (thin film): 3391, 2951, 2233, 1699, 1640, 620 cm$^{-1}$; HRMS (m/z): [M+Na]$^+$ calcd. for C19H20N2O4Na, 363.1321. Found, 363.1323.

1,1'-(4-methyl-2-oxo-6-phenyl-3-(3-(trimethylsilyl)prop-2-yn-1-yl)-2,3-dihydropyrimidine-1,5(6H)-diyl)diethanone (S7)

White solid (986 mg, 80%); Purification: flash column chromatography, 2% to 5% EtOAc in hexanes; mp: 80-82° C.; TLC (EtOAc:Hexanes, 1:1 v/v): Rf=0.65; NMR (500 MHz, CDCl$_3$) δ 7.35-7.28 (m, 5H), 6.69 (s, 1H), 4.74 (d, J=18.1 Hz, 1H), 4.31 (d, J=18.1 Hz, 1H), 2.68 (s, 3H), 2.54 (s, 3H), 2.25 (s, 3H), 0.18 (s, 9H); $^{13}$C NMR (125 MHz, CDCl$_3$) δ 196.4, 171.6, 151.2, 147.0, 137.6, 128.9, 128.5, 127.2, 117.1, 99.3, 90.1, 51.6, 34.0, 29.9, 25.8, 16.0, −0.3; IR (thin film): 2962, 2181, 1702, 1602, 845 cm$^{-1}$; HRMS (m/z): [M+H]$^+$ calcd. for C21H27N2O3Si, 383.1791. Found, 383.1782.

methyl 3-acetyl-6-methyl-2-oxo-4-phenyl-1-(3-(trimethylsilyl)prop-2-yn-1-yl)-1,2,3,4-tetrahydropyrimidine-5-carboxylate (S8)

Colorless foam (1.0 g, 76%); Purification: flash column chromatography, 2% to 5% to 10% EtOAc in hexanes; TLC (EtOAc:Hexanes, 1:1 v/v): R$_f$=0.75; NMR (400 MHz, CDCl$_3$) δ 7.48-7.04 (m, 5H), 6.69 (br. s., 1H), 4.74 (d, J=18.4 Hz, 1H), 4.32 (d, J=18.4 Hz, 1H), 3.72 (s, 3H), 2.72 (s, 3H), 2.52 (s, 3H), 0.16 (s, 9H); $^{13}$C NMR (100 MHz, CDCl$_3$) δ 171.6, 165.6, 151.6, 148.3, 138.5, 128.5, 128.0, 126.8, 109.3, 99.4, 89.9, 51.8, 51.1, 34.1, 25.9, 15.7, −0.3; IR (thin film): 2957, 2180, 1700, 1642, 846 cm$^{-1}$; HRMS (m/z): [M+Na]$^+$ calcd. for C21H26N2O4SiNa, 421.1560. Found. 421.1572.

General Procedures for Acyl Removal:

Method A:

Starting material (1.0 equiv) was dissolved in methanol (0.2 M). (Gentle warming with a heat gun was required to fully solubilize some substrates.) Solid potassium carbonate (2.0 equiv) was added in one portion and the reaction was stirred until TLC indicated full consumption of SM (50% EtOAc in hexanes, visualized with UV and p-anisaldehyde or vanillin). Reactions were generally complete in 20-30 min. The solution was then filtered and the filter cake rinsed with chloroform. The mother liquors were reduced in vacuo and purified as specified.

Method B:

Starting material (1.0 equiv) was dissolved in THF (0.2M) under an atmosphere of nitrogen. Piperidine (20.0 equiv) was introduced via syringe and the reaction was heated to 35° C. for four hours. The THF was removed by rotary evaporation, and hexanes were added to the residual piperidine solution. After standing at room temperature for 15-20 minutes precipitated product was isolated by filtration, rinsing with hexanes, to afford solid product. If necessary, the mother liquor was condensed and precipitation was repeated to yield a second crop of product.

5-acetyl-6-methyl-4-phenyl-1-(prop-2-yn-1-yl)-3,4-dihydropyrimidin2(1H)-one (1a)

Method A. White solid (1.3 g, 99%); Purification: 5 inch silica plug, eluted with 5% methanol in dichloromethane; mp: 126-129° C. TLC (EtOAc:Hexanes, 1:1 v/v): Rf=0.29; $^1$H NMR (400 MHz, CDCl$_3$) δ 7.41-7.17 (m, 5H), 6.21 (d, J=2.0 Hz, 1H), 5.31 (d, J=3.1 Hz, 1H), 4.62 (dd, J=2.3, 17.6 Hz, 1H), 4.45 (dd, J=2.3, 17.6 Hz, 1H), 2.60 (s, 3H), 2.32 (t, J=2.3 Hz, 1H), 2.13 (s, 3H); $^{13}$C NMR (100 MHz, CDCl$_3$) δ 196.7, 152.6, 146.6, 141.8, 129.1, 128.3, 126.5, 113.9, 79.0, 72.3, 54.8, 32.4, 30.4, 16.5; IR (thin film): 3301, 1710, 1669, 1593, 738 cm$^{-1}$; HRMS (m/z): [M+H]$^+$ calcd. for C16H17N2O2 269.1290. Found, 269.1287.

methyl 6-methyl-2-oxo-4-phenyl-1-(prop-2-yn-1-yl)-1,2,3,4-tetrahydropyrimidine-5-carboxylate (2a)

Method A. White solid (350 mg, 98%); Purification: 5 inch silica plug, eluted with 5% methanol in chloroform; mp: 156-158° C.; TLC (EtOAc:Hexanes, 1:1 v/v): R$_f$=0.46; $^1$H NMR (400 MHz, CDCl$_3$) δ 7.34-6.98 (m, 5H), 6.04 (br. s., 1H), 5.36 (d, J=2.7 Hz, 1H), 4.65 (d, J=18.2 Hz, 1H), 4.46 (d, J=18.2 Hz, 1H), 3.65 (s, 3H), 2.66 (br. s, 3H), 2.32 (s, 1H); $^{13}$C NMR (100 MHz, CDCl$_3$) δ 166.3, 152.9, 148.1, 142.8, 128.7, 127.9, 126.3, 105.1, 79.1, 72.2, 54.0, 51.4, 32.4, 16.0; IR (thin film): 3282, 2123, 1671, 1630, 738 cm$^{-1}$; HRMS (m/z): [M+H]$^+$ calcd. for C16H17N2O3, 285.1239. Found, 285.1248.

5-acetyl-1-(but-2-yn-1-yl)-6-methyl-4-phenyl-3,4-dihydropyrimidin-2(1H)-one (1b)

Method A. White solid (613 mg, 99%); Purification: 5 inch silica plug, eluted with 5% methanol in chloroform; mp: 96-98° C.; TLC (EtOAc:Hexanes, 1:1 v/v): R$_f$=0.51; $^1$H NMR (400 MHz, CDCl$_3$) δ 7.45-7.16 (m, 5H), 6.34 (br. d, J=3.1 Hz, 1H), 5.30 (br. d, J=3.1 Hz, 1H), 4.53 (dd, J=2.1, 17.6 Hz, 1H), 4.42 (dd, J=2.1, 17.6 Hz, 1H), 2.61 (s, 3H), 2.14 (s, 3H), 1.84 (t, J=2.1 Hz, 3H); $^{13}$C NMR (100 MHz, CDCl$_3$) δ 196.7, 152.8, 147.3, 142.0, 129.0, 128.3, 126.5, 113.6, 80.1, 74.4, 54.7, 32.9, 30.4, 16.6, 3.6; IR (thin film): 3258, 2228, 1695, 1665, 1590, 701 cm$^{-1}$; HRMS (m/z): [M+H]$^+$ calcd. for C17H19N2O2, 283.1447. Found, 283.1438.

methyl 1-(but-2-yn-1-yl)-6-methyl-2-oxo-4-phenyl-1,2,3,4-tetrahydropyrimidine-5-carboxylate (2b)

Method A. White solid (1.3 g, 99%); Purification: 5 inch silica plug, eluted with 5% methanol in chloroform; mp: 140-142° C.; TLC (EtOAc:Hexanes, 1:1 v/v): Rf=0.51; $^1$H NMR (400 MHz, CDCl$_3$) δ 7.37-7.16 (m, 5H), 5.84 (br. s., 1H), 5.33 (br. s, 1H), 4.56 (d, J=18.0 Hz, 1H), 4.42 (d, J=18.0 Hz, 1H), 3.63 (s, 3H), 2.65 (s, 3H), 1.81 (s, 3H); $^{13}$C NMR (100 MHz, CDCl$_3$) δ 166.4, 153.0, 148.7, 143.0, 128.7, 127.8, 126.4, 104.8, 80.0, 74.4, 54.1, 51.3, 32.9, 16.0, 3.5; IR (thin film): 3235, 2201, 1672, 1625, 696 cm$^{-1}$; HRMS (m/z): [M+H]$^+$ calcd. for C17H19N2O3, 299.1396. Found, 299.1396.

5-acetyl-6-methyl-4-phenyl-1-(3-(trimethylsilyl)prop-2-yn-1-yl)-3,4-dihydropyrimidin-2(1H)-one (1c)

Method B. White solid (850 mg, 95%); Purification: precipitation from piperidine/hexanes; mp: 160-163° C.; TLC (EtOAc:Hexanes, 1:1 v/v): Rf=0.44; $^1$H NMR (500 MHz, CDCl$_3$) δ 7.49-6.94 (m, 5H), 6.23 (d, J=2.0 Hz, 1H), 5.23 (d, J=2.7 Hz, 1H), 4.75 (d, J=18.3 Hz, 1H), 4.33 (d, J=18.3 Hz, 1H), 2.58 (s, 3H), 2.08 (s, 3H), 0.13 (s, 9H); $^{13}$C NMR (125 MHz, CDCl$_3$) δ 196.6, 152.6, 147.2, 141.9, 129.1, 128.2, 126.5, 113.8, 100.5, 89.1, 54.8, 33.1, 30.4, 16.6, −0.2; IR (thin film): 3055, 2178, 1696, 1666, 1594, 739 cm-1; HRMS (m/z): [M+H]+ calcd. for C19H25N2O2Si, 341.1685. Found, 341.1673.

methyl 6-methyl-2-oxo-4-phenyl-1-(3-(trimethylsilyl)prop-2-yn-1-yl)-1,2,3,4-tetrahydropyrimidine-5-carboxylate (2c)

Method B. White solid (319 mg, 8 9%); Purification: precipitation from piperidine/hexanes; mp: 173-175° C.; TLC (EtOAc:Hexanes, 1:1 v/v): Rf=0.63; $^1$H NMR (400 MHz, CDCl$_3$) δ 7.27 (s, 5H), 5.75 (br. d, J=2.5 Hz, 1H), 5.32 (br. d, J=2.5 Hz, 1H), 4.81 (d, J=18.4 Hz, 1H), 4.38 (d, J=18.4 Hz, 1H), 3.63 (s, 3H), 2.66 (s, 3H), 0.16 (s, 9H); $^{13}$C NMR (100 MHz, CDCl$_3$) δ 166.3, 152.6, 148.5, 143.0, 128.8, 128.0, 126.4, 105.0, 100.5, 89.1, 54.3, 51.4, 33.2, 16.1, −0.2; IR (thin film): 3232, 2178, 1705, 1670, 841 cm$^{-1}$; HRMS (m/z): [M+H]+ calcd. for C19H25N2O3Si, 357.1634. Found, 357.1638.

General Procedure for Au-Mediated Cyclization Reaction:

Starting material (1.0 equiv) and chloroauric acid (10-20 mol %) were weighed into a glass reaction vial which was immediately capped, purged, and flushed with argon. Anhydrous 1,2-dichloroethane (0.2M) was introduced via syringe and the sealed reaction was heated to 80° C. overnight. Reaction progress was monitored by TLC (50% EtOAc/hexanes, visualization with UV and phosphomolybdic acid stain) or 1H NMR following removal of a small aliquot of reaction mixture. Upon sufficient consumption of starting material, the solvent was removed in vacuo and the residue was directly purified by flash column chromatography.

4-acetyl-6-methyl-3-phenyl-2,3,7,8-tetrahydro-1H-pyrido[1,2-c]pyrimidin-1-one (3b)

Catalyst loading: 10 mol %. Orange oil (63 mg, 63%); Purification: flash column chromatography, gradient of 40% to 50% to 75% ethyl acetate in hexanes; TLC (EtOAc:Hexanes, 1:1 v/v): Rf=0.16; NMR (400 MHz, CDCl$_3$) δ 7.39-7.25 (m, 5H), 7.20 (s, 1H), 5.50 (br. s., 1H), 5.37 (d, J=2.7 Hz, 1H), 4.20 (ddd, J=5.5, 6.0, 13.0 Hz, 1H), 3.52 (ddd, J=5.5, 9.0, 13.0 Hz, 1H), 2.38 (ddd, J=6.0, 9.0, 17.2 Hz, 1H), 2.28 (td, J=5.5, 17.2 Hz, 1H), 2.16 (s, 2H), 2.03 (s, 3H); $^{13}$C NMR (100 MHz, CDCl$_3$) δ 196.0, 152.9, 147.4, 142.8, 142.3, 129.1, 128.2, 126.4, 117.0, 109.4, 54.7, 38.5, 30.4, 29.1, 24.2; IR (thin film): 3277, 1689, 1655, 1600, 700 cm$^{-1}$; HRMS (m/z): [M+H]$^+$ calcd. for C17H9N$_2$O2, 283.1447. Found, 283.1444.

methyl 6-methyl-1-oxo-3-phenyl-2,3,7,8-tetrahydro-1H-pyrido[1,2-c]pyrimidine-4-carboxylate (4b)

Catalyst loading: 10 mol %. Orange oil (65 mg, 65%); Purification: flash column chromatography, gradient of 40% to 50% to 75% ethyl acetate in hexanes; TLC (EtOAc:Hexanes, 1:1 v/v): Rf=0.44; $^1$H NMR (400 MHz, CDCl$_3$) δ 7.40 (s, 4H), 7.34-7.16 (m, 4H), 5.87 (br. d, J=3.0 Hz, 1H), 5.39 (d, J=3.0 Hz, 1H), 4.17 (ddd, J=5.0, 6.0, 14.1 Hz, 6H), 3.64 (d, J=0.8 Hz, 16H), 3.49 (ddd, J=5.0, 9.0, 14.0 Hz, 6H), 2.35 (ddd, J=6.0, 9.0, 18.0 Hz, 1H), 2.24 (ddd, J=5.0, 6.0, 18.0 Hz, 1H), 1.98 (s, 3H); $^{13}$C NMR (100 MHz, CDCl$_3$) δ

166.1, 153.3, 146.4, 143.4, 128.7, 127.7, 126.2, 116.7, 100.3, 53.8, 51.3, 38.6, 29.1, 24.1; IR (thin film): 3056, 1710, 1681, 1645, 1592, 739 cm$^{-1}$; HRMS (m/z): [M+H]$^+$ calcd. for C17H19N2O3, 299.1396. Found, 299.1404.

4-acetyl-3-phenyl-6-(trimethylsilyl)-2,3,7,8-tetrahydro-1Hpyrido[1,2-c]pyrimidin-1-one (3c)

Catalyst loading: 20 mol %. Tan solid (644 mg, 99%); Purification: Flash column chromatography, 5% methanol in chloroform. mp: 179-182° C. (dec.); TLC (EtOAc:Hexanes, 1:1 v/v): Rf=0.34; NMR (500 MHz, CDCl$_3$) δ 7.42 (s, 1H), 7.32-7.17 (m, 4H), 5.95 (br. s., 1H), 5.35 (d, J=2.0 Hz, 1H), 4.01 (td, J=5.5, 12.5 Hz, 1H), 3.40 (td, J=6.5, 12.5 Hz, 1H), 2.40-2.29 (m, 2H), 2.14 (s, 3H), 0.14 (s, 9H); $^{13}$C NMR (125 MHz, CDCl$_3$) δ 195.7, 152.9, 151.7, 142.3, 141.2, 129.0, 128.2, 127.8, 126.5, 111.1, 54.5, 38.1, 30.6, 26.0, −2.7; IR (thin film): 3342, 1688, 1655, 1600, 739 cm$^{-1}$; HRMS (m/z): [M+H]$^+$ calcd. for C19H25N2O2Si, 341.1685. Found, 341.1682.

methyl 1-oxo-3-phenyl-6-(trimethylsilyl)-2,3,7,8-tetrahydro-1Hpyrido[1,2-c]pyrimidine-4-carboxylate (4c)

Catalyst loading: 20 mol %. Tan solid (140 mg, 70%); Purification: Flash column chromatography, 5% methanol in chloroform. mp: 169-172° C.; TLC (EtOAc:Hexanes, 1:1 v/v): R$_f$=0.47; $^1$H NMR (400 MHz, CDCl$_3$) δ 7.77 (br. s., 1H), 7.41-7.15 (m, 4H), 6.06 (br. s., 1H), 5.41 (br. s., 1H), 4.03 (td, J=5.5, 11.5 Hz, 1H), 3.66 (s, 3H), 3.45 (td, J=6.0, 11.5 Hz, 1H), 2.43-2.27 (m, 2H), 0.17 (s, 9H); $^{13}$C NMR (100 MHz, CDCl$_3$) δ 168.0, 153.3, 150.8, 143.3, 142.2, 128.7, 127.6, 126.2, 101.7, 53.7, 51.4, 38.1, 26.0, −2.7; IR (thin film): 3245, 1684, 1616, 839 cm$^{-1}$; HRMS (m/z): [M+H]$^+$ calcd. for C19H25N2O3Si, 357.1634. Found, 357.1632.

4-acetyl-3-phenyl-2,3,7,8-tetrahydro-1H-pyrido[1,2-c]pyrimidin-1-one (3a)

Compound 3c (150 mg, 0.44 mmol, 1.0 equiv) and AgF (112 mg, 0.88 mmol, 2.0 equiv) were weighed into a foil-wrapped two dram reaction vial equipped with a stir bar. The vial was flushed with nitrogen and 2.2 mL of a 10:2:2:1 mixture of THF:MeOH:DMSO:H2O was added. The vial was capped and the reaction stirred at room temperature overnight. The reaction mixture was filtered through a cotton plug, rinsing with dichloromethane. The solvent was removed in vacuo and the resultant residue purified by flash column chromatography (20% to 40% to 70% ethyl acetate/hexanes) to afford two fractions. The first-eluting fraction consisted of unreacted starting material 3c. The second compound eluted was desired product 3a (62 mg, 53%, orange foam). TLC (EtOAc:Hexanes, 1:1 v/v): Rf=0.13; $^1$H NMR (400 MHz, CDCl$_3$) δ 7.48-7.12 (m, 4H), 6.77 (br. s., 1H), 6.49 (td, J=3.5, 10.0 Hz, 4H), 5.38 (d, J=3.5 Hz, 1H), 4.14 (td, J=6.0, 12.5 Hz, 1H), 3.50 (ddd, J=5.5, 7.5, 12.5 Hz, 3H), 2.55-2.25 (m, 2H), 2.16 (s, 3H); $^{13}$C NMR (100 MHz, CDCl$_3$) δ 195.8, 152.7, 141.7, 135.3, 128.6, 127.7, 126.1, 121.3, 110.8, 54.0, 37.8, 29.9, 23.6; IR (thin film): 3266, 2930, 1689, 1656, 1563, 700, 561 cm$^{-1}$; HRMS (m/z): [M+H]+ calcd. for C16H17N2O2, 269.1290. Found, 269.1284.

methyl 1-oxo-3-phenyl-2,3,7,8-tetrahydro-1H-pyrido[1,2-c]pyrimidine-4-carboxylate (4a)

Compound 4c (150 mg, 0.42 mmol, 1.0 equiv) and AgF (267 mg, 2.1 mmol, 5.0 equiv) were weighed into a foil-wrapped 2 dram vial equipped with a stir bar. The vial was flushed with nitrogen and 2.1 mL of a 10:2:2:1 solution of THF:MeOH:DMSO:H2O was added. The reaction was stirred at room temperature for 48 hours. The solution was then filtered through a 1 cm pad of silica, eluting with ethyl acetate. Following rotary evaporation of the eluent, the resultant residue was purified by flash column chromatography (silica wetted with 10% EtOAc in hexanes, elution with 100 mL 15%, 100 mL 25%, 100 mL 35%, 100 mL 50% EtOAc in hexanes) to afford compound S10 (43 mg, 36%) as a tan foam. TLC (EtOAc:Hexanes, 1:1 v/v): Rf=0.28; $^1$H NMR (400 MHz, CDCl$_3$) δ 7.42 (d, J=10.0 Hz, 1H), 7.24-6.98 (m, 4H), 6.29 (td, J=5.0, 10.0 Hz, 1H), 5.74 (br. s., 1H), 5.27 (br. d, J=1.2 Hz, 1H), 4.04 (td, J=6.0, 12.8 Hz, 1H), 3.52 (s, 3H), 3.36 (ddd, J=5.0, 7.8, 12.8 Hz, 1H), 2.44-2.10 (m, 2H); $^{13}$C NMR (100 MHz, CDCl$_3$) δ 165.9, 153.2, 143.2, 142.8, 135.1, 128.8, 127.9, 126.3, 121.5, 102.5, 53.9, 51.4, 38.3, 24.1; IR (thin film): 3055, 1711, 1266, 739, 530 cm$^{-1}$; HRMS (m/z): [M+H]+ calcd. for C$_{16}$H$_{17}$N$_2$O$_3$Si, 285.1239. Found, 285.1234.

1) Kappe, C. O. & Stadler, A. The Biginelli dihydropyrimidine synthesis. Org. React. 63, 1-116 (2004); 2) Stadler, A. & Kappe, C. O., Automated library generation using sequential microwave-assisted chemistry. Application toward the Biginelli multicomponent condensation. J. Comb. Chem. 3, 624-630 (2001); 3) Kappe, C. O. & Fabian, W. M. F. Conformational analysis of 4-aryl-dihydropyrimidine calcium channel modulators. A comparison of ab initio, semiempirical and X-ray crystallographic studies. Tetrahedron 53, 2803-2816 (1997); 4) Dallinger, D., Gorobets, N.Y. & Kappe, C. O., Microwave-assisted scavenging of electrophiles utilizing polymer-supported sequestration reagents. Application to the synthesis of N$^3$-acylated dihydropyrimidine libraries. Mol. Diversity. 7, 229-245 (2003); 5) Mobinikhaledi, A., Foroughifar, N., Habibi, M. & Kalate, Z. Convenient acylation of pyrimidine derivatives using microwave irradiation. Asian J. Chem. 19, 2 19-222 (2007).

REFERENCES

1 Fenner, F. A successful eradication campaign. Global eradication of smallpox. *Rev Infect Dis* 4, 9 16-930 (1982).

2 Drazen, J. M. Smallpox and bioterrorism. *N Engl J Med* 346, 1262-1263 (2002).

3 Rimoin, A. W. et al. Major increase in human monkeypox incidence 30 years after smallpox vaccination campaigns cease in the Democratic Republic of Congo. *Proc Natl Acad Sci USA* 107, 16262-16267.

4 Reed, K. D. et al. The detection of monkeypox in humans in the Western Hemisphere. *N Engl J Med* 350, 342-350, doi: 10.1056/NEJMoa032299 350/4/342 [ph] (2004).

5 McFadden, G. Killing a killer: what next for smallpox? *PLoS Pathog* 6, e1000727.

6 Moss, B. *Poxviridae: The Viruses and Their Replication.* 5th edn, Vol. 2 (Lippincott Williams & Wilkins, 2007).

7 Broyles, S. S. Vaccinia virus transcription. *J Gen Virol* 84, 2293-2303 (2003).

8 Roberts, K. L. & Smith, G. L. Vaccinia virus morphogenesis and dissemination. *Trends Microbiol* 16, 472-479 (2008).

9 McFadden, G. Poxvirus tropism. *Nat Rev Microbiol* 3, 201-213 (2005).

10 Seet, B. T. et al. Poxviruses and immune evasion. *Annu Rev Immunol* 21, 377-423 (2003).

11 Rubins, K. H. et al. The temporal program of peripheral blood gene expression in the response of nonhuman primates to Ebola hemorrhagic fever. *Genome Biol* 8, R174, doi:gb-2007-8-8-r174 [pii] 10.1 186/gb-2007-8-8-r174 (2007).
12 Parker, S., Nuara, A., Buller, R. M. & Schultz, D. A. Human monkeypox: an emerging zoonotic disease. *Future Microbiol* 2, 17-34 (2007).
13 Prichard, M. N. & Kern, E. R. Orthopoxvirus targets for the development of antiviral therapies. *Curr Drug Targets Infect Disord* 5, 17-28 (2005).
14 De Clercq, E. Vaccinia virus inhibitors as a paradigm for the chemotherapy of poxvirus infections. *Clin Microbiol Rev* 14, 382-397 (2001).
15 Quenelle, D. C. et al. Synergistic efficacy of the combination of ST-246 with CMX001 against orthopoxviruses. *Antimicrobial agents and chemotherapy* 51, 4118-4124 (2007).
16 Yang, G. et al. An orally bioavailable antipoxvirus compound (ST-246) inhibits extracellular virus formation and protects mice from lethal orthopoxvirus Challenge. *J Virol* 79, 13139-13149 (2005).
17 Farlow, J., Ichou, M. A., Huggins, J. & Ibrahim, S. Comparative whole genome sequence analysis of wild-type and cidofovir-resistant monkeypoxvirus. *Virol J* 7, 110.
18 Andrei, G. et al. Cidofovir resistance in vaccinia virus is linked to diminished virulence in mice. *J Virol* 80, 9391-9401 (2006).
19 Saito, A., Konishi, T. & Hanzawa, Y. Synthesis of Pyrroles by Gold(I)-Catalyzed Amino-Claisen Rearrangement of N-Propargyl Enaminone Derivatives. *Org. Lett* 12, 372-374, doi:Doi 10.1021/O1902716n (2010).
20 Kappe, C. O. 100 Years of the Biginelli Dihydropyrimidine Synthesis. Tetrahedron 49, 6937-6963 (1993).
21 Furstner, A. & Radkowski, K. A chemo- and stereoselective reduction of cycloalkynes to (E)-cycloalkenes. Chem Commun, 2182-2183, doi:Doi 10.1039/B207169j (2002).
22 Trost, B. M., Osipov, M. & Dong, G. A Concise Enantioselective Synthesis of (−)-Ranirestat. Org. Lett 12, 1276-1279, doi:Doi 10.1021/O1100167w (2010).
23 Trost, B. M., Sieber, J. D., Qian, W., Dhawan, R. & Ball, Z. T. Asymmetric Total Synthesis of Soraphen A: A Flexible Alkyne Strategy. Angew Chem Int Edit 48, 5478-5481, doi:DOI 10.1002/anie.200901907 (2009).
24 Christen, L., Seto, J. & Niles, E. G. Superinfection exclusion of vaccinia virus in virus-infected cell cultures. Virology 174, 35-42 (1990).
25 Doceul, V., Hollinshead, M., van der Linden, L. & Smith, G. L. Repulsion of superinfecting virions: a mechanism for rapid virus spread. Science 327, 873-876.
26 Taddie, J. A. & Traktman, P. Genetic characterization of the vaccinia virus DNA polymerase: cytosine arabinoside resistance requires a variable lesion conferring phosphonoacetate resistance in conjunction with an invariant mutation localized to the 3'-5' exonuclease domain. J Virol 67, 4323-4336 (1993).
27 Keck, J. G., Baldick, C. J., Jr. & Moss, B. Role of DNA replication in vaccinia virus gene expression: a naked template is required for transcription of three late transactivator genes. Cell 61, 801-809 (1990).
28 Vos, J. C. & Stunnenberg, H. G. Derepression of a novel class of vaccinia virus genes upon DNA replication. Embo J 7, 3487-3492 (1988).
29 Huang, C. Y. et al. A novel cellular protein, VPEF, facilitates vaccinia virus penetration into HeLa cells through fluid phase endocytosis. J Virol 82, 7988-7999 (2008).
30 Rietdorf, J. et al. Kinesin-dependent movement on microtubules precedes actin-based motility of vaccinia virus. Nat Cell Biol 3, 992-1000 (2001).
31 Broyles, S. S., Kremer, M. & Knutson, B. A. Antiviral activity of distamycin A against vaccinia virus is the result of inhibition of postreplicative mRNA synthesis. J Virol 78, 2137-2141 (2004).
32 Katz, E., Margalith, E., Winer, B. & Goldblum, N. Synthesis of vaccinia virus polypeptides in the presence of isatin-beta-thiosemicarbazone. Antimicrob Agents Chemother 4, 44-48 (1973).
33 Prins, C., Cresawn, S. G. & Condit, R. C. An isatin-beta-thiosemicarbazone resistant vaccinia virus containing a mutation in the second largest subunit of the viral RNA polymerase is defective in transcription elongation. J Biol Chem 279, 44858-44871 (2004).
34 Knutson, B. A. & Broyles, S. S. Expansion of poxvirus RNA polymerase subunits sharing homology with corresponding subunits of RNA polymerase II. Virus Genes 36, 307-311 (2008).
35 Kates, J. & Beeson, J. Ribonucleic acid synthesis in vaccinia virus. I. The mechanism of synthesis and release of RNA in vaccinia cores. J Mol Biol 50, 1-18 (1970).
36 Rosemond-Hornbeak, H. & Moss, B. Inhibition of host protein synthesis by vaccinia virus: fate of cell mRNA and synthesis of small poly (A)-rich polyribonucleotides in the presence of actinomycin D. J Virol 16, 34-42 (1975).
37 Connor, J. H. & Lyles, D. S. Vesicular stomatitis virus infection alters the eIF4F translation initiation complex and causes dephosphorylation of the eIF4E binding protein 4E-BP1. Journal of virology 76, 10177-10187 (2002)

We claim:

1. A pharmaceutical composition comprising a pyridopyrimidinone viral inhibitor of chemical structure:

2. A method of treating an orthopoxvirus infection in a subject in need thereof, the method comprising administering to a subject having an orthopoxvirus infection, a therapeutically effective amount of any of the pharmaceutical compositions of claim 1.

3. The method of claim 2, wherein the orthopoxvirus is a Vaccinia virus or a Variola virus.

4. The method of claim 2, further comprising administration of one or more additional orthopoxvirus therapeutic agents.

5. A method of treating a lentivirus infection in a subject in need thereof, the method comprising administering to a subject having a lentivirus infection a therapeutically effective amount of any of the pharmaceutical compositions of claim 1.

6. The method of claim 5, wherein the lentivirus is HIV.

7. The method of claim 5, further comprising administration of one or more additional retroviral therapeutic agents.

8. The method of claim 7, wherein the retroviral therapeutic agent is an anti-HIV agent.

9. A method of inhibiting viral replication comprising contacting a cell infected with a virus with an effective amount of a pharmaceutical composition claim 1, wherein the virus is an orthopoxvirus or a lentivirus.

10. The method of claim 9, wherein the contacting is in vitro or ex vivo.

11. The method of claim 9, wherein the contacting is in vivo.

12. The method of claim 9, wherein the virus is an orthopoxvirus.

13. The method of claim 9, wherein the retrovirus is a lentivirus.

14. The method of claim 13, wherein the lentivirus is HIV.

15. The pharmaceutical composition of claim 1, wherein the pyridopyrimidinone viral inhibitor of Formula (I) is 4-acetyl-2,3,7,8-tetrahydro-3-phenylpyrido[1,2-f]pyrimidin-1-one (CMLDBU6128), having a chemical structure:

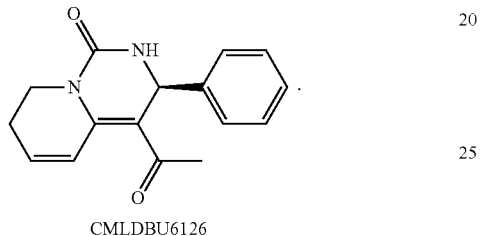

CMLDBU6126

* * * * *